(12) United States Patent
Fisher et al.

(10) Patent No.: US 6,528,534 B2
(45) Date of Patent: Mar. 4, 2003

(54) SPIRO COMPOUNDS AS INHIBITORS OF FIBRINOGEN-DEPENDENT PLATELET AGGREGATION

(75) Inventors: Matthew J. Fisher, Carmel, IN (US); Joseph A. Jakubowski, Indianapolis, IN (US); John J. Masters, Indianapolis, IN (US); Jeffrey T. Mullaney, Indianapolis, IN (US); Kenneth J. Ruterbories, Indianapolis, IN (US); Michael Paal, Hamburg (DE); Gerd Ruhter, Hamburg (DE); Theo Schotten, Vierhoefen (DE); Wolfgang Stenzel, Reinbek (DE); Robert M. Scarborough, Belmont, CA (US)

(73) Assignees: Millennium Pharmaceuticals, Inc., Cambridge, MA (US); Eli Lilly and Company, Indianapolis, IN (US)

( * ) Notice: Subject to any disclaimer, the term of this patent is extended or adjusted under 35 U.S.C. 154(b) by 13 days.

(21) Appl. No.: 09/899,886

(22) Filed: Jul. 6, 2001

(65) Prior Publication Data

US 2002/0013325 A1 Jan. 31, 2002

Related U.S. Application Data

(62) Division of application No. 09/043,846, filed as application No. PCT/US96/15703 on Sep. 27, 1996, now Pat. No. 6,291,469.
(60) Provisional application No. 60/004,557, filed on Sep. 29, 1995.

(51) Int. Cl.[7] .................... C07D 263/52; A61K 31/423
(52) U.S. Cl. ....................................... 514/376; 548/216
(58) Field of Search .......................... 548/216; 514/376, 514/375, 374

(56) References Cited

U.S. PATENT DOCUMENTS

| | | | |
|---|---|---|---|
| 5,451,578 A | 9/1995 | Claremon | 514/212 |
| 5,739,336 A | 4/1998 | Weinhardt et al. | 546/20 |
| 5,817,756 A | 10/1998 | Kyle et al. | 530/331 |
| 5,849,736 A | 12/1998 | Wityak et al. | 514/227.8 |

FOREIGN PATENT DOCUMENTS

| | | |
|---|---|---|
| EP | 540 334 | 10/1992 |
| EP | 0 635 492 A | 1/1995 |
| EP | 0655 439 A | 5/1995 |
| WO | 93 13101 | 7/1993 |
| WO | 94 08577 | 4/1994 |
| WO | 94 08962 | 4/1994 |
| WO | 94 12181 | 6/1994 |
| WO | 94 18981 | 9/1994 |
| WO | 94 22825 | 10/1994 |
| WO | 95 03303 | 2/1995 |
| WO | 95 14683 A | 6/1995 |
| WO | 96 38426 A | 12/1996 |

OTHER PUBLICATIONS

Regnier et al., Chemical Abstract 71:124304n, 1969.*
Wityak, et al., "Discovery of Potent Isoxazoline Glycoprotein IIb/IIIa Receptor Antagonists"; Journal of Medicinal Chemistry; 1997; vol. 40–, No. 1; pp. 50–60.
Rice, Chem. Abstract 70:87486, 1969.
Mach et al., Chem. Abstract 116:75693, 1992.
Bernhart et al., Chem. Abstract 119:271077, 1993.

* cited by examiner

*Primary Examiner*—Deepak R. Rao
(74) *Attorney, Agent, or Firm*—Knobbe, Martens, Olson & Bear, LLP

(57) ABSTRACT

This invention relates to certain spirocyclic compounds substituted with both basic and acidic functionality, which are useful in inhibition of platelet aggregation.

26 Claims, No Drawings

SPIRO COMPOUNDS AS INHIBITORS OF FIBRINOGEN-DEPENDENT PLATELET AGGREGATION

This is a division of U.S. application Ser. No. 09/043,846, filed Oct. 5, 1998, now U.S. Pat. No. 6,291,469, issued Sep. 18, 2001, which is the U.S. national phase of International Application No. PCT/US96/15703, filed Sep. 27, 1996, published in English, which claims the benefit under 35 U.S.C. §119(e) of U.S. Provisional Application Serial No. 60/004,557, filed Sep. 29, 1995.

FIELD OF THE INVENTION

This invention relates to novel spiro compounds useful as glycoprotein IIb/IIIa antagonists for the prevention of thrombosis.

BACKGROUND OF THE INVENTION

The most prevalent vascular disease states are related to platelet dependent narrowing of the blood supply such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, anastomosis of vascular grafts, and etc. These conditions represent a variety of disorders thought to be initiated by platelet activation on vessel walls.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin the GPIIb/IIIa binding site becomes available to fibrinogen, eventually resulting in platelet aggregation and clot formation.

Heretofore it has been proposed to block these thrombus formation sites by the use of various therapeutic agents.

There is a need in the area of cardiovascular and cerebrovascular therapeutics for new agents which can be used in the prevention and treatment of thrombi.

It is a discovery of this invention that certain novel spiro compounds block the GPIIb/IIIa fibrinogen receptor, thereby inhibiting platelet aggregation and subsequent thrombus formation. Pharmaceutical formulations containing the spiro compounds of this invention inhibit aggregation and are useful for the prophylaxis and treatment of thrombogenic diseases, such as myocardial infarction, angina, stroke, peripheral arterial disease, disseminated intravascular coagulation and venous thrombosis.

SUMMARY OF THE INVENTION

The present invention covers novel spiro compounds having a spiro nucleus formed from two fused rings, A and B, represented by the formula (I), as hereinafter defined, and all pharmaceutically-acceptable salts, solvates and prodrug derivatives thereof:

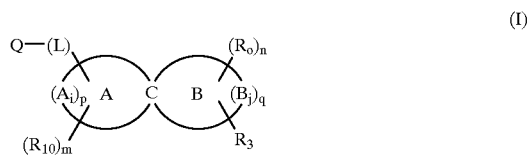

having substituents and subscripts; Q, —(L)—, $A_i$, p, $R_{10}$, m, n, $R_0$, $B_j$, q, and $R_3$, as hereinafter defined.

Another aspect of the invention is a pharmaceutical formulation containing a novel spiro compound of the invention.

Another aspect of the invention is a method of inhibiting platelet aggregation, inhibiting fibrinogen binding, or preventing thrombosis by administering to a mammal the novel spiro compounds of the invention.

Another aspect of this invention is a method of treating a human to alleviate the pathological effects of atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts; wherein the method comprises administering to said human a therapeutically-effective amount of a novel spiro compound of this invention.

DETAILED DESCRIPTION OF THE INVENTION

Definitions

The term "spiro" refers to a compound consisting of two rings having only one carbon atom in common. Spiropentane is an exemplary compound having a spiro system. Spiro systems exclude other bicyclic compounds such as naphthalene which have two or more carbon atoms in common.

The term "alkyl" used herein refers to a monovalent straight or branched chain radical of from one to ten carbon atoms, including, but not limited to methyl, ethyl, n-propyl, isopropyl, n-butyl, isobutyl, tert-butyl, n-hexyl, and the like.

The term "halosubstituted alkyl" as used herein refers to an alkyl group as just defined, substituted by one, two or three halogen atoms selected from fluorine, chlorine, bromine, and iodine. Examples of such groups include chloromethyl, bromoethyl, trifluoromethyl, and the like.

The term "aryl" when used alone means a homocyclic aromatic radical whether or not fused. Preferred aryl groups include phenyl, naphthyl, biphenyl, phenanthrenyl, naphthacenyl, and the like.

The term "substituted aryl" denotes an aryl group substituted with one, two, or three substituents chosen from halogen, hydroxy, protected hydroxy, cyano, nitro, $C_1$–$C_{10}$ alkyl, $C_1$–$C_{10}$ alkoxy, trifluoromethyl, amino, aminomethyl, and the like. Examples of such groups are 4-chlorophenyl, 2-methylphenyl, 3-methyl-4-hydroxyphenyl, and 3-ethoxyphenyl.

The term "arylalkyl" means one, two or three aryl groups having the number of carbon atoms designated, appended to an alkyl radical having the number of carbon atoms designated. A typical arylalkyl group is the benzyl group.

The term "alkenyl" as used herein refers to a monovalent straight or branched chain radical of from two to six carbon atoms containing a carbon double bond including, but not limited to, 1-propenyl, 2-propenyl, 2-methyl-1-propenyl, 1-butenyl, 2-butenyl and the like.

The term "alkylene" as used herein refers to a divalent straight or branched chain group of from one to ten carbon atoms, including but not limited to, —CH$_2$—, —(CH$_2$)$_2$—, —(CH$_2$)$_3$—, —CH(CH$_3$)—, —CH(C$_2$H$_5$)—, —CH(CH$_3$)CH$_2$—, and the like.

The term "alkenylene" as used herein refers to a divalent straight or branched chain group of from two to ten carbon atoms containing a carbon-carbon double bond, including but not limited to, —CH=CH—, —C(CH$_3$)=CH—, CH=CH—CH$_2$—, —CH=C(CH$_3$)—CH$_2$—, —CH$_2$CH(CH=CH$_2$)CH$_2$, and the like.

The term "alkynylene" as used herein refers to a divalent straight or branched chain group of from two to ten carbon atoms containing a carbon-carbon triple bond, including but not limited to,

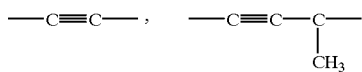

and the like.

The term "amidino" refers to the radical having the structural formula;

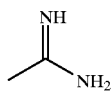

The term "basic radical" refers to an organic radical which is a proton acceptor. Illustrative basic radicals are amino and amidino. Basic radicals may also be formed from a ring nitrogen.

The term "basic group" refers to an organic group containing one or more basic radicals. A basic group may comprise only an basic radical.

The term "acid radical" refers to an organic radical which is a proton donor. Illustrative acid radicals include;

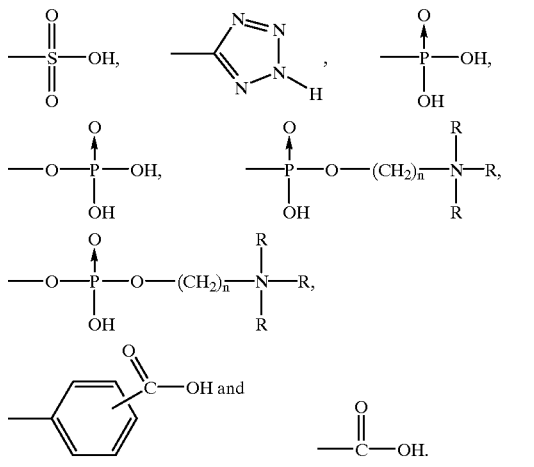

The term "acidic group" is an organic group containing one or more acid radicals. An acidic group may comprise only an acid radical.

The term "non-interfering substituent" refers to an organic radical which does not significantly reduce the therapeutic effectiveness of a compound.

Compounds of the Invention

This invention provides compounds of the general formula (I), or a pharmaceutically-acceptable salt, solvate or or prodrug thereof:

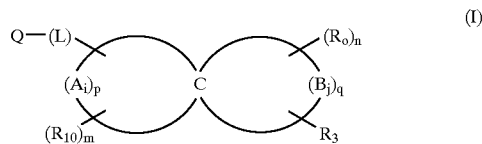

wherein;

the atoms $A_i$ and $B_j$ are independently selected from carbon, nitrogen, oxygen or sulfur, provided that at least one atom of $A_i$ is carbon, and at least one atom $B_j$ is carbon;

the rings of the spirobicycle formed by $A_i$ and $B_j$, respectively, may optionally be partly unsaturated;

p and q are independently numbers from 2 to 6;

m is a number from zero to p;

$R_{10}$ is the same or different and is a non-interfering substituent independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, sulfo, =O, or =S, with the proviso that only one $R_{10}$ may be =O or =S, if p is 2 or one or two $R_{10}$ may be =O or =S, if p is a number from 3 to 6;

n is the number from zero to q;

$R_O$ is the same or different and is a non-interfering substituent independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, sulfo, =O, or =S, with the proviso that only one $R_O$ may be =O or =S, if q is 2 or one or two $R_O$ may be =O or =S, if q is a number from 3 to 6;

the linking group —(L)— is a bond or a divalent substituted or unsubstituted chain of from 1 to 10 atoms selected from the group consisting of carbon, nitrogen, sulfur, and oxygen;

Q is a basic group containing one or more basic radicals; and $R_3$ is an acidic group containing one or more acid radicals.

Compounds of the Invention with Preferred Spiro Nuclei

A compound of formula (II), or a pharmaceutically-acceptable salt, solvate or prodrug thereof:

wherein Z is a spirocyclic nucleus selected from (A), (B), (C), or (D) below

Nucleus (A)

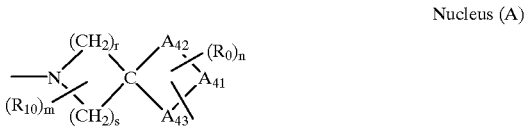

-continued

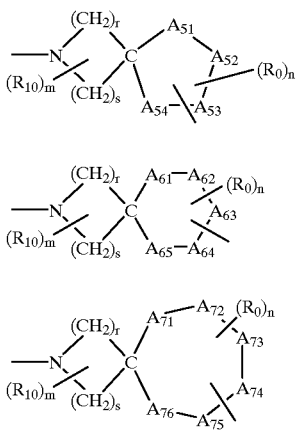

Nucleus (B)

Nucleus (C)

Nucleus (D)

wherein:

the group Q—(L)$_z$— is bound to the nitrogen containing ring of nuclei (A), (B), (C), or (D) and the group $R_3$ is bound to the ring formed by the groups $A_{41}$, $A_{42}$, $A_{43}$, $A_{51}$, $A_{52}$, $A_{53}$, $A_{54}$, $A_{61}$, $A_{62}$, $A_{63}$, $A_{64}$, $A_{65}$, $A_{71}$, $A_{72}$, $A_{73}$, $A_{74}$, $A_{75}$, or $A_{76}$; or the group $R_3$ is bound to the nitrogen containing ring and the group Q—(L)$_z$— is bound to the ring formed by the groups $A_{41}$, $A_{42}$, $A_{43}$, $A_{51}$, $A_{52}$, $A_{53}$, $A_{54}$, $A_{61}$, $A_{62}$, $A_{63}$, $A_{64}$, $A_{65}$, $A_{71}$, $A_{72}$, $A_{73}$, $A_{74}$, $A_{75}$, or $A_{76}$;

r and s are independently a number from zero to 5 with the proviso that not both r or s are 0 and (r+s) is not more than 6, and z is zero or one;

atoms $A_{41}$, $A_{42}$, $A_{43}$, $A_{51}$, $A_{52}$, $A_{53}$, $A_{54}$, $A_{61}$, $A_{62}$, $A_{63}$, $A_{64}$, $A_{65}$, $A_{71}$, $A_{72}$, $A_{73}$, $A_{74}$, $A_{75}$, or $A_{76}$ are independently selected from carbon, nitrogen, oxygen or sulfur, provided that at least one of said atoms is carbon;

the hydrogens of the nitrogen containing part of the spirocycle Z may be substituted by a number of m substituents $R_{10}$, wherein;

m is a number from zero to (r+s); and $R_{10}$ is the same or different and is a non-interfering substituent independently selected from alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, sulfo, =O, or =S, with the proviso that only one or two $R_{10}$ may be =O or =S;

n is a number from zero to 3 in Z of having nuclei (A), or a number from zero to 4 in Z having nuclei (B), a number from zero to 5 in Z having nuclei (C), or a number from zero to 6 in Z having nuclei (D);

$R_0$ is the same or different and is a non-interfering substituent independently selected from alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, sulfo, =O, or =S, with the proviso that only one or two $R_0$ may be =O or =S; and Q, L, and $R_3$ are as defined previously for the formula I compounds.

Representative Spirocyclic Nuclei

The spirocyclic compounds of the invention include spirocyclic nuclei selected from the group represented by the following structural formulae:

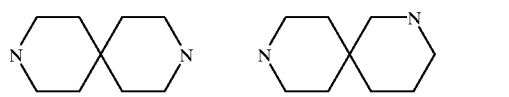
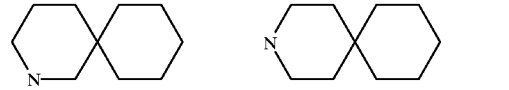
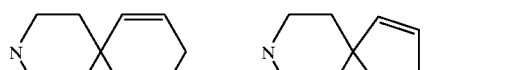
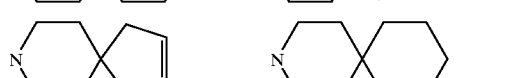
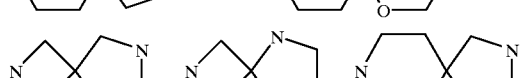
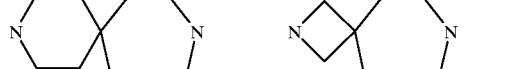
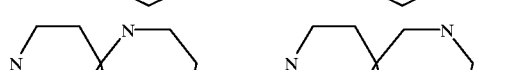
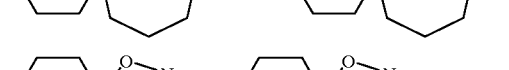
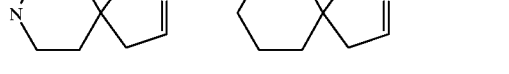

Representative oxo Substituted Spirocyclic Nuclei are as Follows

Oxo substituted spirocyclic compounds of the invention include spirocyclic nuclei selected from the group represented by the following structural formulae:

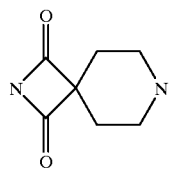
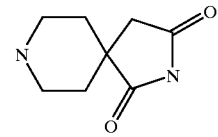

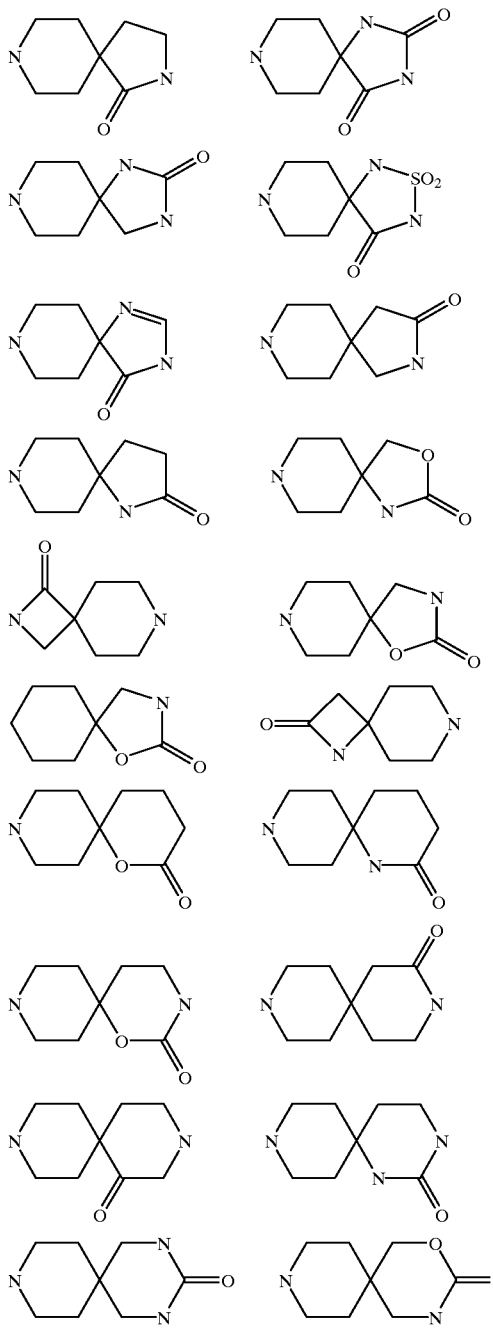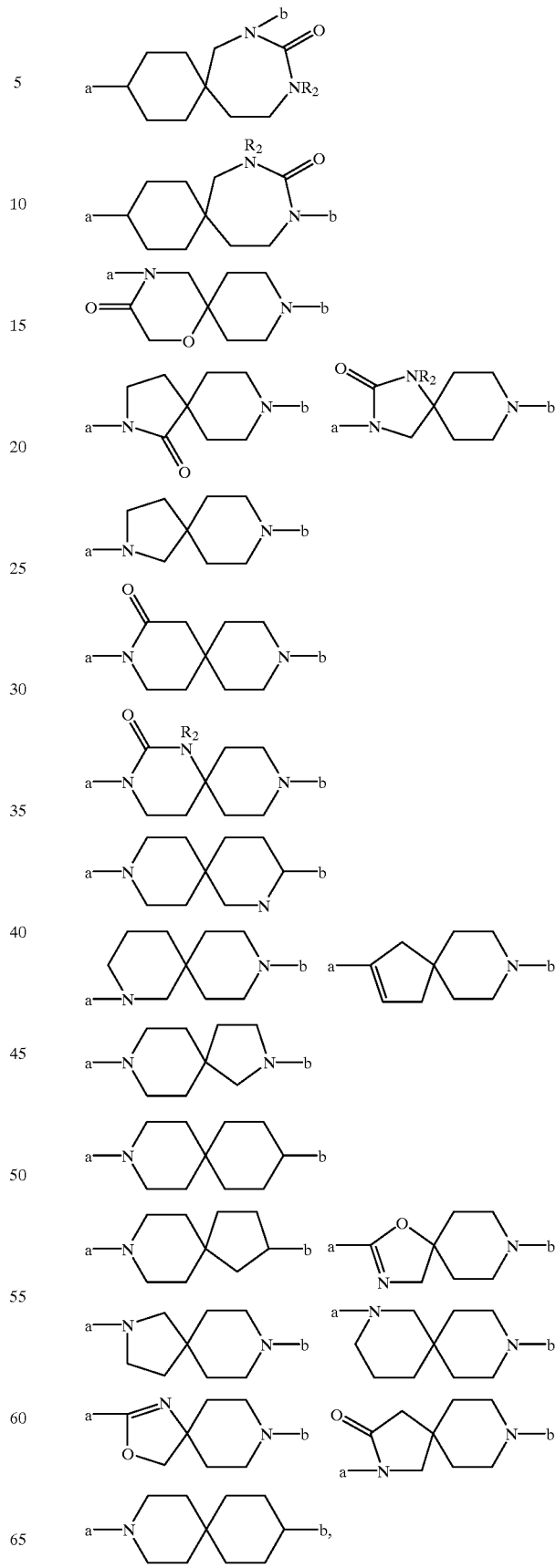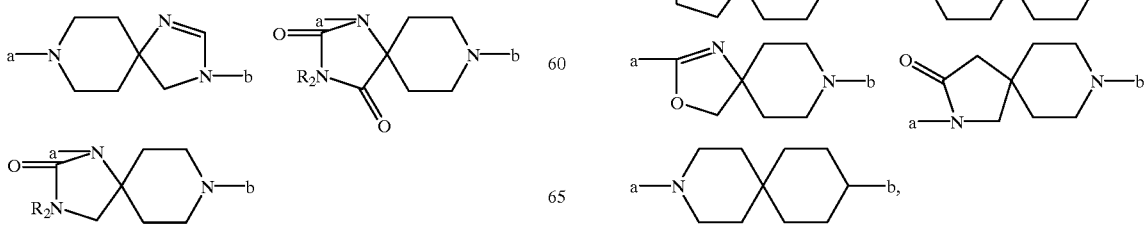
Preferred spirocyclic nuclei include the following nuclei:

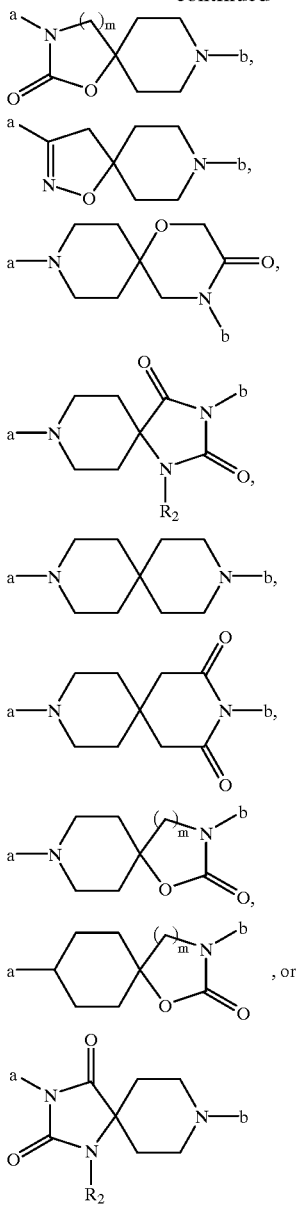
where m is one or two.
A group of more preferred spirocyclic nuclei includes the following groups:
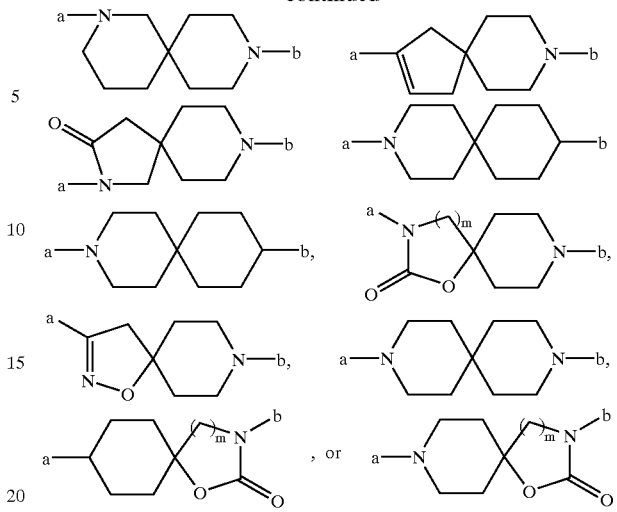
where m is one or two.
A second group of more preferred nuclei include the following:
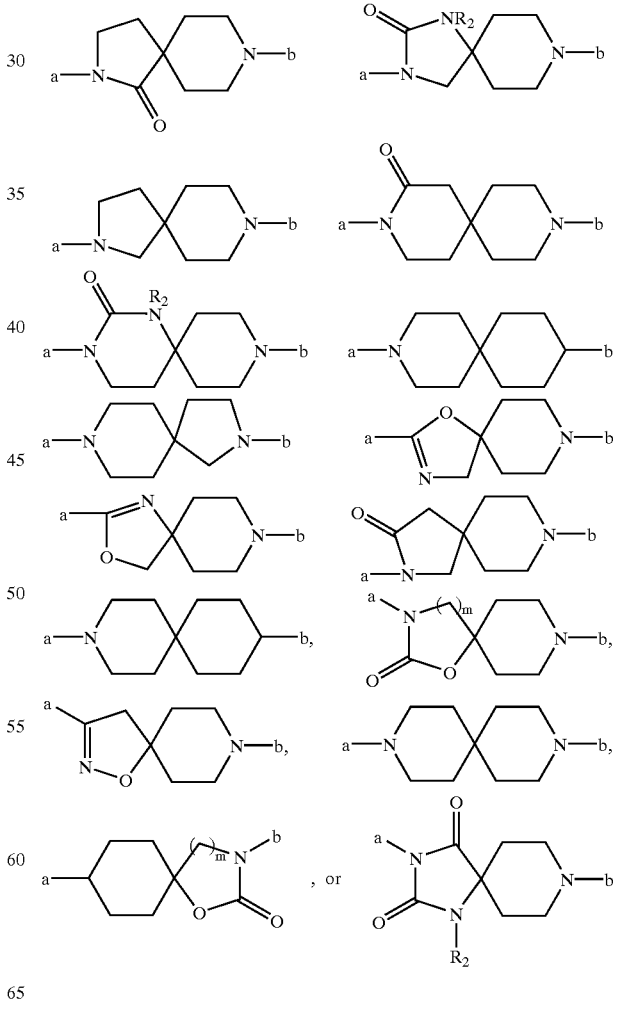
where m is one or two.

The most preferred spirocyclic nuclei include the following nuclei:

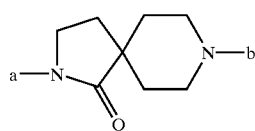 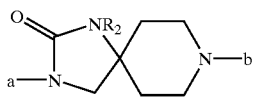

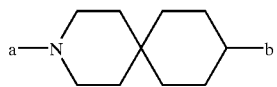 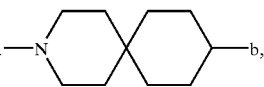

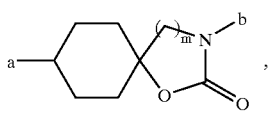 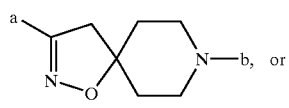, or

where m is one or two.

The Basic Substituent Q

The substituent Q of formulae (I) and (II) is a basic group. A basic group contains one or more basic radicals. Suitable basic radicals contain one or wore nitrogen atoms and include amino, imino, amidino, hydroxyamidino, N-alkylamidines, N,N'-dialkyamidines, N-arylamidines, aminomethyleneamino, iminomethylamino, guanidino, aminoguanidino, alkylamino, dialkylamino, trialkylamino, alkylideneamino, pyrrolyl, imidazolyl, pyrazolyl, pyridyl, pyrazinyl, pyrimidinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, amide, thioamide, benzamidino, pteridinyl, 4aH-carbozolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, hydroxyamidino, aminomethyleneamino, iminomethylamino, guanidino, alkylamino, dialkylamino, trialkylamino, tetrahydroisoquinoline, dihydrosioindole, alkylideneamino groups or a group represented by the formula;

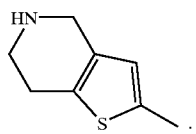

Preferred basic radicals are selected from amino, piperidyl, guanidino, hydroxyamidino, and amidino. The most preferred basic radicals are amidino, hydroxyamidino, and piperidyl represented by the formulae;

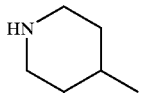 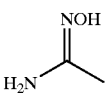 and 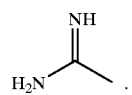.

The basic group and linker, Q—(L)$_Z$—, may have the form of a basic radical pendant on a cyclic ring as shown in formula IV below. The D of Formula (IV) ring may also have substituents $R_{20}$ which are selected from chlorine, fluorine or non-interfering organic radicals. Fluorine is preferred as a substituent on the D ring. The $R_{20}$ substituents may be t in number, where t is an integer from zero to the number of unsatisfied bonds in the D ring. The basic radical(s) attaches to the D ring in the manner shown in formula (IV) below:

(IV)

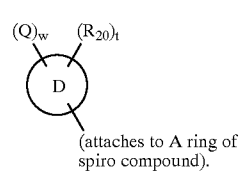

(attaches to A ring of spiro compound).

Suitable D rings are formed from a nucleus selected from the group consisting of; benzene, cycloheptadiene, cycloheptatriene, cycloheptane, cyclohexane, cyclohexene, cyclohexadiene, cycloheptene, cyclooctadiene, cyclooctane, cyclooctatetraene, cyclooctene, cyclopentane, cyclopentene, imidazole, isooxazole, morpholine, oxazole, piperazine, piperidine, pyrazine, pyrazole, pyridine, pyrimidine, pyrrole, pyrrolidine, pyrroline, tetrahydropyridine, tetrahydropyrimidine, 1H-tetrazole, thiazolidine, thiazole, thiopyran, 1,3,5-triazine, 1,2,3-triazole, 1,2,4-triazole, dihydrofuran, dihydropyran, dioxane, dioxepin, dioxolane, furan, oxocane, tetrahydrofuran, tetrahydropyran, thiophene, and tetrahydrothiophene.

An illustrative species of formula (IV) is the basic radical attached to a benzene ring as shown in formulae (V) and (VI) below:

(V)

and (VI)

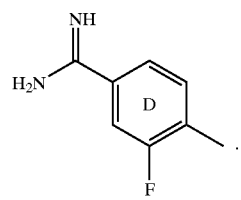

The preferred basics groups include the following groups:

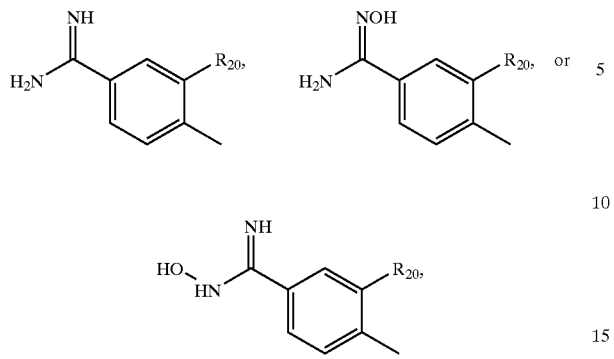

wherein $R_{20}$ is hydrogen or halogen.

The Acidic Substituent $R_3$

The substituent $R_3$ of formula (I) or (II) is an acidic group. An acidic group contains one or more acidic radicals. Suitable acidic radicals contain one or more proton donors, and include groups such as sulfonic acids, tetrazoles, phosphonic acids, carboxylic acids, and the like. The acidic radical may be bound to an aryl group, such as phenyl or substittued phenyl, or bound to alkyl chains, such as methylene. These groups may also be bound to the spirocyclic nucleus through alkyl chains having heteroatoms, suchs as S, O, or N, and amide (CONH) or carbonyl (CO) groups. The acidic substituent may also comprise an α-sulfonamido carboxylic acid group of the formula:

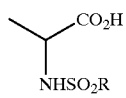

Preferred Spiro Comounds are as Follows

The formula II compounds, a preferred subset of the formula I spirocyclic compounds, which are preferred compounds of the invention include the following compounds, their pharmaceutically-acceptable salts, solvates, and prodrug derivatives, as follows:

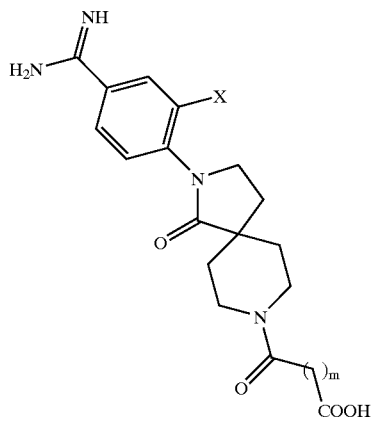

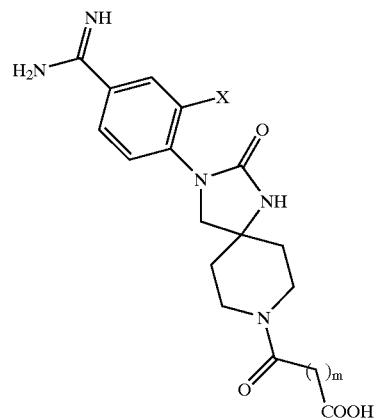

-continued

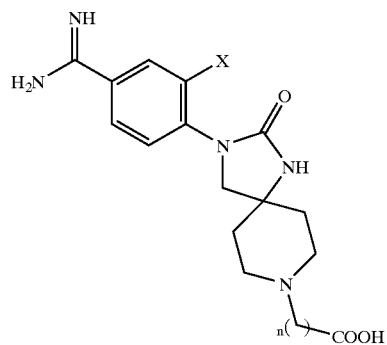

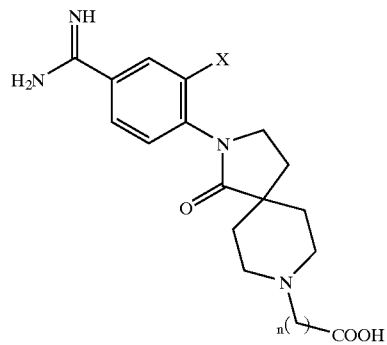

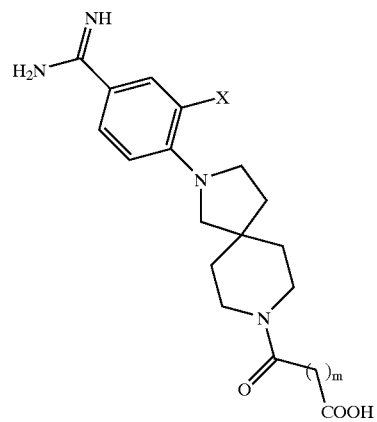

-continued
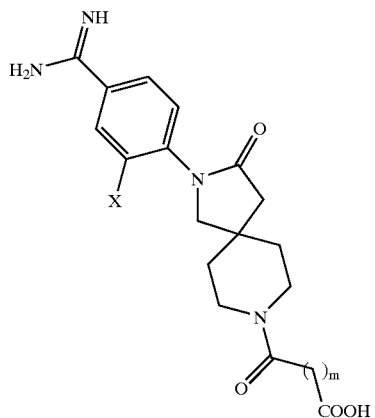
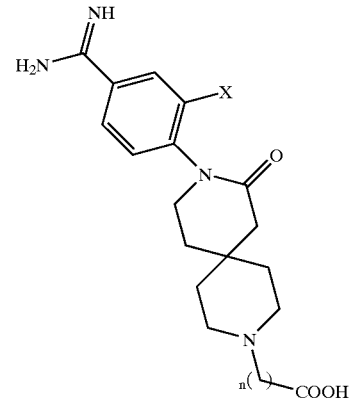
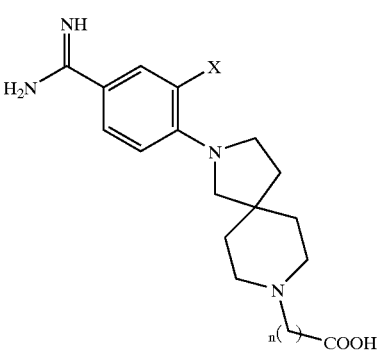
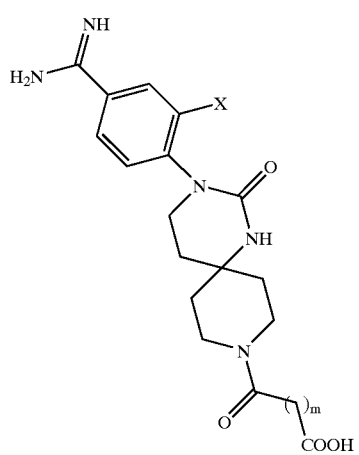
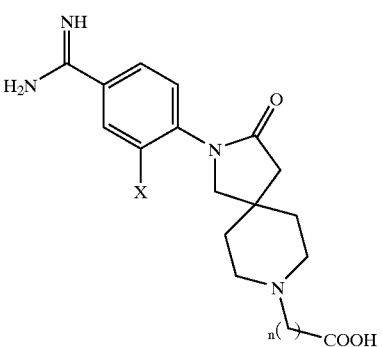
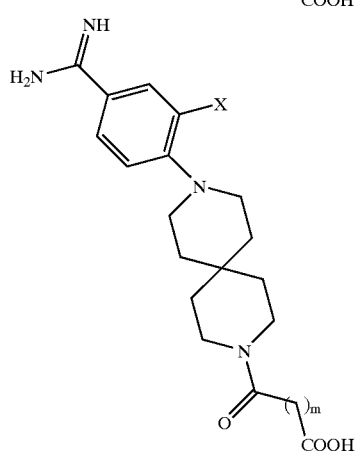
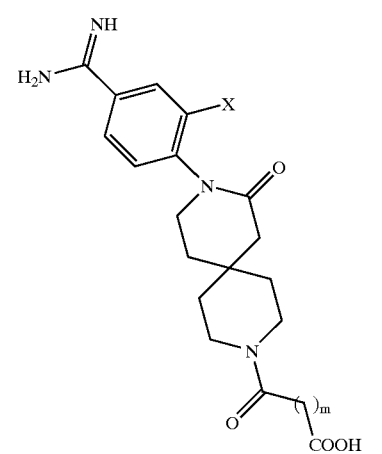

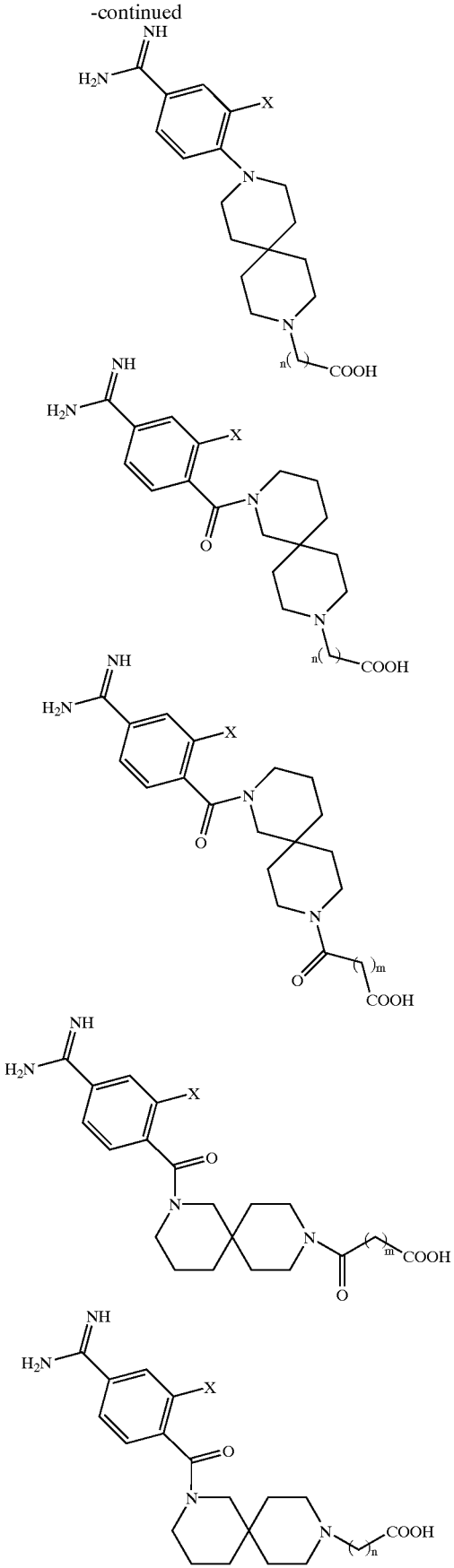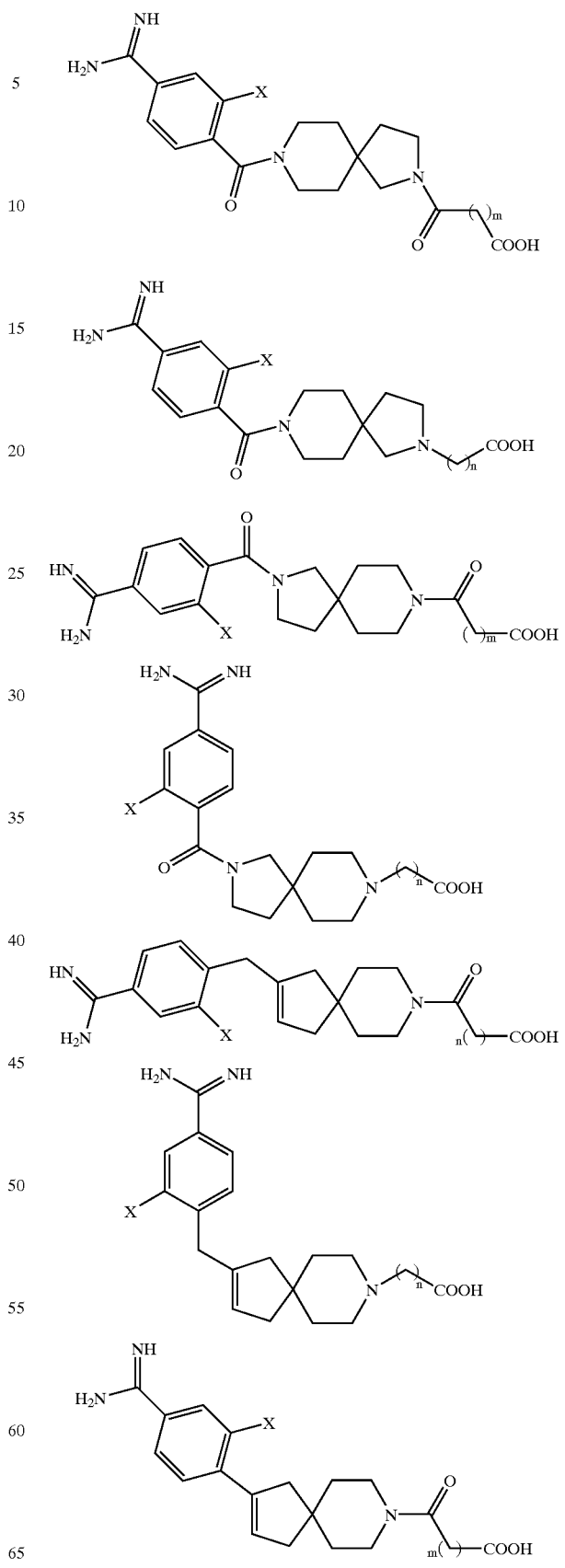

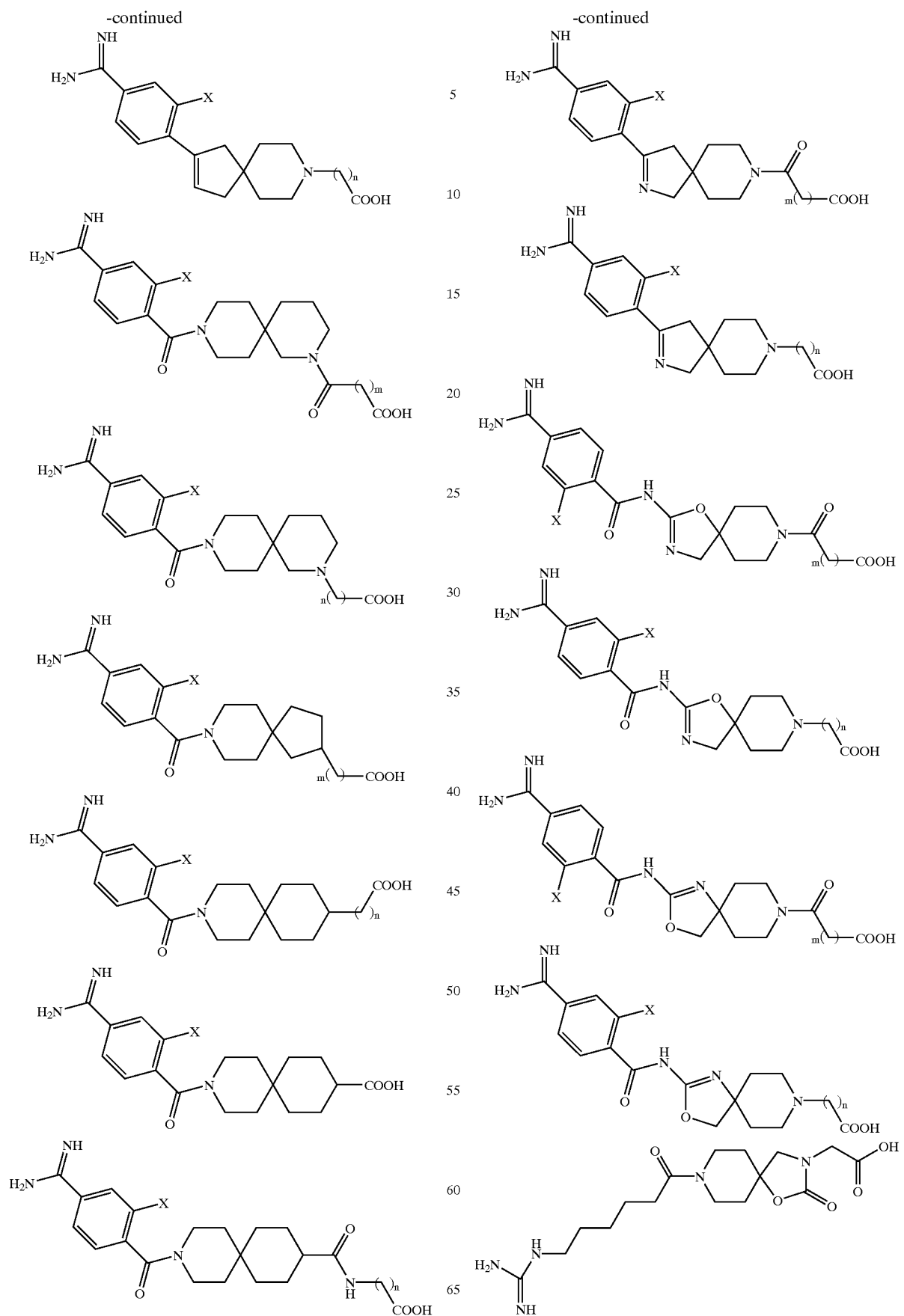

-continued
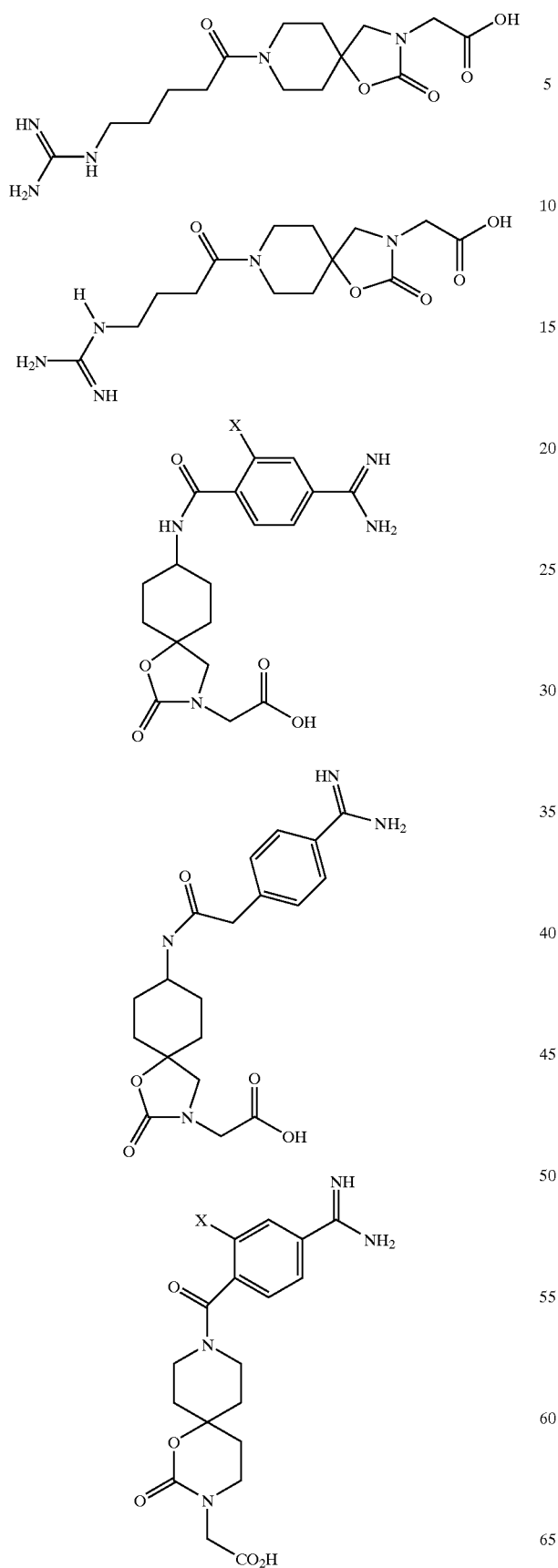
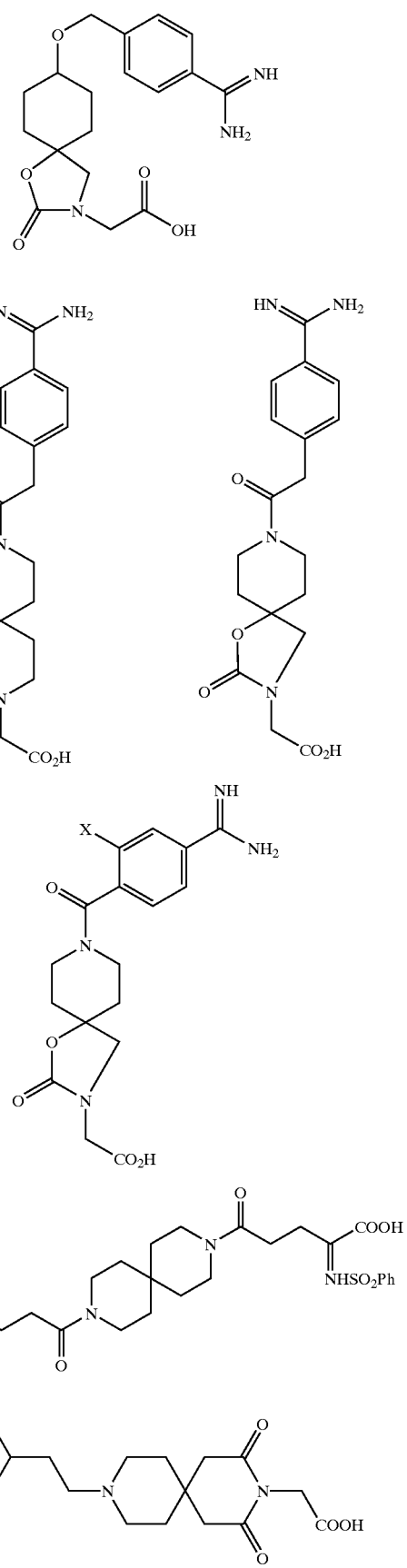

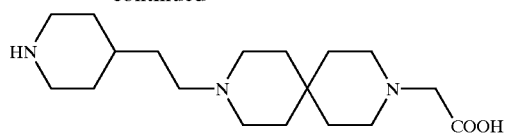
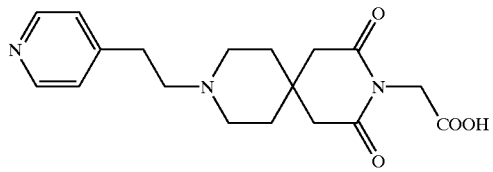
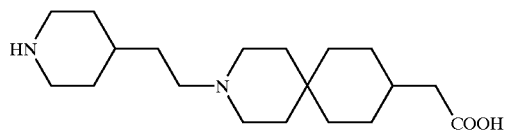
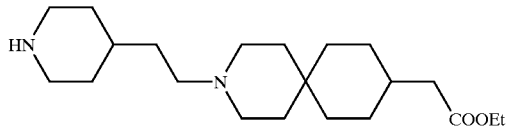
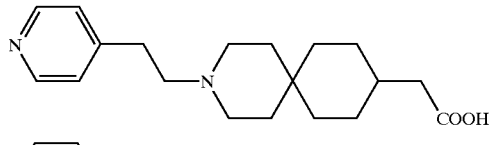
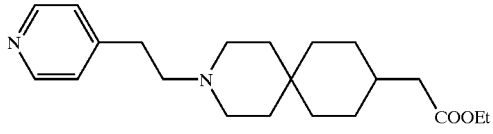
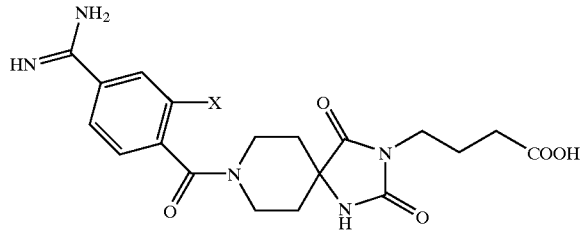
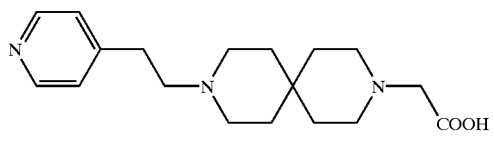
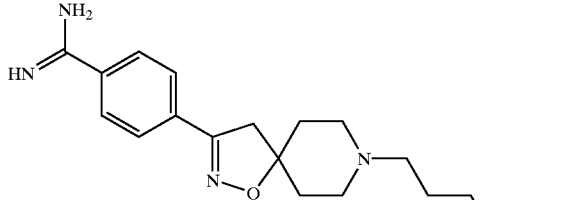
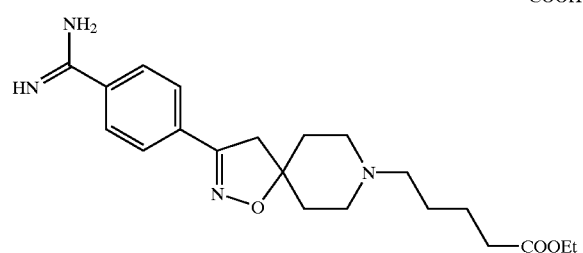
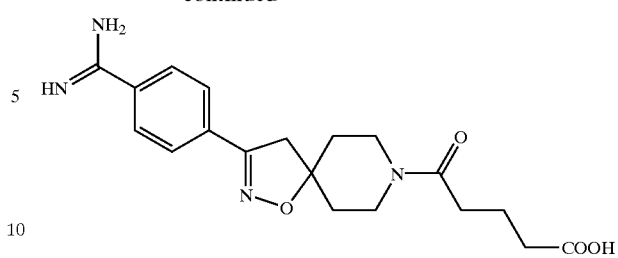
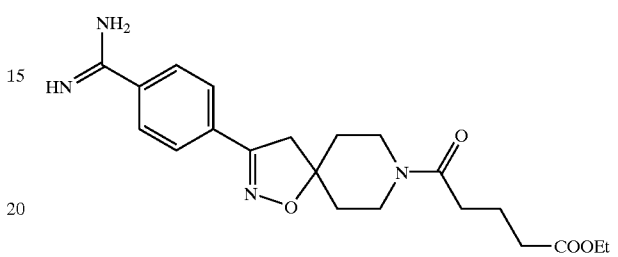
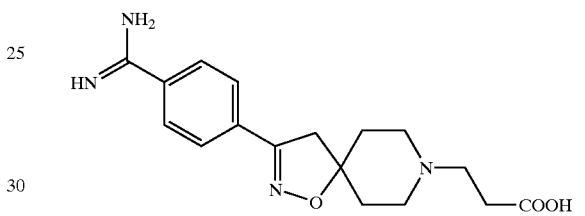
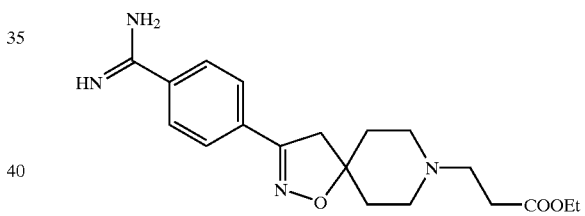
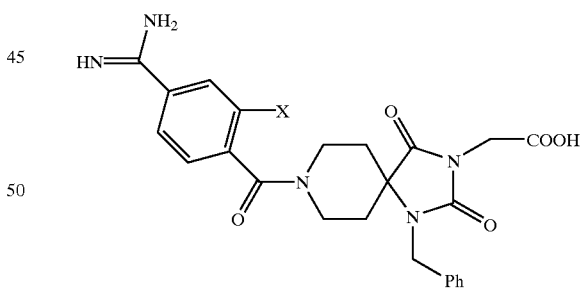
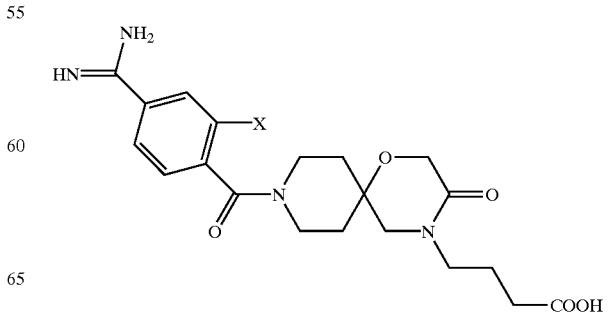

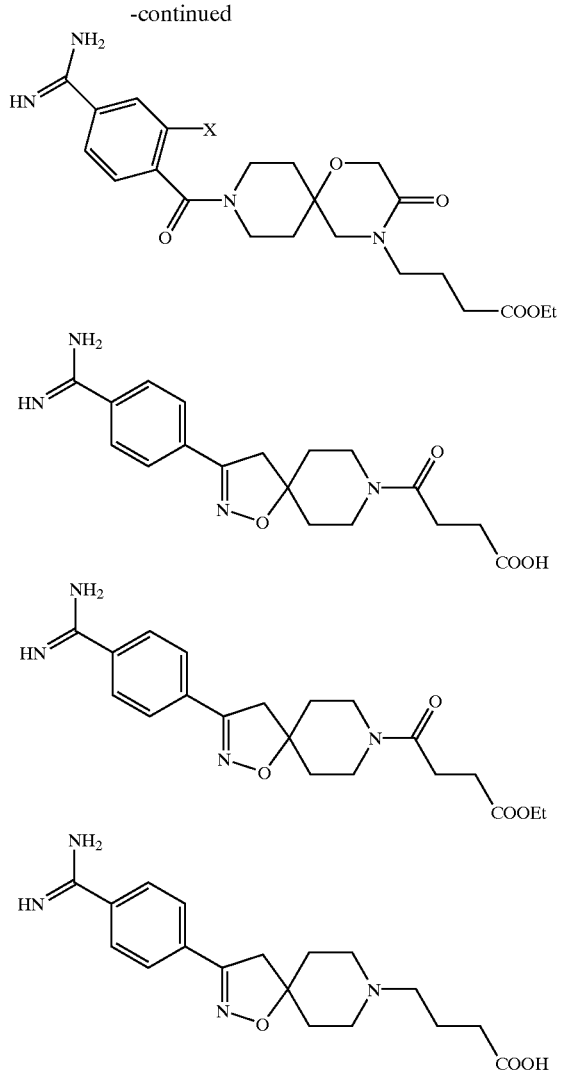
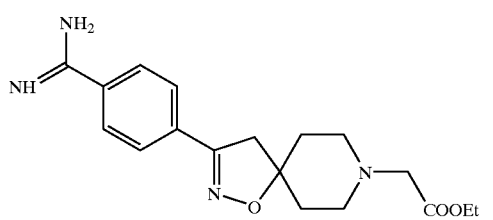
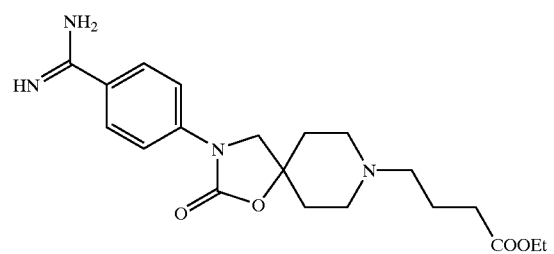
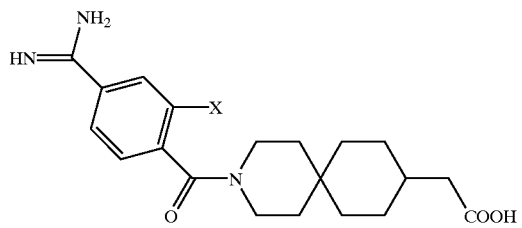
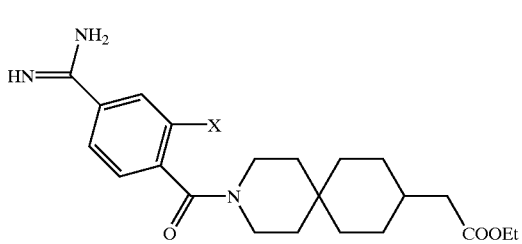
wherein X is F or H, m is zero to four, and n is one to four.
A more preferred subset of the formula I spirocyclic compounds include the following compounds, their pharmaceutically-acceptable salts, solvates, and prodrug derivatives, as follows:
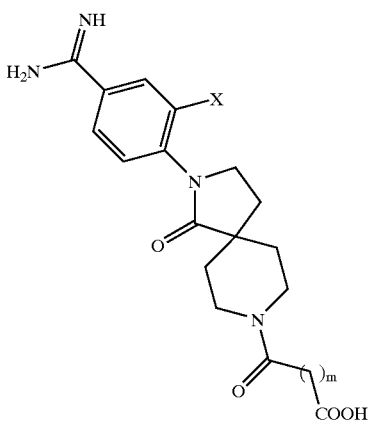

-continued
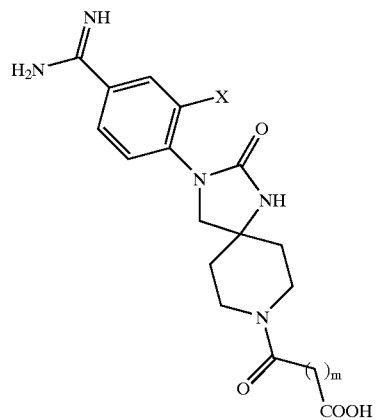
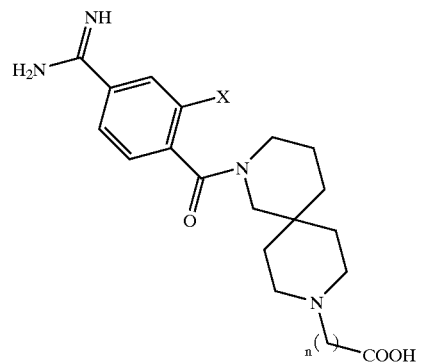
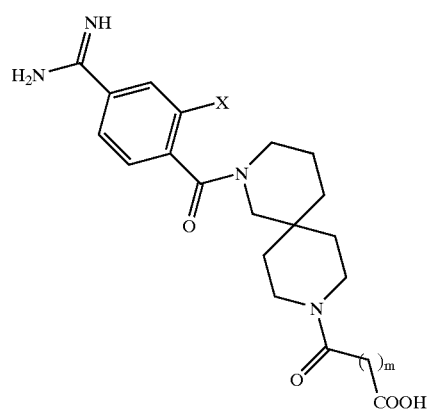
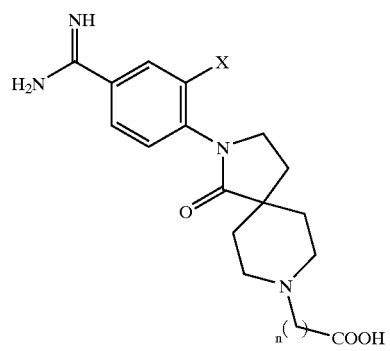
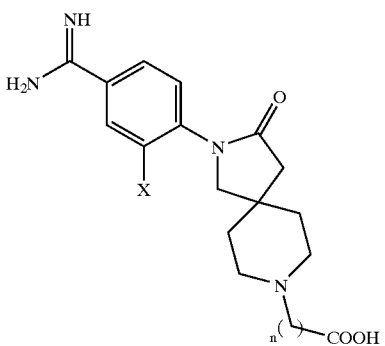
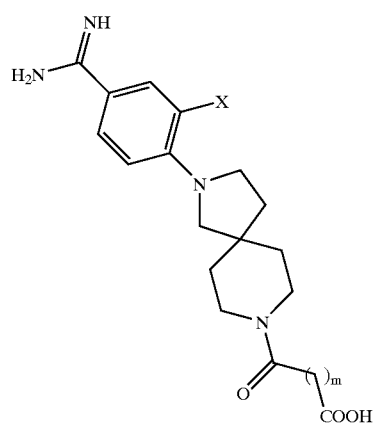
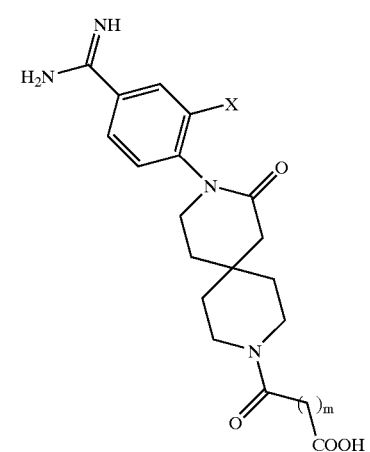

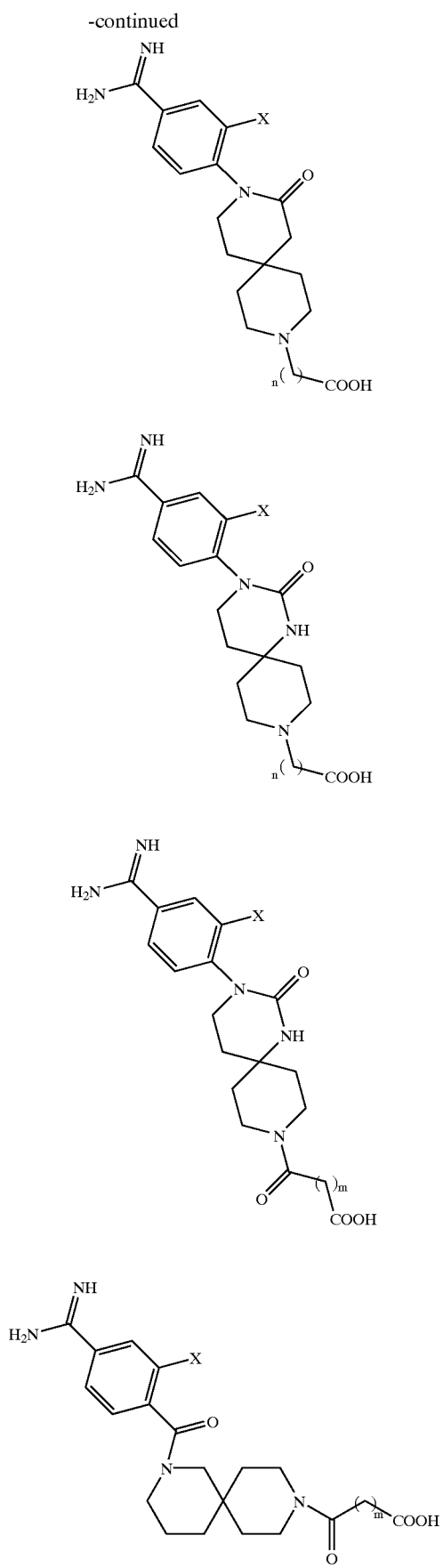
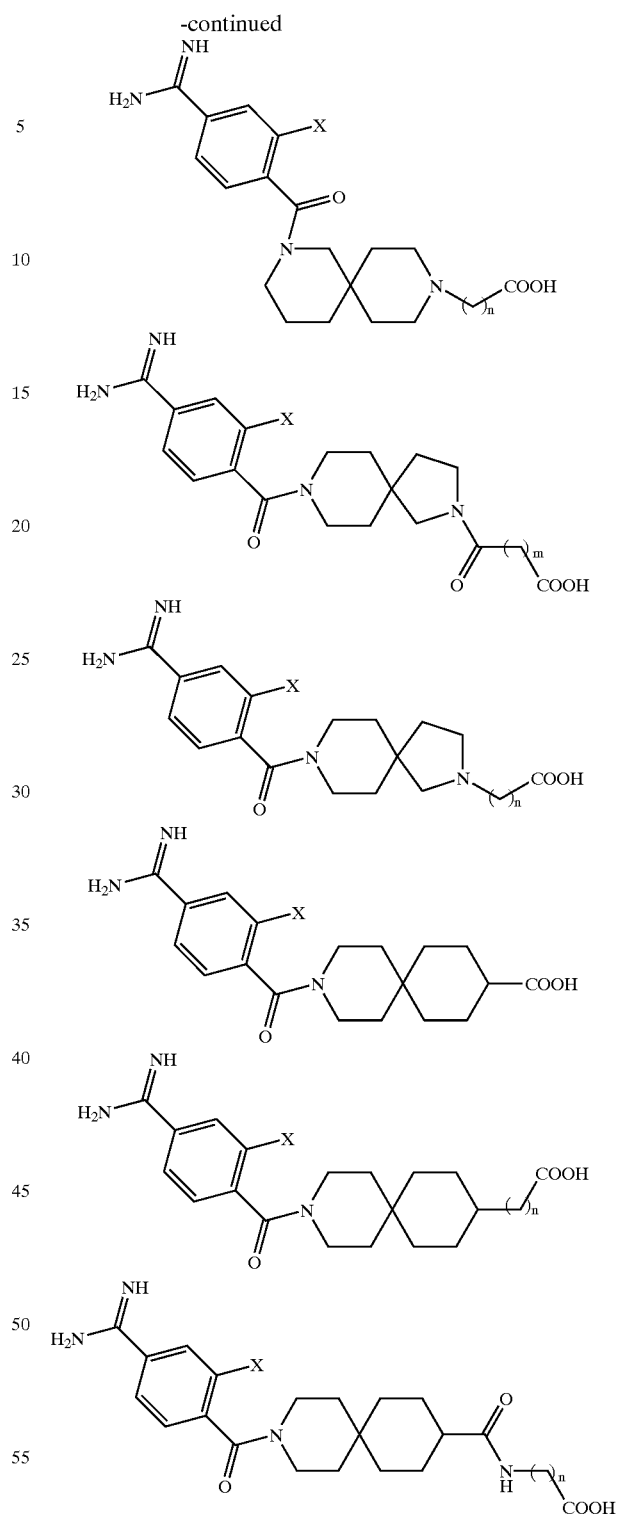
wherein X is F or H, m is zero to four, and n is one to four.
A second preferred subset of the formula I spirocyclic compounds include the following compounds, their pharmaceutically-acceptable salts, solvates, and prodrug derivatives, as follows:

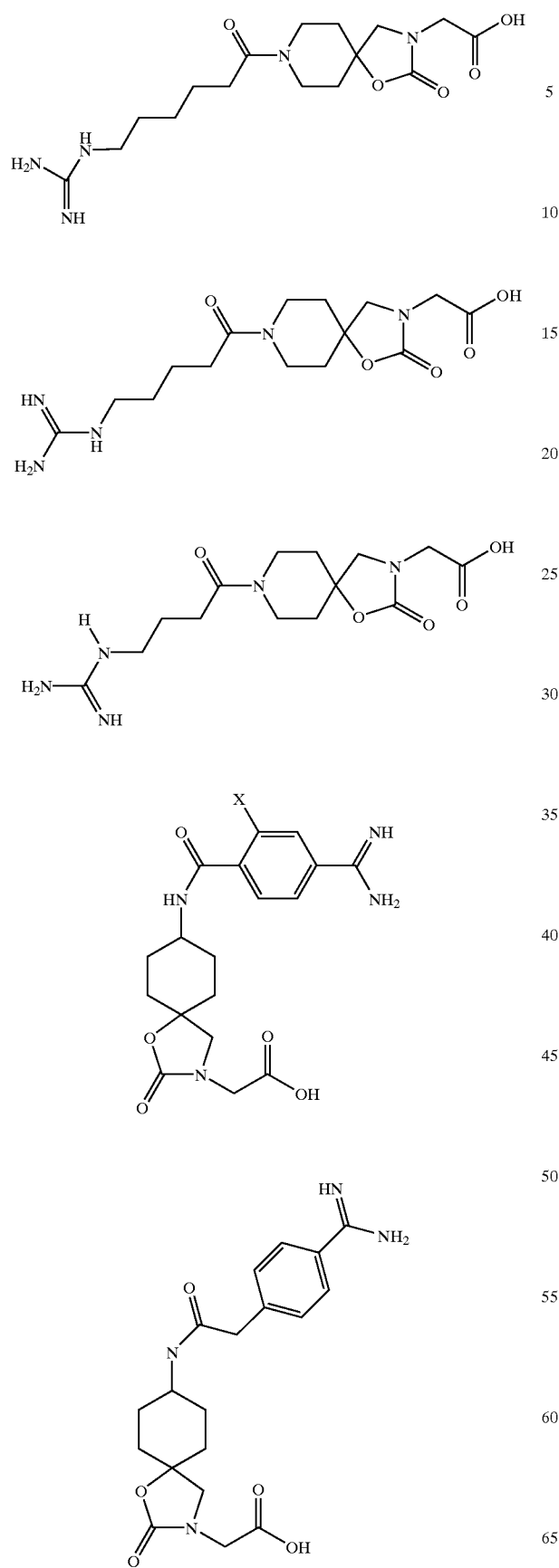
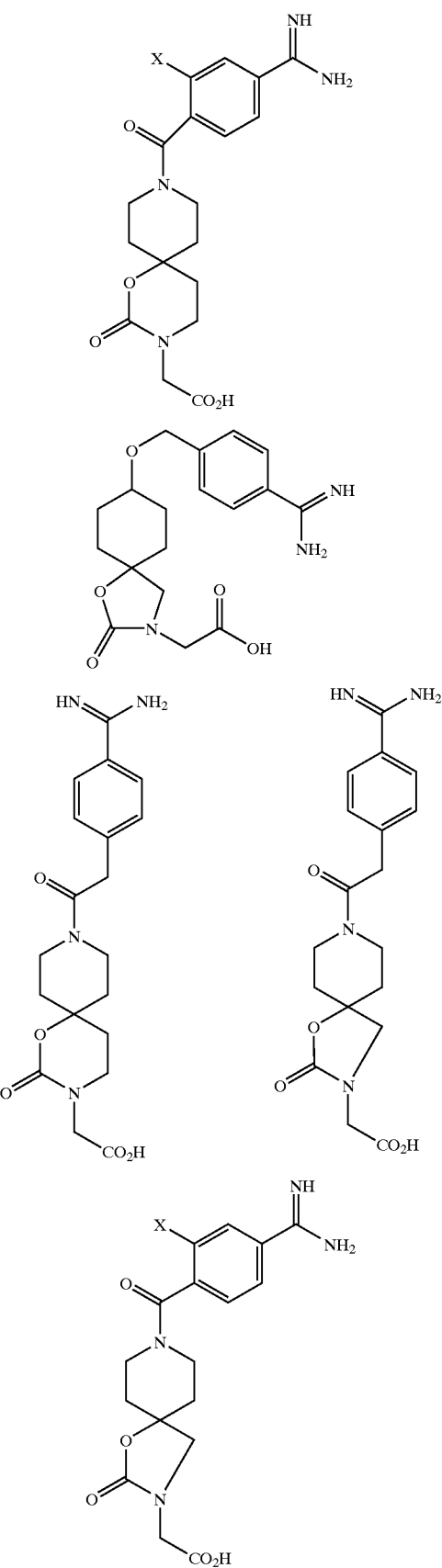

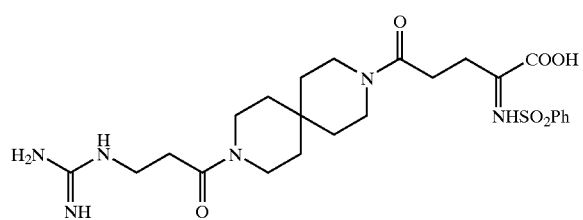
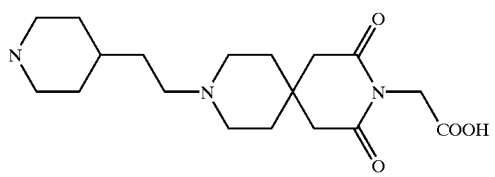
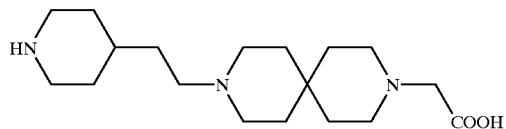
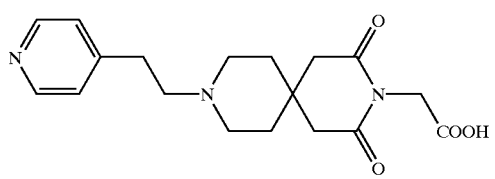
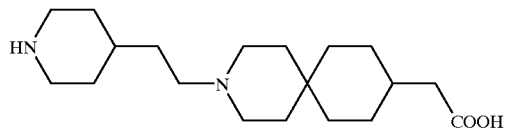
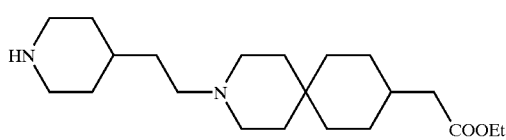
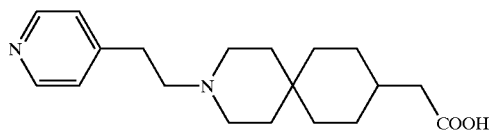
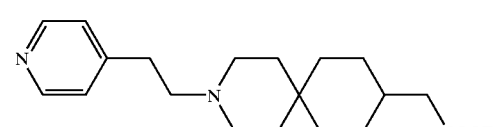
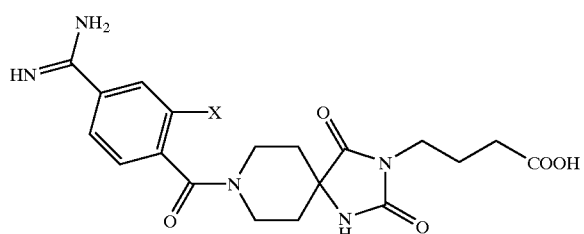
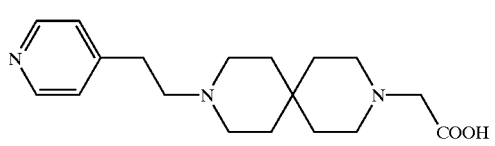
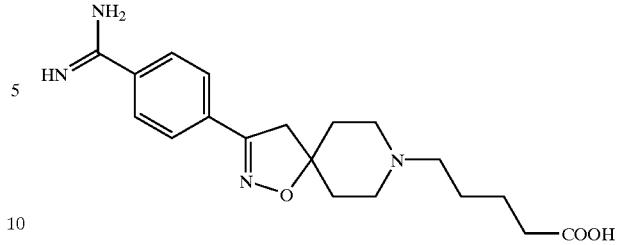
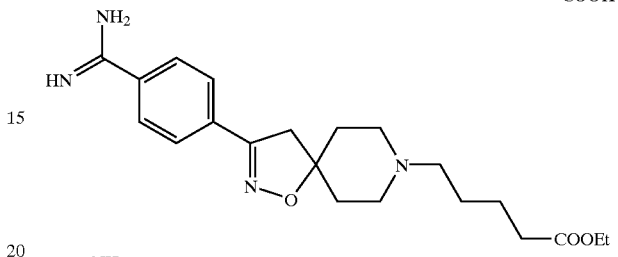
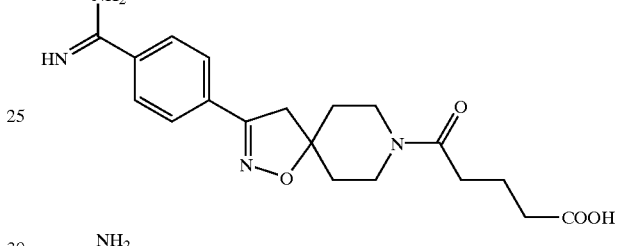
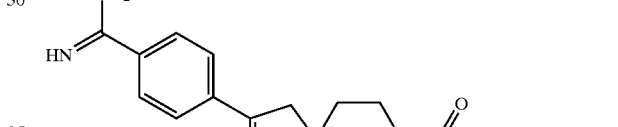
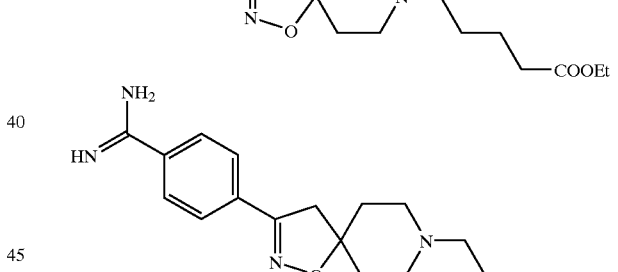
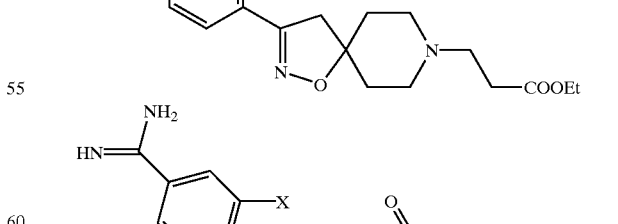
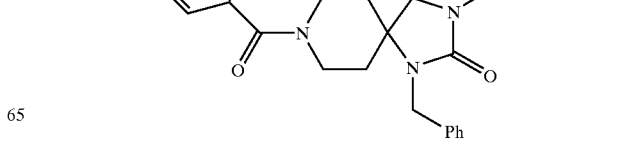

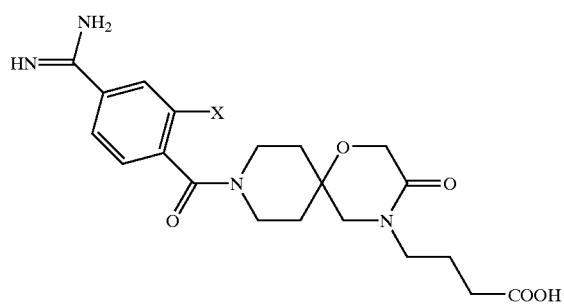
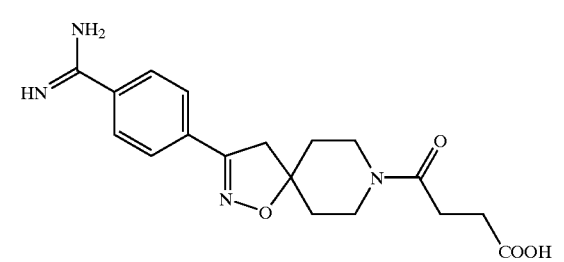
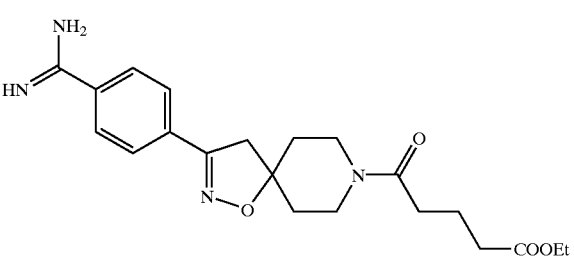
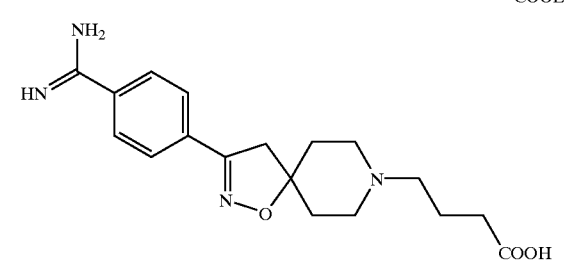
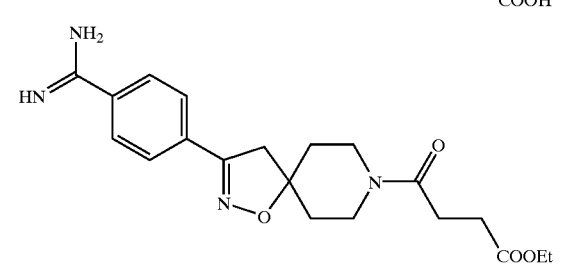
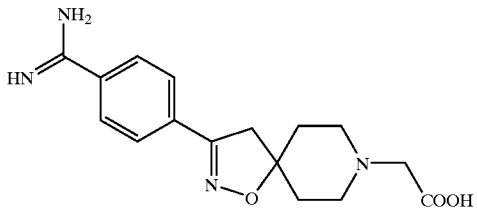
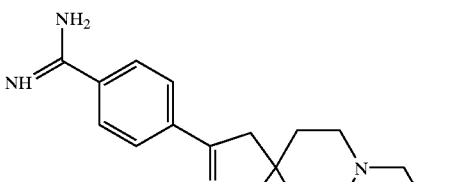
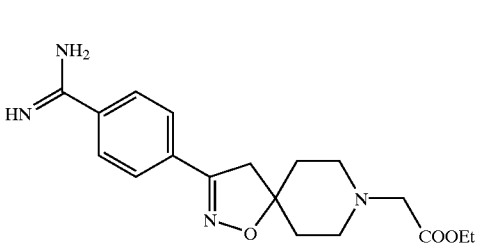
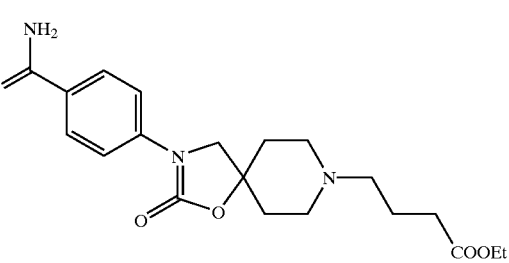
wherein X is F or H.
A second more preferred subset of the formula I spirocyclic compounds include the following compounds, their pharmaceutically-acceptable salts, solvates, and prodrug derivatives, as follows:

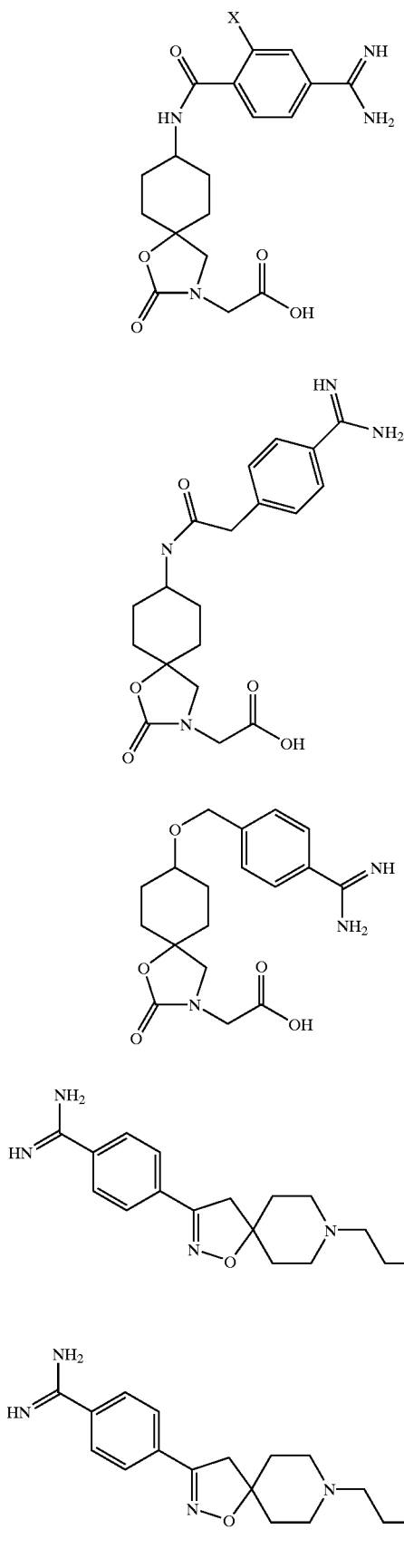
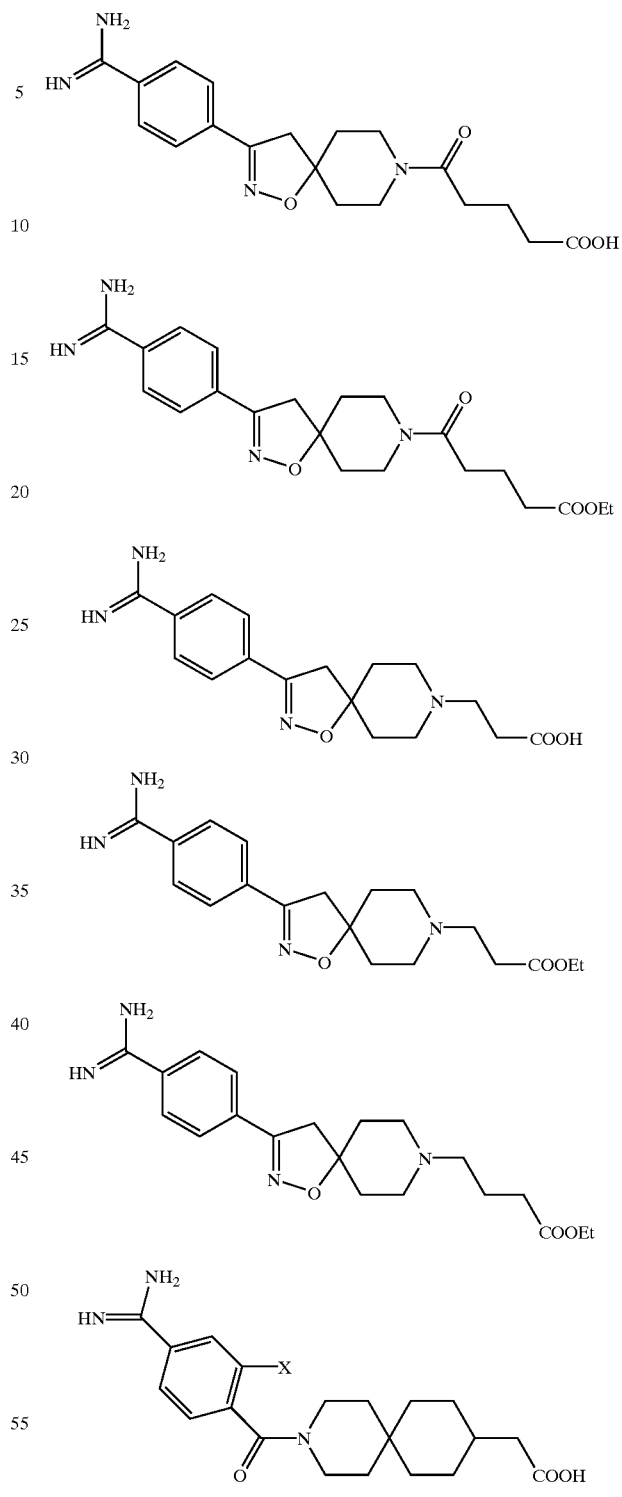
wherein X is F or H.
A most preferred subset of the formula I spirocyclic compounds include the following compounds, their pharmaceutically-acceptable salts, solvates, and prodrug derivatives, as follows:

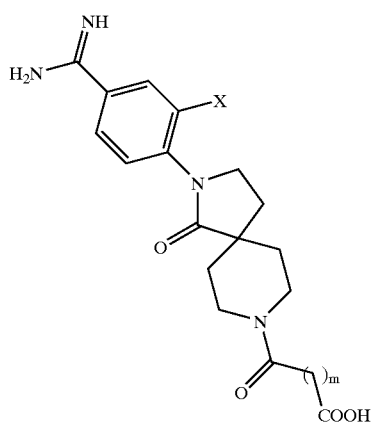
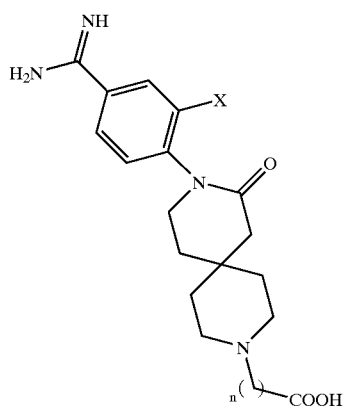
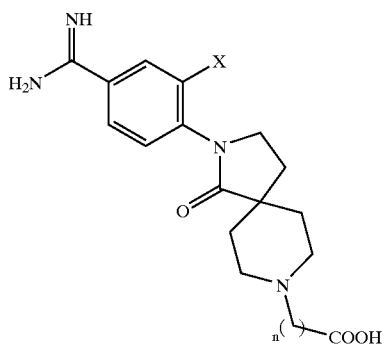
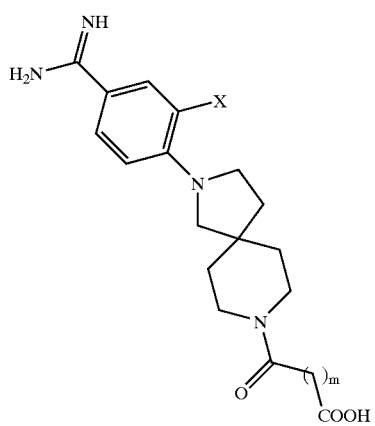
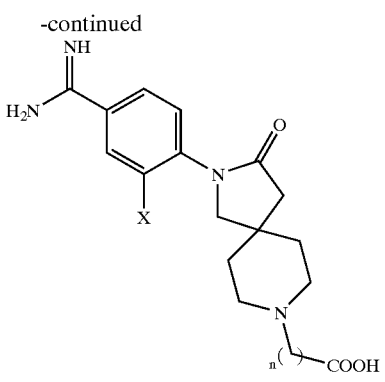
wherein X is F or H, m is zero to four, and n is one to four.
A second most preferred subset of the formula I spirocyclic compounds include the following compounds, their pharmaceutically-acceptable salts, solvates, and prodrug derivatives, as follows:
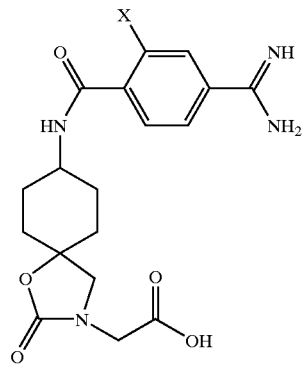
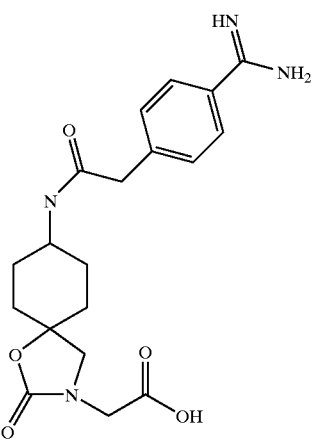
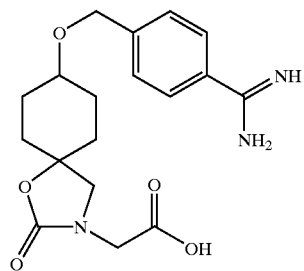

-continued

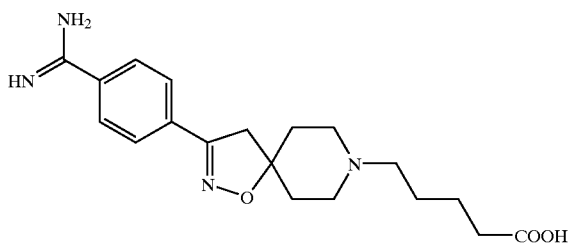
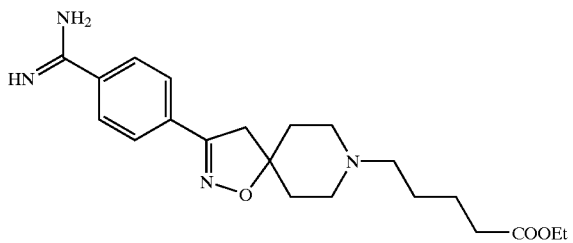
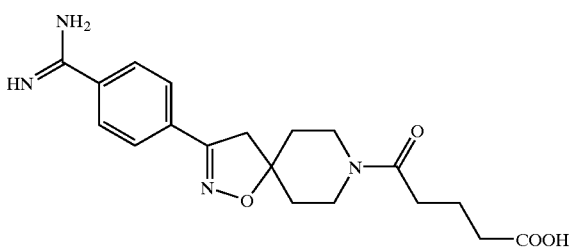
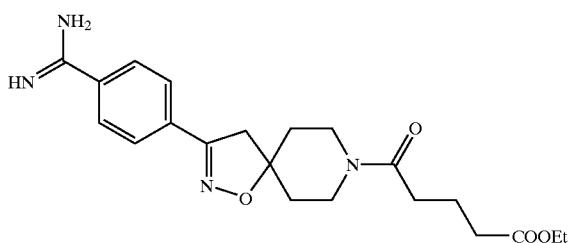
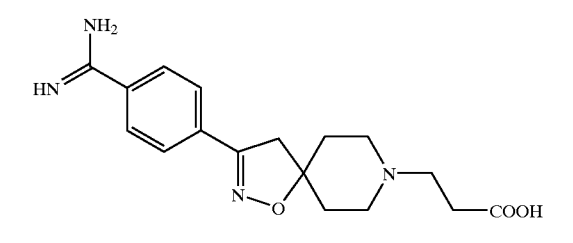
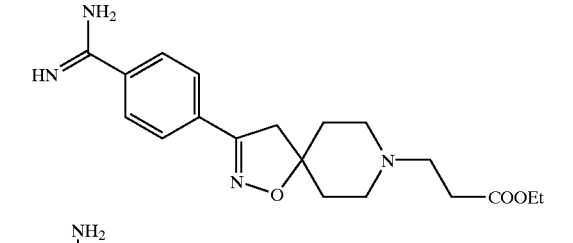
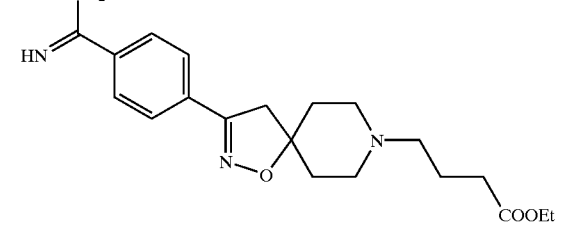

-continued

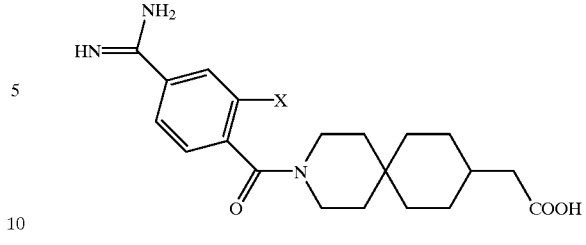

wherein X is F or H.

The compounds of the invention possess at least one acidic functional substituent (viz., $R_3$ of Formula I or II) and, as such, are capable of forming salts. Representative pharmaceutically-acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an anion exchange resin on the salt cycle.

Included within the definition of pharmaceutically-acceptable salts are the relatively non-toxic, inorganic and organic base addition salts of compounds of the present invention, for example, ammonium, quaternary ammonium, and amine actions, derived from nitrogenous bases of sufficient basicity to form salts with the compounds of this invention (see, for example, S. M. Berge, et. al., "Pharmaceutical Salts," J. Phar. Sci., 66: 1–19 (1977)).

The basic portion of the compounds of the invention (viz., part Q of formula I or II) may be reacted with suitable organic or inorganic acids to form salts of the invention. Representative salts include those selected from the group comprising; acetate, benzenesulfonate, benzoate, bicarbonate, bisulfate, bitartrate, borate, camsylate, carbonate, chloride, clavulanate, dihydrochloride, edetate, edisylate, estolate, esylate, fumarate, gluceptate, gluconate, glutamate, glycollylarsanllate, hexylresorcinate, hydrabamine, hydrobromide, hydrochloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

The compounds of the formula (I) or (II) can also be in the form of zwitterions, since they contain both acidic and basic functionality and are capable of self-protonation.

Certain compounds of the invention possess one or more chiral centers and may thus exist in optically active forms, or as mixtures of diastereomers. Likewise, when the compounds contain an alkenyl or alkenylene group there exists the possibility of cis- and trans-isomeric forms of the compounds. The R- and S-isomers and mixtures therof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrug Derivatives of Compounds of the Invention

Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendant on the compounds of this invention are preferred prodrugs. In some cases it is desirable to prepare double ester type prodrugs such as (acyloxy)alkyl esters or ((alkoxycarbonyl)oxy)alkyl esters.

Preferred are the $C_1$–$C_8$ alkyl, $C_2$–$C_8$ alkenyl, aryl, $C_7$–$C_{12}$ substituted aryl, and $C_7$–$C_{12}$ arylalkyl esters of the compounds of the invention (per formula I or II). Particularly preferred are the $C_1$–$C_4$ alkyl esters, for example, where the $R_3$ acidic group has been esterified to form a group represented by one of the following formulae:

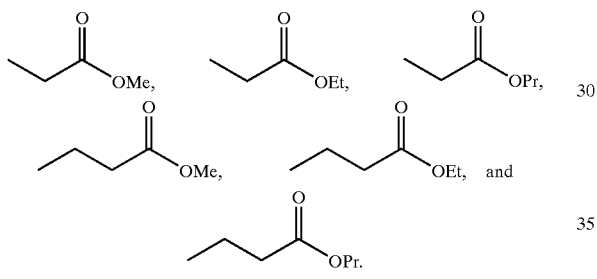

Acylated basic radicals which are part of basic group on the compounds of the invention have been found to significantly enhance bioavailability. Without being bound by any theory of operation, it is believed that lowering the basicity of basic group (Q) makes the compounds of this invention less subject to "food effect", that is, they have good availability in therapeutic administration to an animal without fasting.

Compounds of this invention may beneficially be dual prodrug derivatives. For example, the acidic group ($R_3$) may be reacted to form an ester and the basic group may additionally be reacted to form an acylated basic derivative. The prodrug derivatives of the compounds of this invention may be combined with other features herein taught to enhance bioavailability, for example, substitution of fluorine atoms on the basic benzamidine group.

Another highly preferred class of prodrugs of the invention are those formed by acylating the basic radicals present on the compounds of the invention. The acyl portion of the acylated basic radical has the general formula:

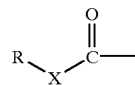

where R is $C_1$–$C_8$ alkyl, $C_2$–$C_8$ alkenyl, aryl, $C_7$–$C_{12}$ substituted aryl, and $C_7$–$C_{12}$ arylalkyl; and X is a bond, O, S, or N. Preferably R is $C_1$–$C_4$ alkyl and X is oxygen. For example, acylated basic radical prodrugs of the invention are prepared and illustrated in A, B, C, and D below:

A) acylation of amidine results in a prodrug derivative group:

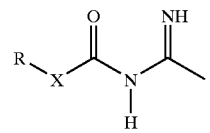

B) acylation of a cyclic amine such as piperidine results in a prodrug derivative group:

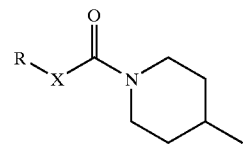

C) acylation of guanidine results in a prodrug derivative group:

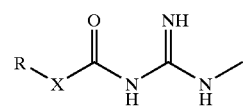

D) acylation of a primary amine results in a prodrug derivative group:

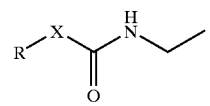

where, for A, B, C, and D above, R and X are as defined above for the acylated portion of the basic group.

Preparation of Spiro Compounds

The synthesis of spiro compounds covered by the invention is described in Scheme 1 thru Scheme 11, in which the following terms are used:

P means a general protective group for amines like benzyl, tert.-butoxycarbonyl, benzyloxycarbonyl, or ethoxycarbonyl.

X, when present, is a spacer typically consisting of a chain of up to three carbon atoms, e.g. methylene, dimethylene, or trimethylene.

Scheme Nomenclature

The substituent R is a non-interfering substituent illustrated by an alkyl group selected from ethyl, methyl, or tert.-butyl forming esters containing the group COOR, which are cleaved to the corresponding carboxylic acids (R=H).

Scheme 1

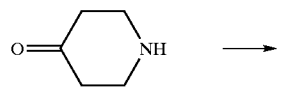

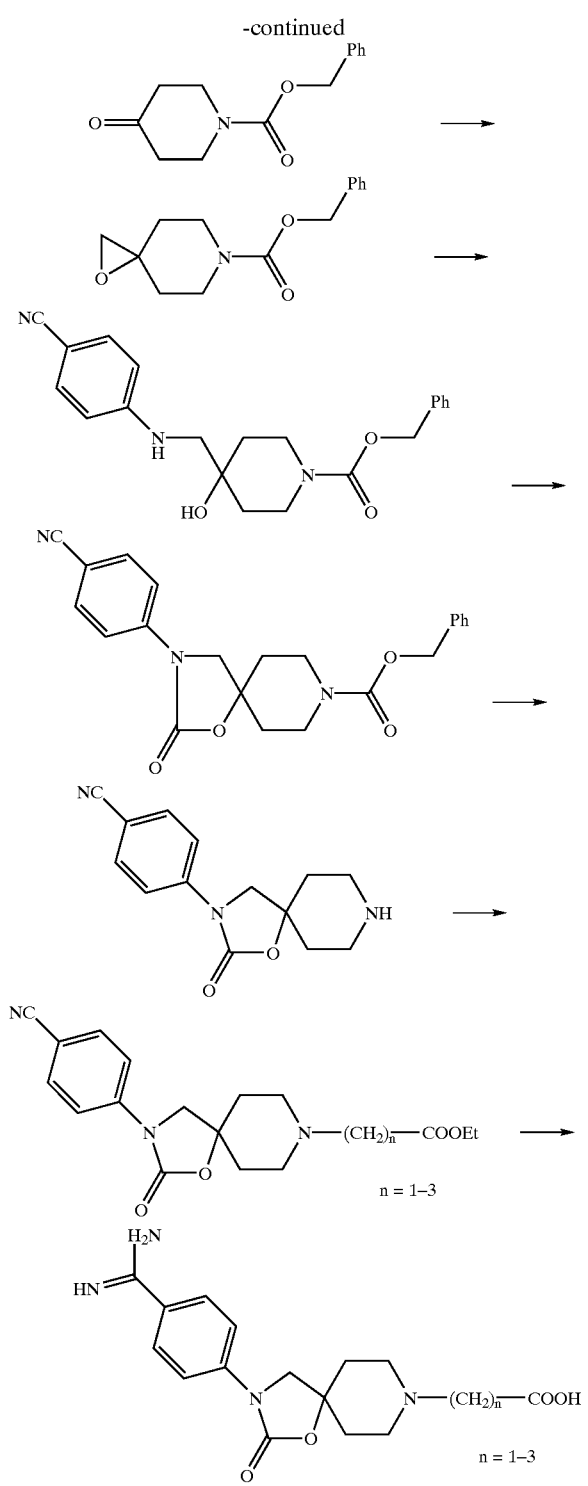
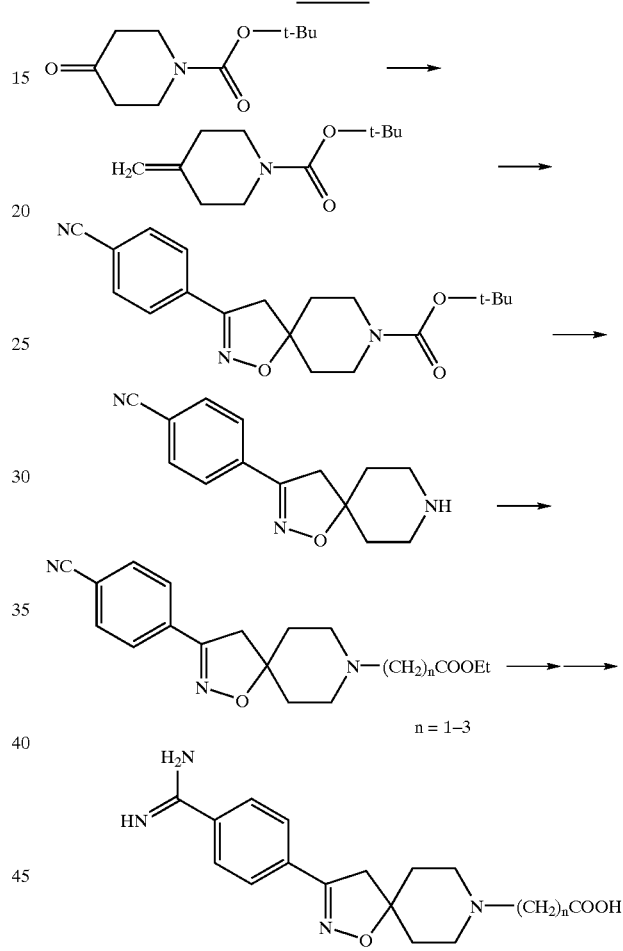

oxazolidinone is achieved with N,N'-carbonyl diimidazole, diethyl carbonate, or with phosgene. After removal of the protective group the piperidine is alkylated with an ω-halogenocarboxylate like ethyl bromoacetate or ethyl 4-bromobutanoate. Finally, the nitrile is converted to the amidine by reaction with ethanolic hydrochloric acid followed by treatment with ammonia, and the ethyl ester is cleaved under mild aqueous basic conditions to give the amidino carboxylic acid.

Scheme 1 describes the synthesis of 1-oxa-3,8-diaza-spiro [4.5]decan-2-ones (see J. M. Caroon, R. D. Clark, A. F. Kluge, J. T. Nelson, A. M. Strosberg, St. H. Unger, A. D. Michel, R. L. Whiting, J. Med. Chem. 1981, 24, 1320). 4-Piperidinone is N-protected, e.g. by reaction with benzyl chloroformate, and this compound is converted to the shown epoxide by addition of a methylene group using trimethylsulfoxonium iodide/sodium hydride in DMSO. The ring opening of the epoxide requires heating with an excess of 4-cyanoaniline, and the following formation of the spiro- The synthesis of 3-phenyl-1-oxa-2,8-diaza-spiro[4.5]dec-2-enes is outlined in Scheme 2. 4-Methylene-piperidines like 1-(tert.butoxycarbonyl)-4methylene-piperidine are prepared from the corresponding N-protected piperidinones by Wittig reaction. The five-membered ring is formed by addition of 4-cyanobenzonitrile oxide, which is generated in situ from 4-cyanobenzohydroximinoyl chloride with triethylamine (see K. C. Liu, B. R. Shelton, R. K. Howe, J. Org. Chem. 1980, 45, 3916; L. Fisera, F. Sauter, J. Fröhlich, Y. Feng, P. Ertl, K. Mereiter, Monatshefte Chem. 1994, 125, 553). The protective group is removed with trifluoroacetic acid followed by alkylation of the spiropiperidine and conversion of the nitrile to the amidine as described in the previous Scheme.

Scheme 3

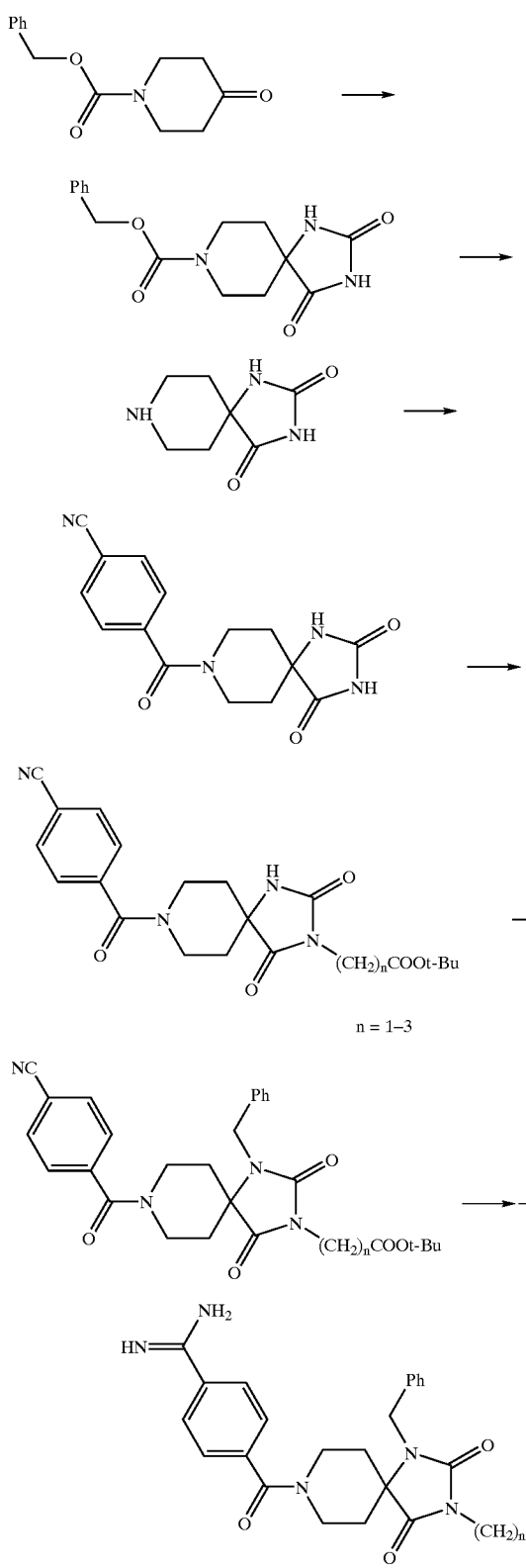

The synthesis of 2,4-dioxo-1,3,8-triaza-spiro[4.5]decane derivatives is described in Scheme 3. N-protected piperidin-4-ones like 1-benzyloxycarbonyl-piperidin-4-one are converted to the corresponding spirohydantoins by heating with a mixture of potassium cyanide and ammonium carbonate (see G. Winters, V. Aresi, G. Nathansohn, Farmaco, Ed. Sci. 1970, 25, 681). The protective group is removed by hydrogenation, and the piperidine is treated with 4-cyanobenzoyl chloride. Alkylation of this intermediate with ω-halogenoalkanoates gives the shown 3-substituted derivatives, and in a second alkylation step the nitrogen at position 1 may be alkylated with alkyl halides R'Hal, e.g. with benzyl bromide leading to 1-benzyl-2,4-dioxo-1,3,8-triaza-spiro[4.5]decanes (see O. O. Orazi, R. A. Corral, H. Schuttenberg, J. Chem. Soc., Perkin Trans. I, 1974, 219). The preferred method for conversion of the benzonitrile to an amidine employs the sequence of addition of hydrogen sulfide, alkylation of the intermediate primary thioamide with methyl iodide, heating with ammonium acetate, and purification of the crude amidine after protection with tert.-butoxycarbonyl. In a final step the protective group is removed with trifluoroacetic acid. If the acidic side chain has been masked by an tert.-butyl ester this one is also cleaved under these conditions.

Scheme 4

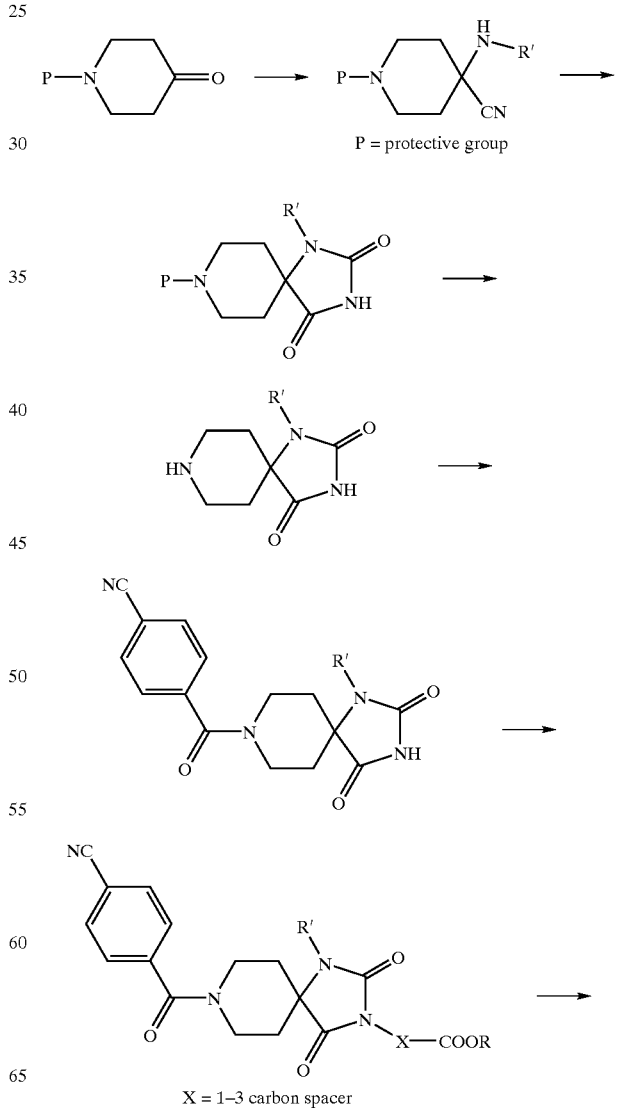

-continued

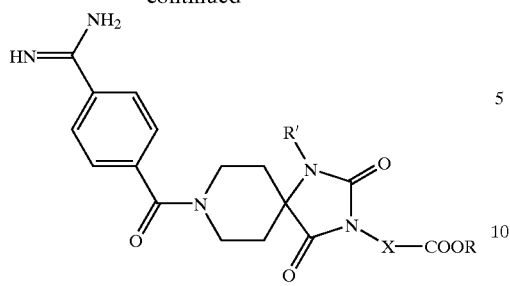

-continued

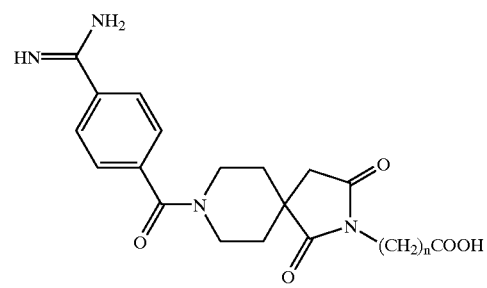

In an alternative sequence 1-substituted 2,4-dioxo-1,3,8-triaza-spiro[4.5]decane derivatives may be prepared as shown in Scheme 4 (see G. M. Carrera, Jr., D. S. Garvey, J. Heterocyclic Chem. 1992, 29, 847). The piperidone is treated with a mixture of potassium cyanide and a primary amine like benzyl amine. The intermediate 4-amino-4-cyanopiperidine is hydrolyzed followed by ring closure with potassium cyanate. The following steps including the alkylation of the nitrogen in position 3 with ω-halogenoalkanoates and formation of the amidine is carried out as described in Scheme 4.

Scheme 5A describes the synthesis of 1,3-dioxo-2,8-diaza-spiro[4.5]decane derivatives (see E. Jucker, R. Süeβ Arch. Pharm. 1961, 294/66, 210; Helv. Chim. Acta 1977, 49, 1135; Y. Ishihara, H. Yukimasa, M. Miyamoto, G. Goto, Chem. Pharm. Bull. 1992, 40, 1177). The shown 2-cyanoacrylate is formed by Knoevenagel condensation between N-protected piperidin-4-ones like N-benzylpiperidinone and ethyl cyanoacetate. It is heated with potassium cyanide in ethanol/water followed by hydrolysis with hydrochloric acid. The diacid may be purified by reesterification followed by another hydrolysis step of the substituted diethyl succinate, and the succinic acid is converted to the spiro succinic anhydride with dehydration reagents like dicyclohexylcarbondiimide (DCC) or acetanhydride. It is treated in situ with ω-aminoalkanoates to give the spiroimides. After removal of the protective group the reaction with 4-cyanobenzoyl chloride, formation of the amidine and saponification of the ester are carried out as described before.

Scheme 5A

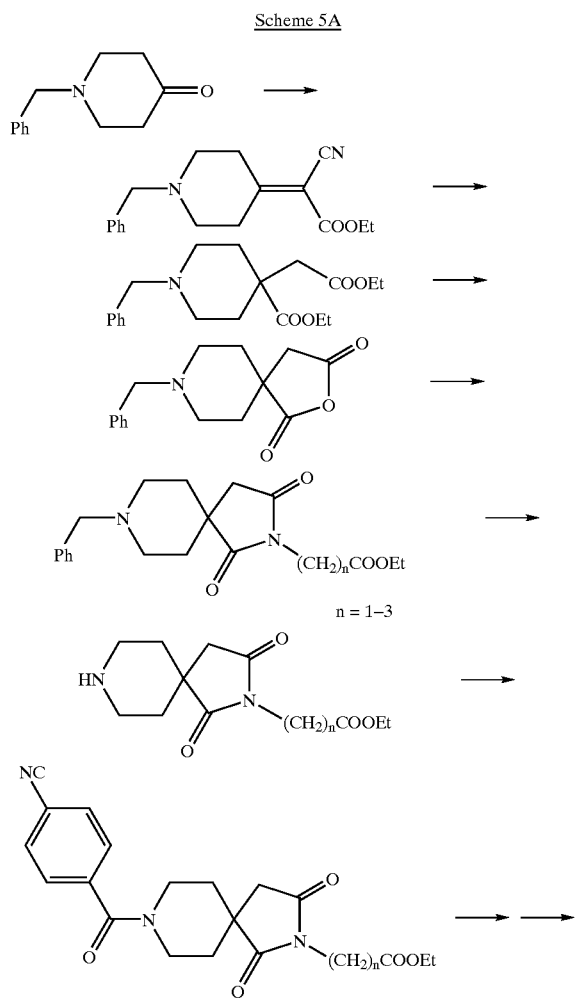

Scheme 5B

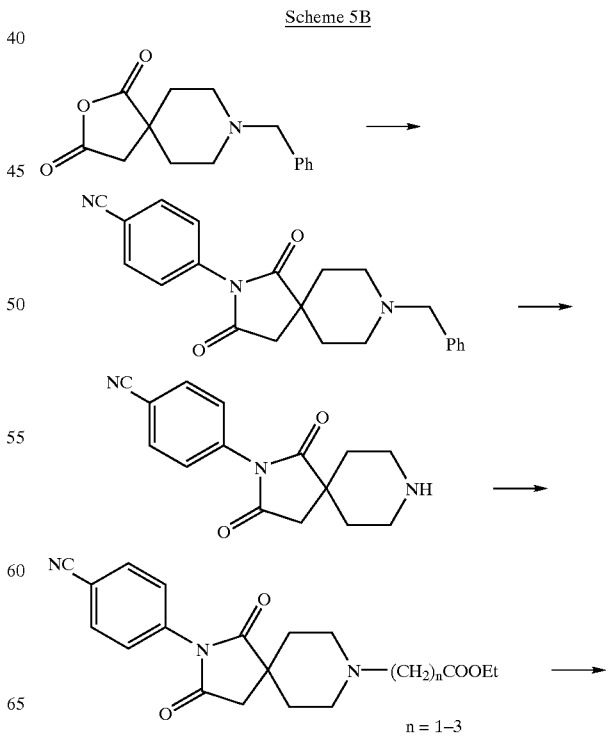

-continued

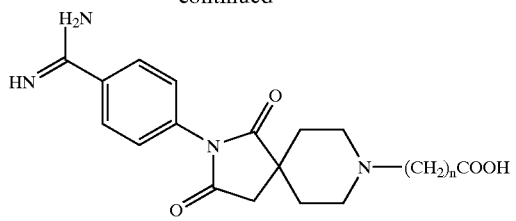

In a similar sequence 2-phenyl-1,3-dioxo-2,8-diaza-spiro [4.5]decanes are prepared. In contrast to Scheme 5A the intermediate succinic anhydride reacts with 4-aminobenzonitrile, and after deprotection of the spiropiperidine the intermediate is alkylated with ω-halogenoalkanoates. The final steps of the synthesis are carried out in the usual manner.

Scheme 6

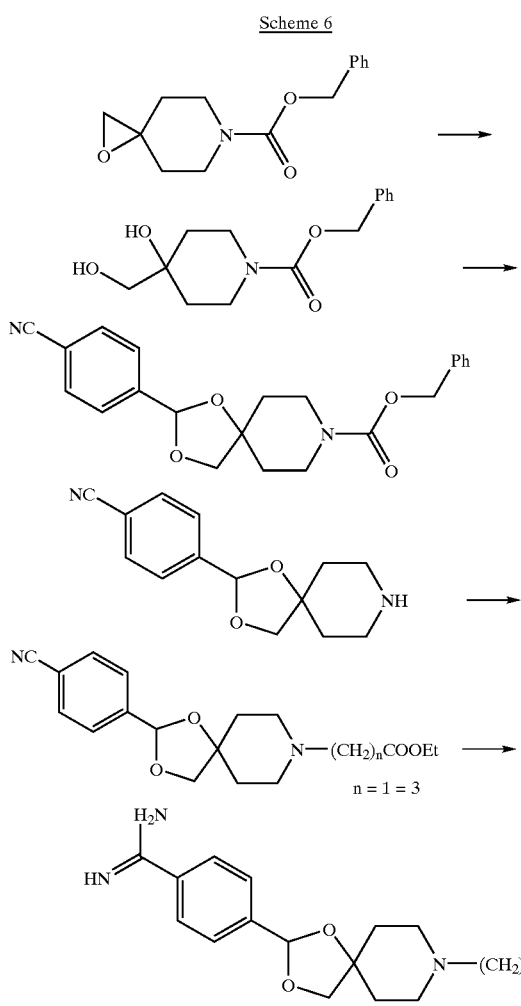

Scheme 6 illustrates the synthesis of 2-phenyl-1,3-dioxa-8-aza-spiro[4.5]decanes. N-protected 4-methylenepiperidine epoxides like benzyl 1-oxa-6-aza-spiro[2.5]octane-6-carboxylate are hydrolyzed to 4-hydroxy-4-hydroxymethylpiperidines by heating with diluted aqueous hydrochloric acid (see Eur. Pat. Appl. EP 189 370). The spiro-bicycle is obtained by condensation of the diol with 4-cyanobenzaldehyd, which may be achieved by heating in toluene and catalytic amounts of 4-toluenesulfonic acid or by reaction in the presence of boron trifluoride. The following steps: removal of the protecting group, alkylation with ω-halogenoalkanoates, formation of the amidine, and hydrolysis of the ester; are carried out as described in the previous Schemes.

Scheme 7

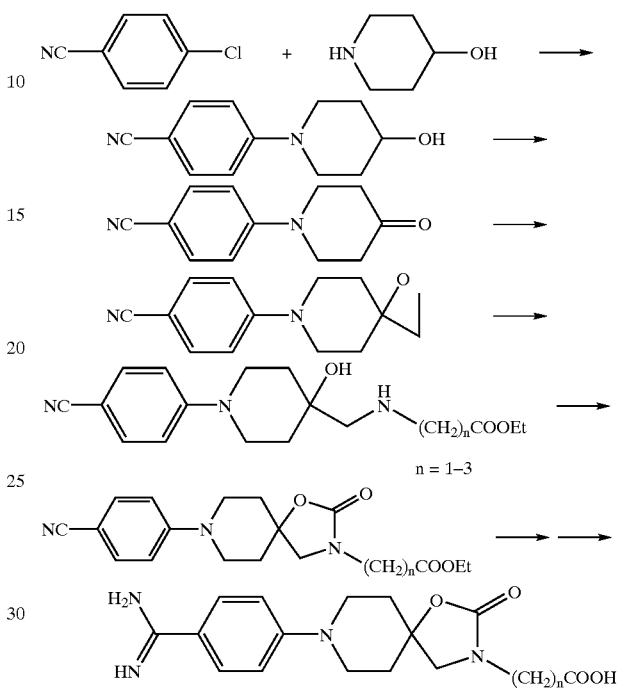

Scheme 7 describes the synthesis of 8-phenyl-1-oxa-3,8-diaza-spiro[4.5]decan-2-ones. 1-(4-Cyanophenyl)piperidin-4-ol is prepared by heating a mixture of 4-chlorobenzonitrile and piperidin-4-ol in DMF in the presence of sodium carbonate. The following oxidation to the piperidone is achieved with DMSO/oxalyl chloride (A. J. Mancuso, D. Swern, Synthesis 1981, 165), and the epoxide is formed by reaction with trimethylsulfoxonium iodide/sodium hydride in DMSO. After ring opening by reaction with ω-aminoalkanoates the following steps of formation of the spiro derivative and the amidino acid are carried out according to methods described in Scheme 1.

Scheme 8A

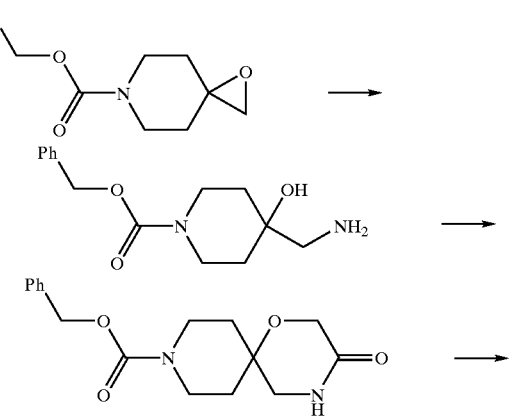

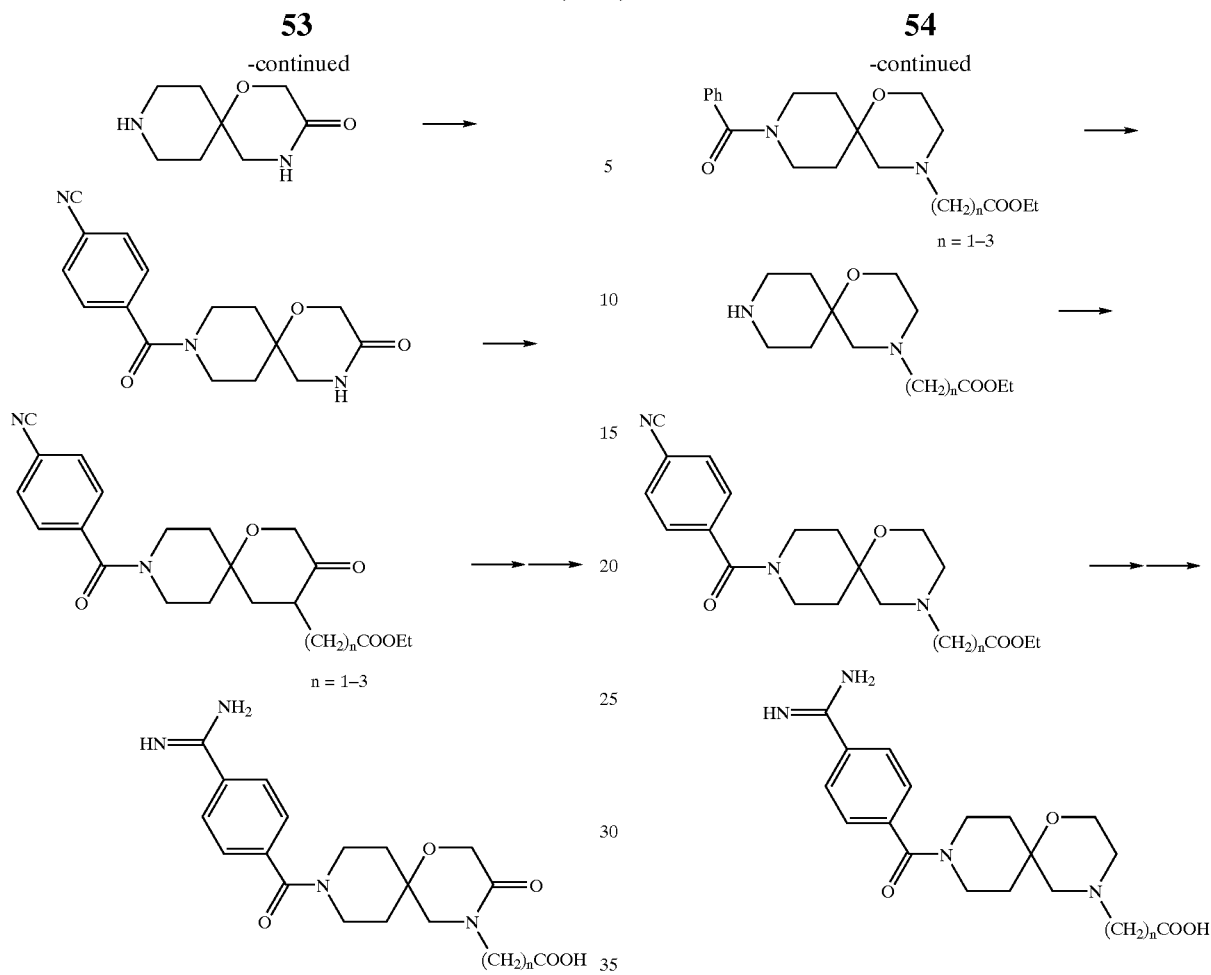

The synthesis of 1-oxa-4,9-diaza-spiro[5.5]undecan-3-ones is described in Scheme 8A (see R. D. Clark, J. M. Caroon, D. B. Repke, A. M. Strosberg, S. M. Bitter, M. D. Okada, A. D. Michel, R. L. Whiting, J. Med. Chem. 1983, 26, 855). N-protected 4-methylenepiperidine epoxides like benzyl 1-oxa-6-aza-spiro[2.5]octane-6-carboxylate are opened by heating with a methanolic solution of ammonia to give the corresponding 4-aminomethyl-4-hydroxypiperidine. The spiro-bicyclic nucleus is formed by the following condensation with chloroacetyl chloride. After removal of the benzyloxycarbonyl group with HBr in acetic acid the spiropiperidine is acylated with 4-cyanobenzoyl chloride. The subsequent steps of alkylation with ω-halogenoalkanoates, formation of the amidine, and cleavage of the ester are carried out as described in the previous Schemes.

Scheme 8B illustrates the synthesis of the related 1-oxa-4,9-diaza-spiro[5.5]undecanes. These are prepared by reduction of N(9)-protected 1-oxa-4,9-diaza-spiro[5.5]undecan-3-ones with lithium aluminum hydride. After alkylation with ω-halogenoalkanoates the protective group is removed, and the final steps of the sequence are carried out according to Scheme 8A.

Scheme 8B

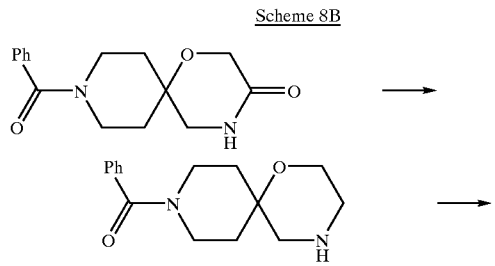

Scheme 9

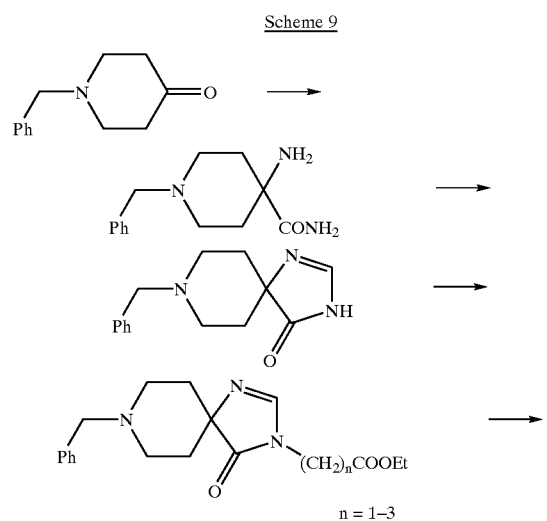

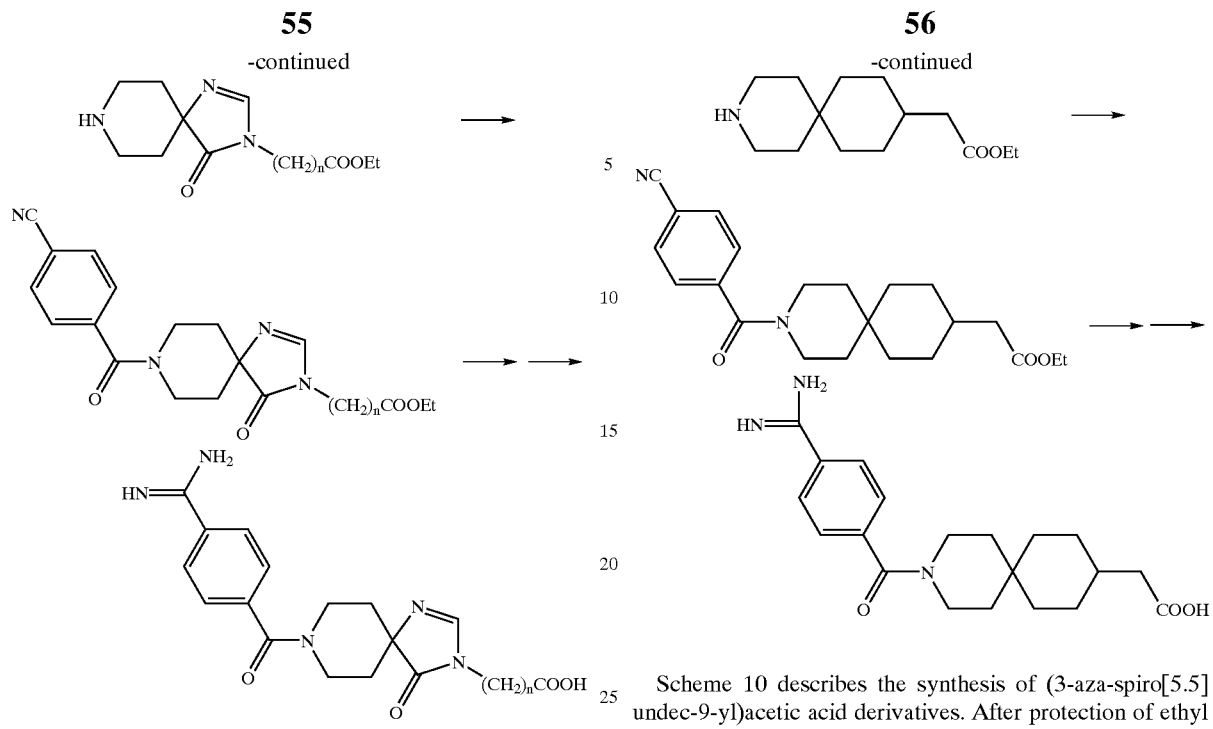

The synthesis of 1,3,8-triaza-spiro[4.5]dec-1-en-4-ones is described in Scheme 9 (see C. A. Bernhart, et al., J. Med. Chem. 1993, 36, 3371; C. del Campo, E. F. Llama, Org. Prep. Proced. Int. 1990, 22, 514). Protected 4-aminopiperidine-4-carboxamides are prepared by addition of potassium cyanide to corresponding piperidin-4-ones like N-benzylpiperidin-4-one followed by hydration of the nitrile intermediate. The spiro-bicyclic nucleus is obtained by heating with triethyl orthoformate or by reaction with gaseous formaldehyde. It is alkylated at the nitrogen in position 3 with ω-halogenoalkanoates and the benzyl group is removed by hydrogenation. After acylation with 4-cyanobenzoyl chloride the amidinocarboxylic acid is prepared according to methods described in the previous Schemes.

Scheme 10 describes the synthesis of (3-aza-spiro[5.5] undec-9-yl)acetic acid derivatives. After protection of ethyl isonipecotate with benzyl chloroformate the ester is reduced with lithiumaluminum hydride followed by Swern oxidation with oxalyl chloride/DMSO to corresponding 4-formylpiperidine. The spiro derivative is formed by condensation with 1-buten-3-one under basic conditions using potassium hydroxide, and the side chain is introduced by Horner-Emmons reaction with diethyl (ethoxycarbonyl) methylphosphonate/sodium hydride. The bicyclic nucleus and the exocyclic double bond are saturated and the protective group is removed by catalytic hydrogenation with palladium hydroxide on charcoal. The subsequent acylation with 4-cyanobenzoyl chloride, formation of the amidine, and hydrolysis of the ethyl ester are carried out by methods described in the previous Schemes.

Scheme 10

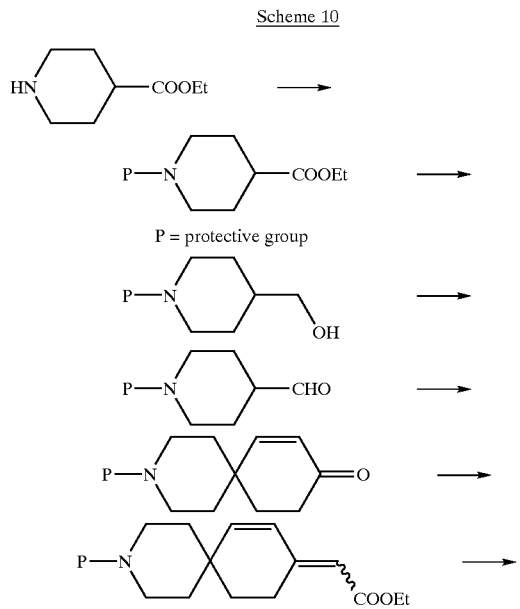

Scheme 11a

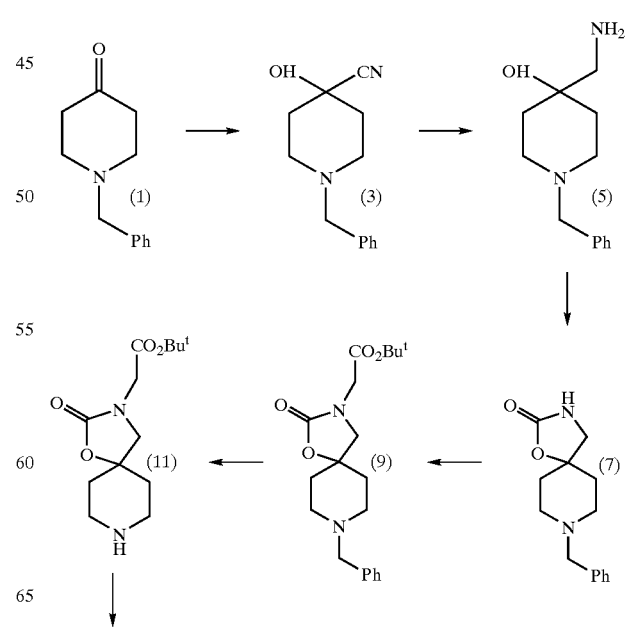

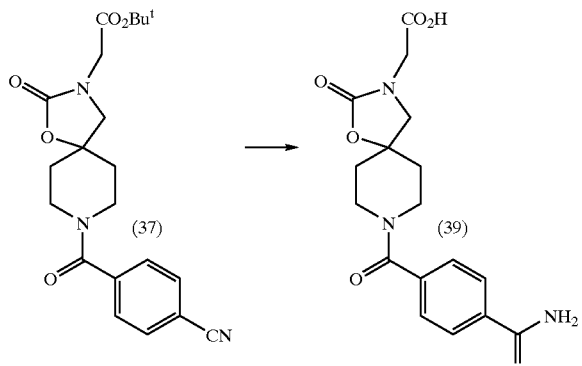

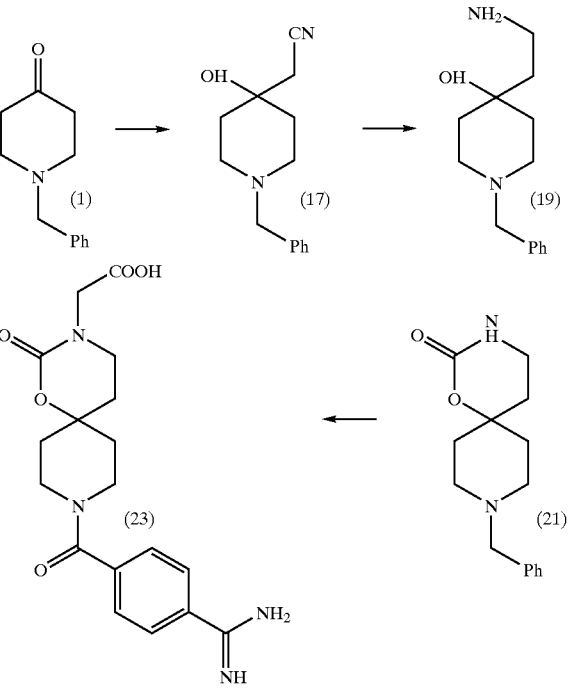

Scheme 11b

Scheme 11a describes the preparation of 6,5 spiro-fused piperidino-carbamates in which the carbamate nitrogen is substituted with an acetic acid residue and the piperidine nitrogen is acylated with a benzamidine. In the first step, 4-piperidone (1) is allowed to react with TMSCN resulting in the formation of cyanohydrin (3). The nitrile moiety is reduced with LAH providing amino-alcohol (5), which is then allowed to react with diethyl carbonate in the presence of NaH ultimately forming spiro carbamate (7). Alkylation of the carbamate nitrogen is accomplished with NaH and alpha-bromo acetate giving ester (9). Catalytic hydrogenation removes the benzyl group providing free amine (11) which is acylated with 4-cyanobenzoic acid yielding (13). The nitrile moiety in (13) is converted to a protected amidine and is isolated as its Boc derivative. This material is then fully deprotected with TFA providing (15) as a salt.

Materials containing a 6,6 spiro-fused piperidino-carbamate can be prepared in an analogous fashion (see Scheme 11b). Lithio-acetonitrile is allowed to react with 4-piperidone resulting in the formation of alcohol (17). This material can be transformed into final product (23) using the same set of reactions described for the conversion of (1) to (15).

Scheme 11c

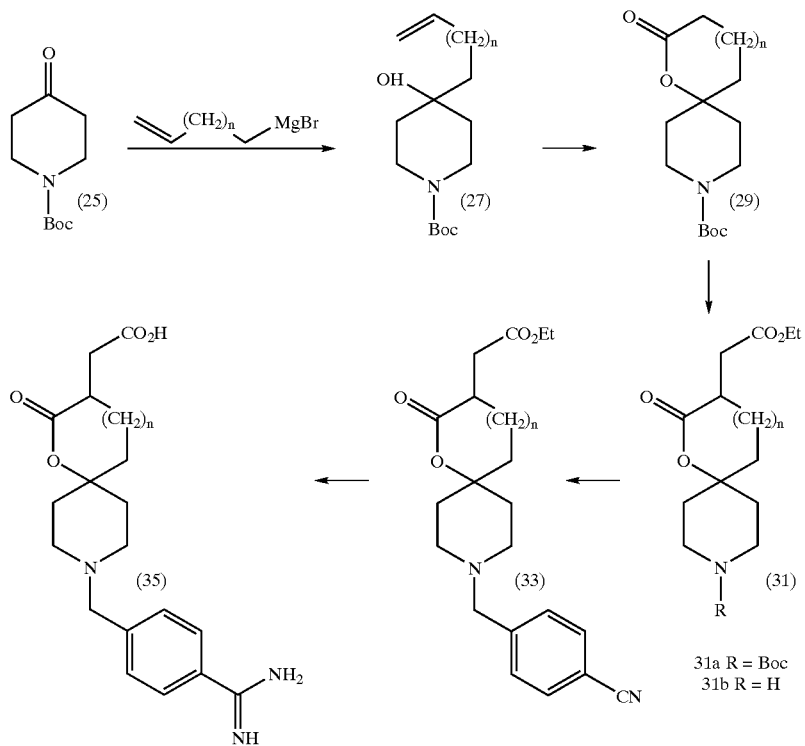

31a R = Boc
31b R = H

Scheme 11c describes the preparation of compounds containing a disubstituted 6,6 and 6,5 spirolactone. In the first step, piperidone 25 is allowed to react with the olefinic grignard reagent giving adduct 27. Oxidation of this material with permanganate affords lactone 29. Alkylation of the lactone enolate with an α bromo ester provides the functionalized product 31. Removal of the Boc protecting group with TFA liberates amine 33 which can be acylated with 4-cyanobenzoic acid providing adduct 35. The nitrile moiety in this molecule can be converted to an amidine using the thio-Pinner protocol and then deprotected giving compound 39.

Scheme 12

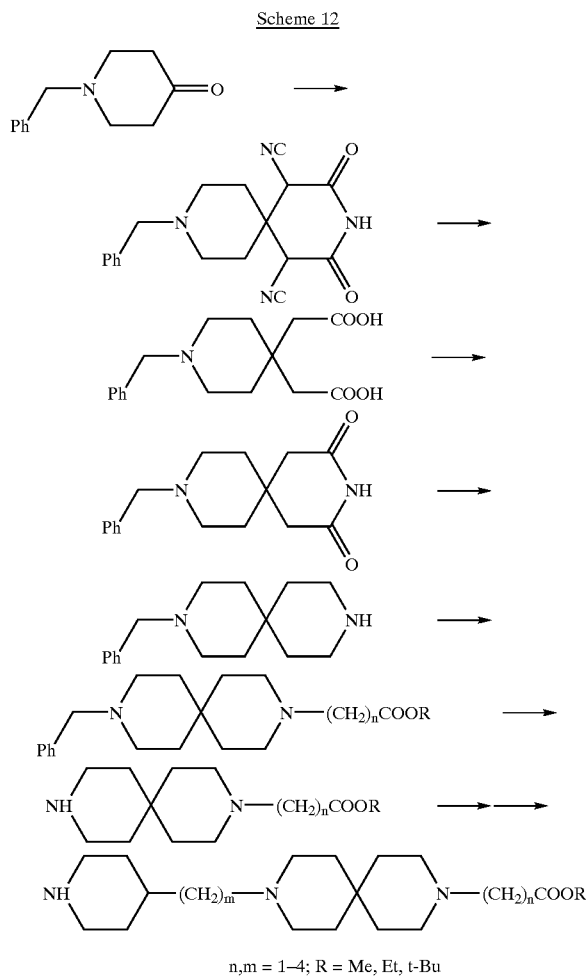

n,m = 1–4; R = Me, Et, t-Bu

Scheme 13

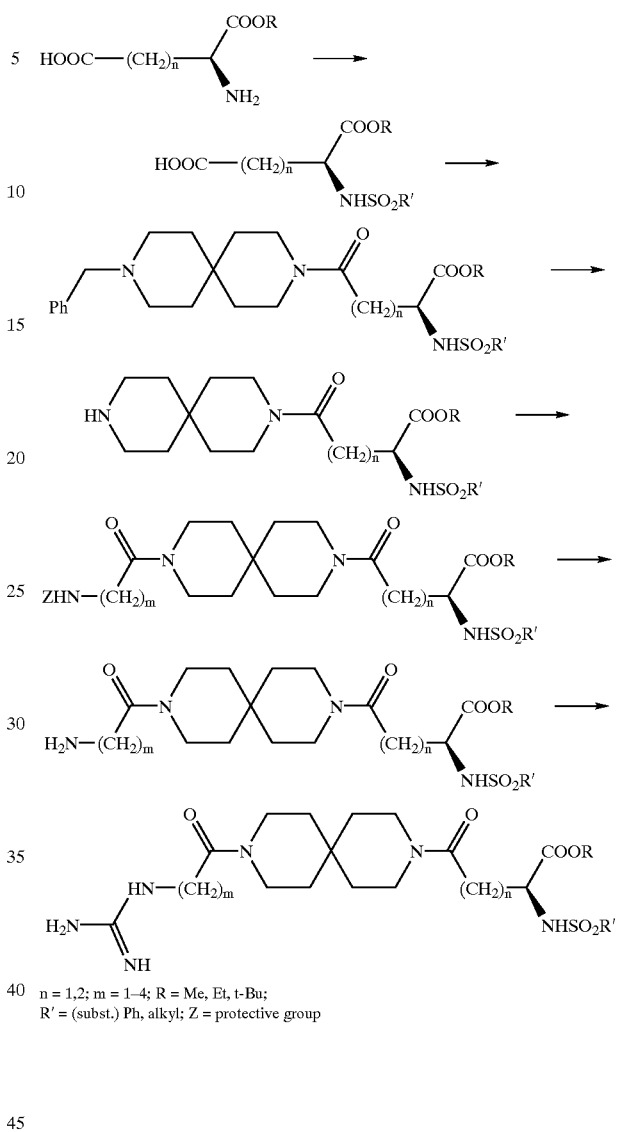

n = 1,2; m = 1–4; R = Me, Et, t-Bu;
R' = (subst.) Ph, alkyl; Z = protective group Scheme 12 describes the preparation of 3,9-diazaspiro-[5.5]undecane compounds. The diazaspiro skeleton is prepared according to known procedures (see S. M. McElvain and R. E. Lyle, Jr., *J. Am. Chem. Soc.*, 1967, 32, 1966). The intermediate diazasprirocyclic compound is alkylated by ω-haloalkanoodes. After removal of the benzyl group, it is alkylated either by N-protected-4-(ω-haloalkyl)piperidines or by corresponding pyridines, which are readily reduced to piperidines by hydrogenation as shown in the experimental section below. In a similer manner, any other basic residue with an appropriate spaced is prepared.

1-Monoesters of aspartic acid (n=1) or glutamic acid (n=2), N-protected derivatives of these monoesters, or other similarly protected compounds are commercially available or have been described previously in the literature. See Gregory et al., *J. Chem. Soc.* (c), 1968, 715; Olsen et al., *J. Org. Chem.*, 1984, 49, 3527; Yang and Menifield, *J. Org. Chem.*, 1976, 41, 1032; Taschner et al., *Liebigs Ann. Chem.*, 1961, 646, 123, 125, 127, 134. These compounds are connected to sulfonamides by reaction with sulfonyl chlorides. Preferred sulfonyl chlorides are benzenesulfonyl chloride or n-butanesulfonyl chloride. The 3,9-diazaspiro-[5.5] undecane compound from Scheme 12 is acylated by these intermediates, followed by removal of the portective group. It is acylated by N-protected ω-aminocarboxylic acids bearing protective groups, such as t-butoxycarbonyl or benzyloxycarbonyl. The protective group is removed and the free amine is converted to a guanidine, which is optionally protected using standard procedures such as by reaction with N,N'-bis(t-butoxycarbonyl)thiourea and heavy metal salts (e.g. copper or mercury).

Scheme 14

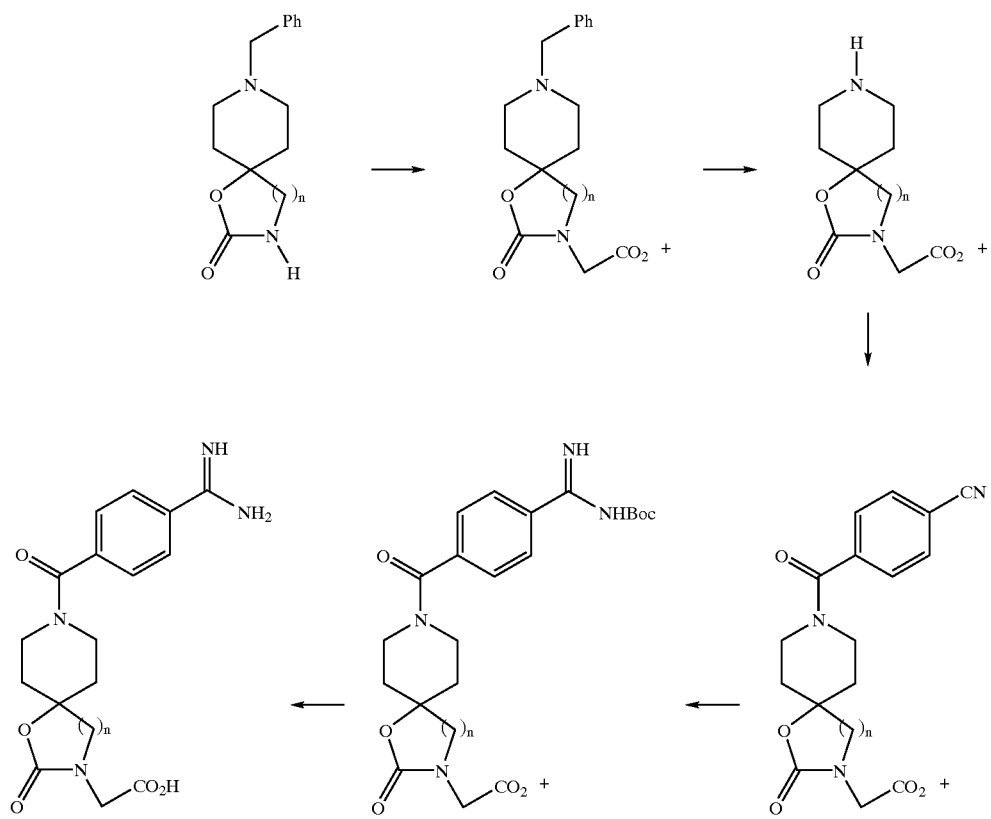

Scheme 14 outlines the preparation of the 6,5 (n=1) and 6,6 (n=2) spiro-carbamates with substitution of a basic residue on the piperidine nitrogen and an acidic residue on the carbamate nitrogen. The protected compound is deprotonated with sodium hydride in an aprotic solvent, such tetrahydrofuran, and the resulting sodium salt is reacted with an α-halo ester to.provide the mono-substituted products. These compounds are then deprotected to give the secondary amines. These materials are then acylated giving N-alkylated, N-acylated intermediate products. The nitrile group is transformed to an amidino group using a modified thio-Pinner sequence. More specifically, reaction of the nitrile to form the thioamide followed by S-alkylation with methyl iodide, and then.displacement with ammonia. Preferably, the intermediate compounds are not isolated but are reacted with di-t-butyl dicarbonate to give the protected amidines. These intermediate compounds are fully deprotected, for example with trifluoroacetic acid, to give the desired products.

Scheme 15

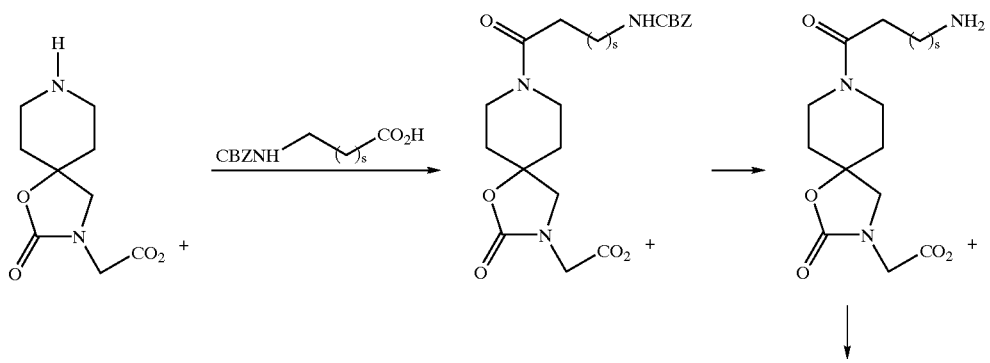

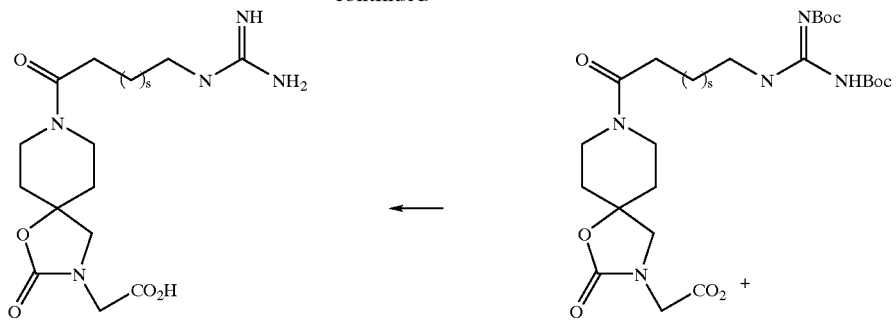

Scheme 15 outlines the preparation of 6,5 spiro-carbamates with substitution of an alkyl guanidine on the piperidine nitrogen, and an acicic residue on the carbamate nitrogen. The intermediate compound prepared as described in Scheme 14, is acylated with protected amino acids providing the intermediate amide compounds. The protecting groups are then removed using reactions well known in the chemical arts, and materials are guanylated providing the fully-protected intermediate compounds. Complete deprotection, for example with trifluorocacetic acid, provides the desired compounds.

Scheme 16

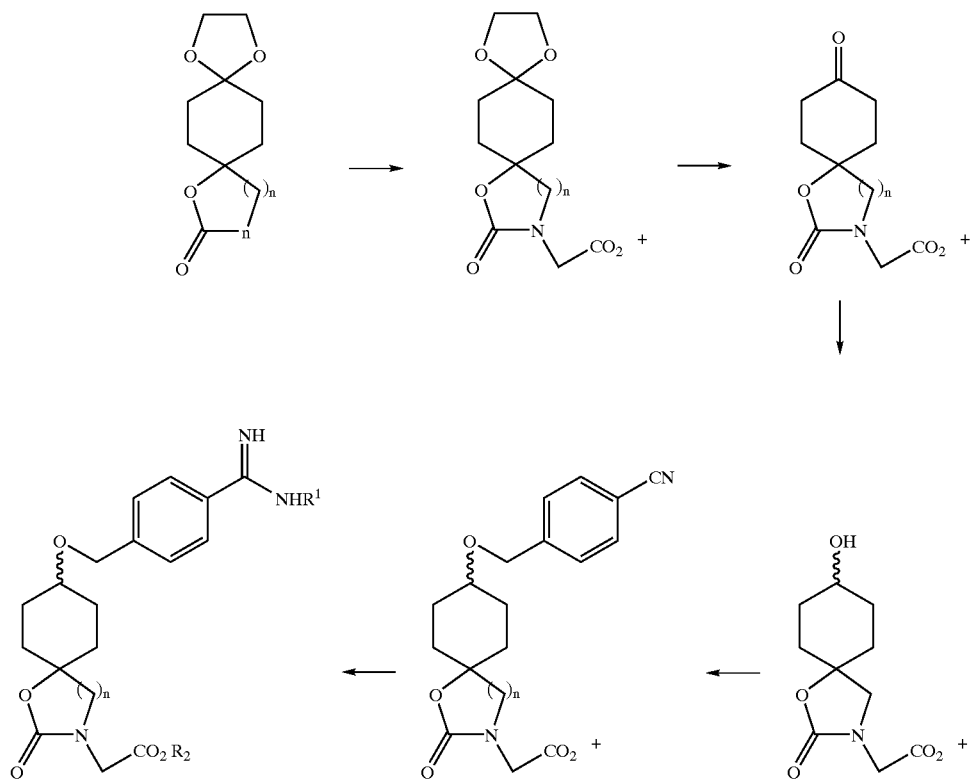

Scheme 16 describes the synthesis of spiro-carbamates containing an oxygen-linked basic group, where n is 1 or 2. The starting compound is alkylated on nitrogen by reacting with a strong base, such as sodium hydride, and an alkylating agent, such as an α-bromo-t-butyl acetate. The protecting group for the ketone functional group is then removed, and the ketone reduced with a hydride reducing agent, such as sodium borohydride, to provide a mixture of alcohols.

The alcohols are alkylated with 4-cyanobenzyl bromide, and the resulting compound is transformed into the protected amidine.

Scheme 17

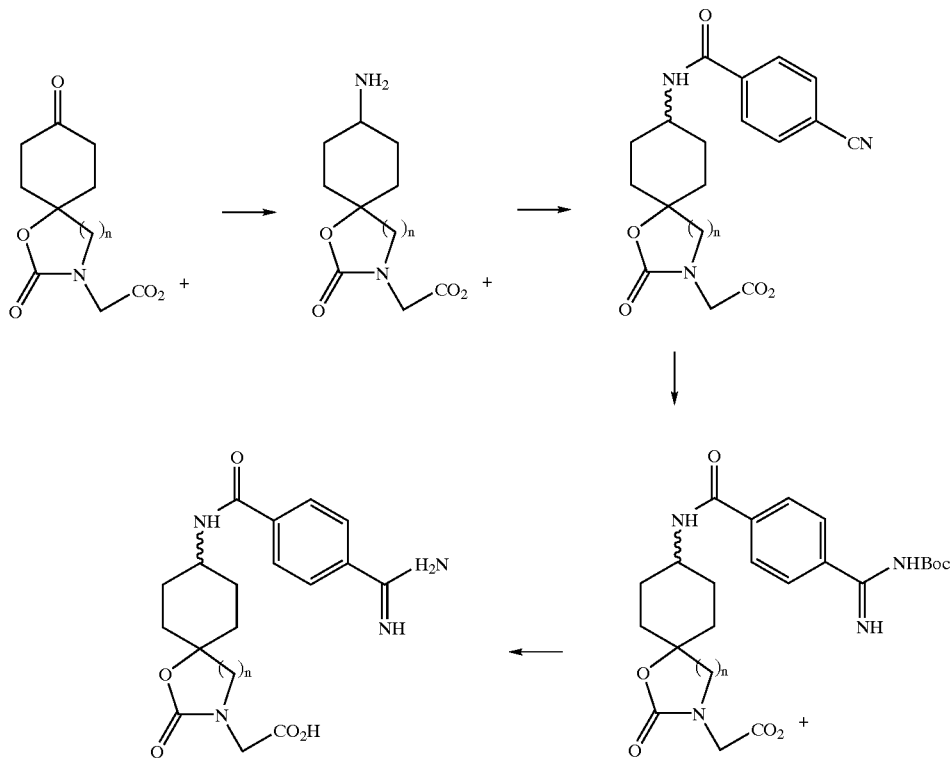

Scheme 17 describes the synthesis of spiro carbamates containing an amide-linked basic group on the saturated ring. The intermediate ketone, prepared as shown in Scheme 16, is reductively aminated with an amine and sodium cyanoborohydride. This intermediate compound is acylated with 4-cyanobenzoic acid providing the amide intermediate. This amide is converted to the protected amidine using procedures well known in the chemical arts. The resulting compound is converted into the desired compound using procedures as described previously.

Scheme 18

-continued
Scheme 19

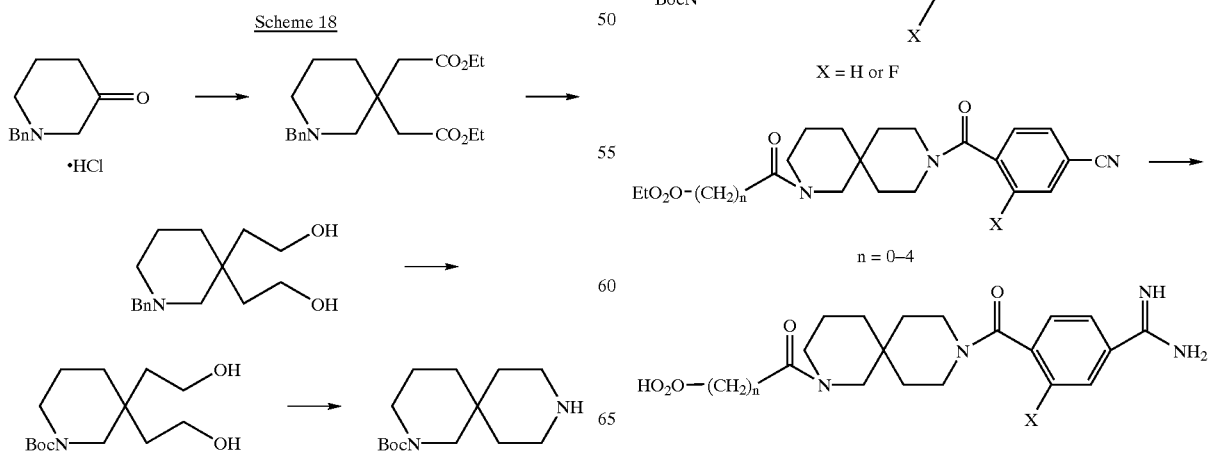

Scheme 19 describes the synthesis of 9-benzoyl-2,9-diaza-spiro[5.5]undecanes in which the nitrogen in the 2-position is acylated. The 2,9-diaza-spiro[5.5]undecane template is prepared as described in Example 40 (see also U.S. Pat. No. 5,451,578). Treatment of this mono-protected material with 4-cyanobenzoyl chloride (or 2-fluoro-4-cyanobenzoyl chloride) in the presence of a base such as triethylamine gives the benzamide intermediate. The protecting group is removed with trifluoroacetic acid followed by acylation with the appropriate ester-acid chloride such as methyl oxalyl chloride or methyl adipoyl chloride. After mild basic hydrolysis of the ester, the nitrile is converted to the amidine utilizing a three step protocol: 1) treatment with hydrogen sulfide in pyridine in the presence of triethylamine; 2) treatment with methyl iodide in acetone; and 3) treatment with ammonium acetate in ethanol, thus providing the amidino carboxylic acids.

Scheme 20

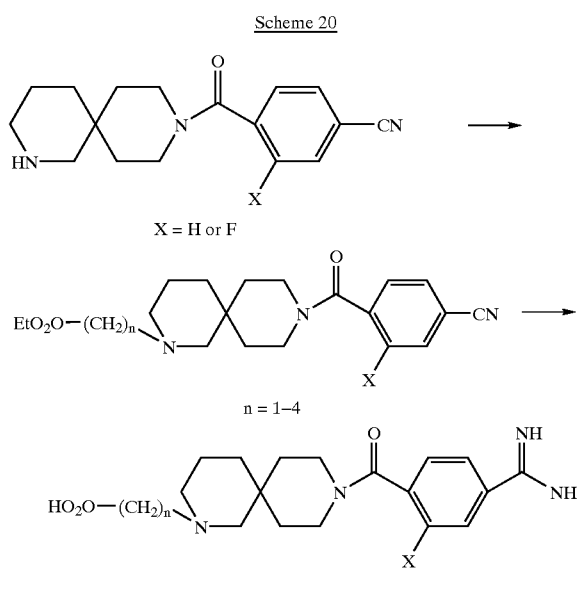

Scheme 20 describes the synthesis of 9-benzoyl-2,9-diaza-spiro[5.5]undecanes in which the nitrogen in the 2-position is alkylated. After removal of the protecting group with trifluoroacetic acid in the benzamide intermediate as in Scheme 19, the secondary amine is alkylated with the appropriate halogenoester such as ethyl bromoacetate or ethyl 4-bromobutanoate. Mild basic hydrolysis of the ester followed by nitrile to amidine conversion as described in the previous Scheme provides the amidino carboxylic acid.

Scheme 21

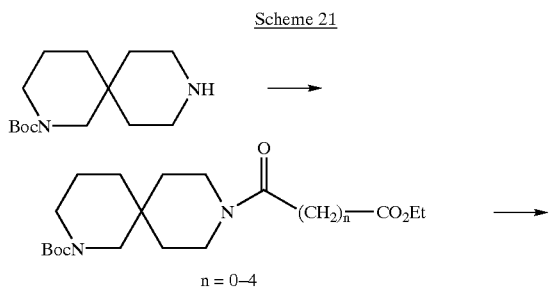

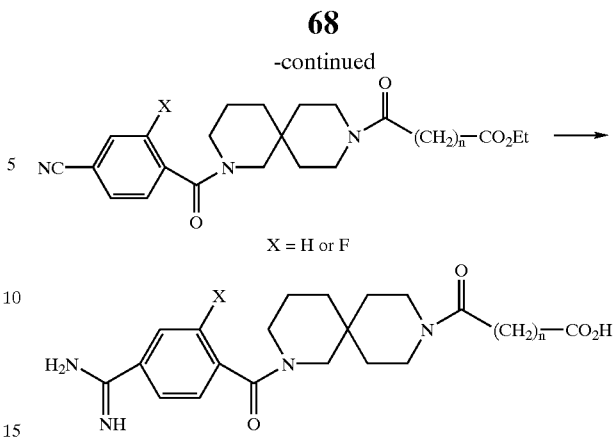

Scheme 21 describes the synthesis of 2-benzoyl-2,9-diaza-spiro[5.5]undecanes in which the nitrogen in the 9-position is acylated. The mono-protected 2,9-diaza-spiro[5.5]undecane is acylated with the appropriate ester-acid chloride in the presence of triethylamine. Removal of the protecting group with trfluoroacetic acid is followed by acylation with 4-cyanobenzoyl chloride (or 2-fluoro-4-cyanobenzoyl chloride). Mild basic hydrolysis of the ester is followed by conversion of the nitrile to the amidine as previously described for Scheme 19.

Scheme 22

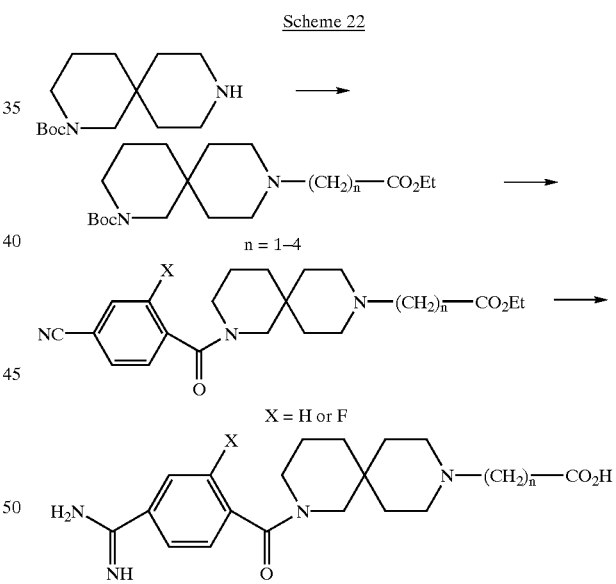

Scheme 22 describes the synthesis of 2-benzoyl-2,9-diaza-spiro[5.5]undecanes in which the nitrogen in the 9-position is alkylated. The mono-protected 2,9-diaza-spiro[5.5]undecane is alkylated with the appropriate halogenoester in the presence of triethylamine. Removal of the protecting group with trifluoroacetic acid is followed by acylation with 4-cyanobenzoyl chloride (or 2-fluoro-4-cyanobenzoyl chloride). Mild basic hydrolysis of the ester is followed by conversion of the nitrile to the amidine as previously described for Scheme 19.

Scheme 23

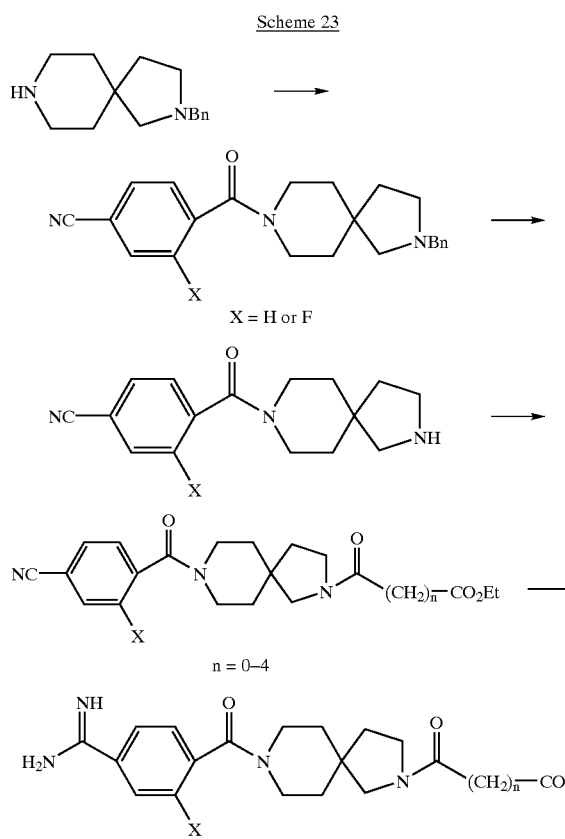

X = H or F n = 0–4

Scheme 23 describes the synthesis of the 8-benzoyl-2,8-diaza-spiro[5.4]decanes in which the nitrogen in the 2-position is acylated. The mono-protected 2,9-diaza-spiro[5.5]undecane nucleus (see: J. Med. Chem. 1995, 3, 3772–3779) is acylated with 4-cyanobenzoyl chloride (or 2-fluoro-4-cyanobenzoyl chloride). Hydrogenolysis of the benzyl protecting group with palladium on charcoal is followed by acylation with the appropriate ester-acid chloride. Subsequent hydrolysis under mildly basic conditions and then conversion of the nitrile to the amidine as previously described affords the amidino carboxylic acids.

Scheme 24

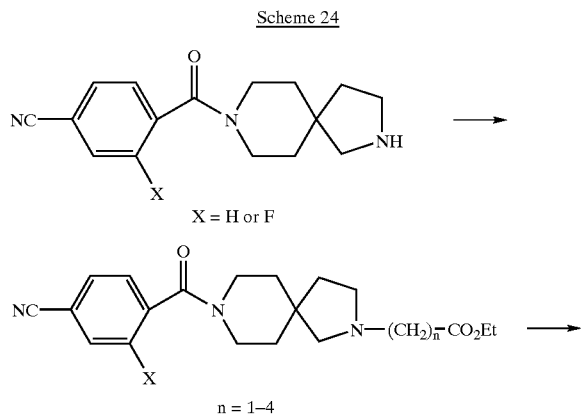

X = H or F n = 1–4

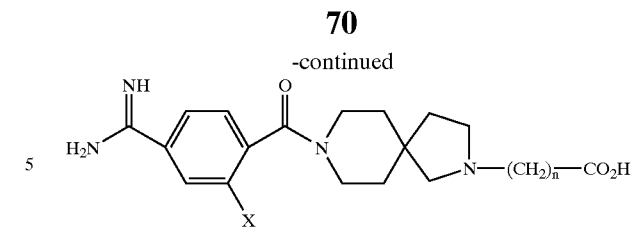

Scheme 24 describes the synthesis of the 8-benzoyl-2,8-diaza-spiro[5.4]decanes in which the nitrogen in the 2-position is alkylated. Hydrogenolysis of the benzyl protecting group with palladium on charcoal is followed by alkylation with the appropriate halogenoester. The amidino carboxylic acids are obtained upon hydrolysis of the ester and then conversion of the nitrile, as previously described, to the amidine.

Scheme 25

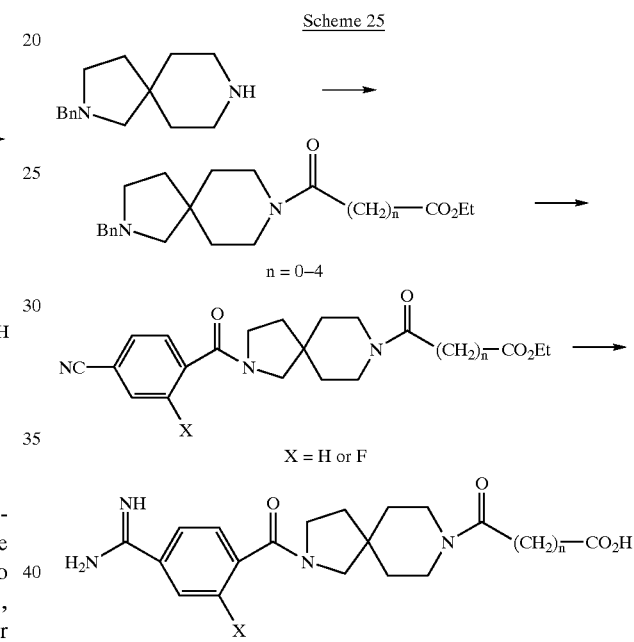

n = 0–4

X = H or F

Scheme 25 describes the synthesis of the 2-benzoyl-2,8-diaza-spiro[5.4]decanes in which the nitrogen in the 8-position is acylated. The mono-protected 2,8-diaza-spiro[5.4]decane is acylated with the appropriate ester-acid chloride. Hydrogenolysis of the benzyl protecting group with palladium on charcoal is followed by acylation with 4-cyanobenzoyl chloride (or 2-fluoro-4-cyanobenzoyl chloride). Subsequent hydrolysis of the ester under mildly basic conditions and then conversion of the nitrile to the amidine as previously described affords the amidino carboxylic acids.

Scheme 26

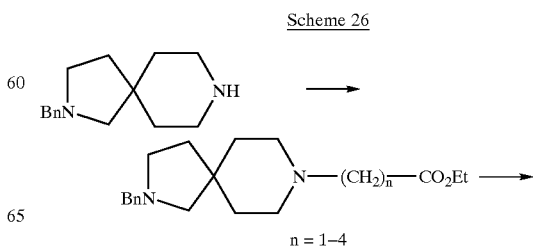

n = 1–4

71

-continued

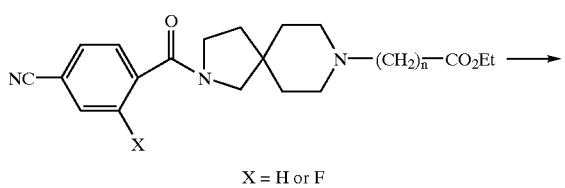

X = H or F

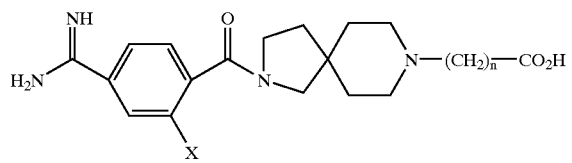

Scheme 26 describes the synthesis of the 2-benzoyl-2,8-diaza-spiro[5.4]decanes in which the nitrogen in the 8-position is alkylated. The mono-protected 2,8-diaza-spiro[5.4]decane is alkylated with the appropriate halogenoester. Hydrogenolysis of the benzyl protecting group with palladium on charcoal is followed by acylation with 4-cyanobenzoyl chloride (or 2-fluoro-4-cyanobenzoyl chloride). Hydrolysis of the ester under mildly basic conditions and then conversion of the nitrile to the amidine as described in Scheme 19 affords the amidino carboxylic acids.

Scheme 27

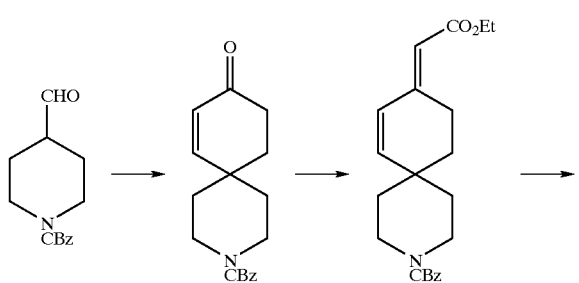

72

-continued

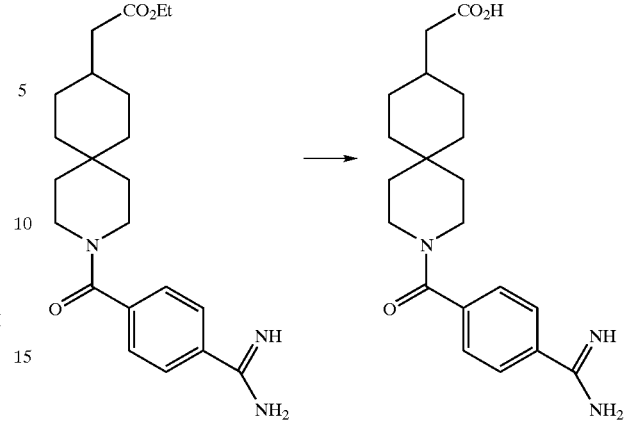

The Scheme 27 describes the synthesis of (3-aza-spiro[5.5]undec-9-yl)acetic acid derivatives. The ethylisonipecotate was protected with benzyl chloroformate, then the ester was reduced with lithium aluminum hydride followed by sworn oxidation with oxalyl chloride/dimethyl sulfoxide to the corresponding 4-formylpiperidine. The spirocyclic ring was formed by the base catalyzed michael addition of methyl vinyl ketone to the aldehyde followed by acid catalyzed aldol cyclization and dehydration to afford the desired spirocyclic enone. The side chain elongation is carried out by Homer-Emmons condensation with triethylphosphonoacetate/sodium hydride in THF. The bicyclic nucleus and the exocyclic double bond are saturated and the protective group is removed by catalytic hydrogenation.

The nitrogen of the aza spiro compound was acylated with p-cyanobenzoyl chloride. The nitrile was converted to N-hydroxyamidino by treating with hydroxylamine hydrochloride in triethylamine and ethanol as solvent. The hydroxylamidino moiety was hydrogenated with 5% Pd/C (50% wet) at 60° C. using 50 psi $H_2$ overnight to afford the desired amidino functionality. The catalyst was filtered through celite and solvent evaporated under reduced pressure. The hydrolysis of ester was carried out under basic conditions to give the desired final product.

Scheme 28

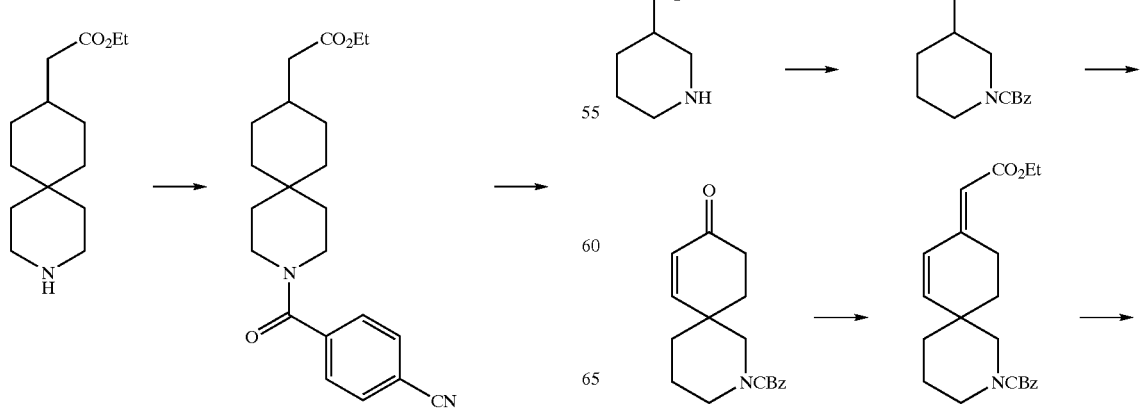

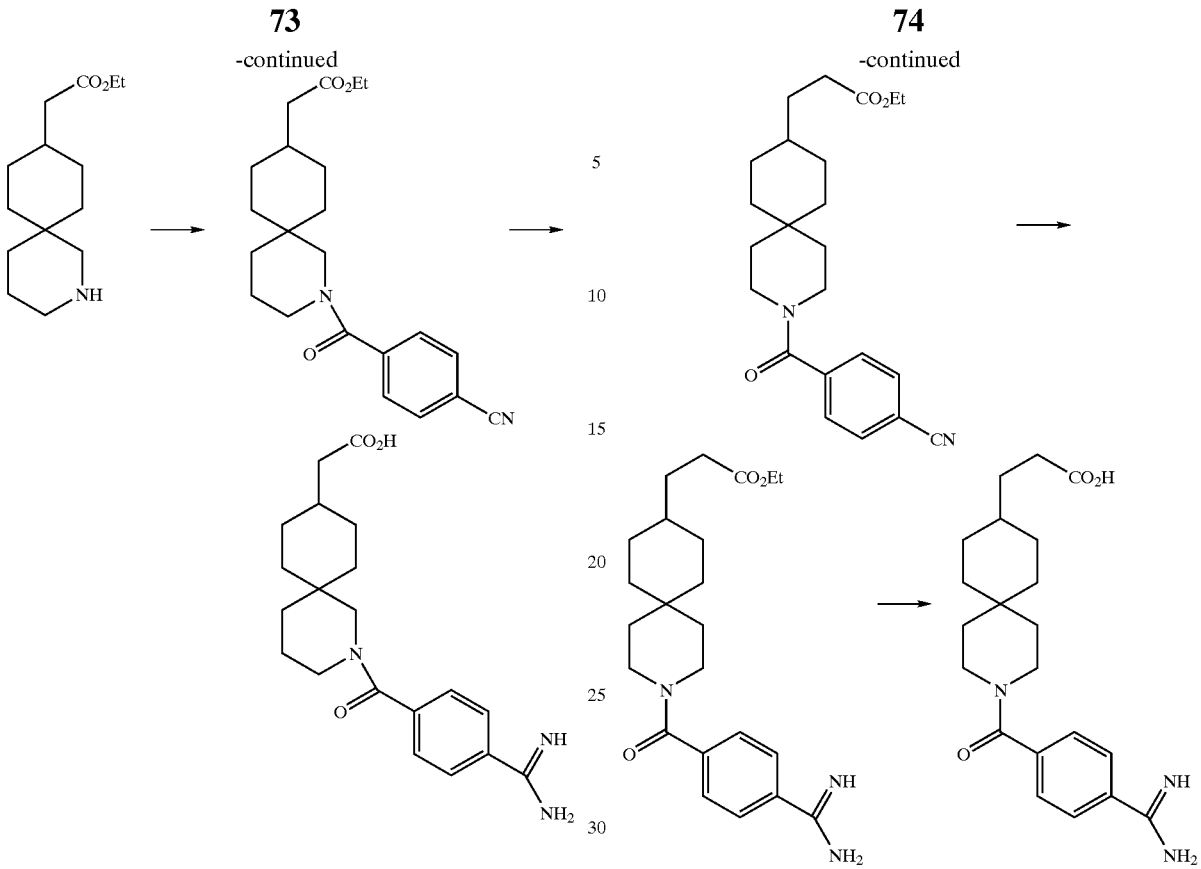

The Scheme 28 describes the synthesis of (2-aza-spiro[5.5]undec-9-yl)acetic acid derivatives. The 3-piperidinemethanol was protected with benzylchloroformate and then oxidized under swemn conditions. The subsequent spiro ring formation, Homer-Emmons, acylation, formation of amidine, and hydrolysis of ester were carried out by methods described in previous Scheme 27.

Scheme 29

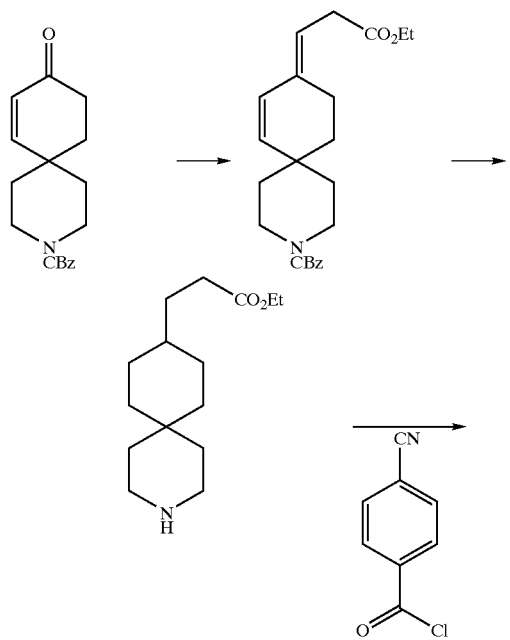

The Scheme 29 describes the synthesis of (3-aza-spiro[5.5]undec-9-yl)propionic acid derivatives. The spirocyclic enone was synthesized as shown in Scheme 37, followed by Horner-Emmons reaction with triethylphosphono propionate. The bicyclic nucleus and the exocyclic double bond are saturated and the protective group is removed by catalytic hydrogenation.

The nitrogen of the aza spirocompound was acylated with p-cyanobenzoyl chloride. The nitrile was converted to N-hydroxyamidino by treating with hydroxylamine hydrochloride in triethylamine and ethanol as solvent. The hydroxylamidino moiety was hydrogenated with 5% Pd/C (50% wet) at 60° C. using 50 psi $H_2$ overnight to afford the desired amidino functionality. The catalyst was fifltered through celite and solvent evaporated under reduced pressure. The hydrolysis of ester was carried out under basic conditions to give the desired final product.

Scheme 30

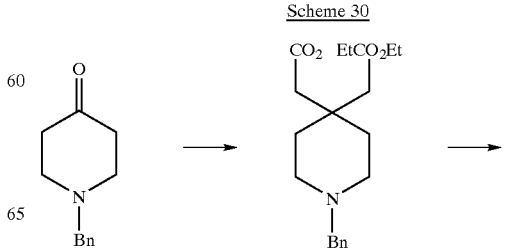

-continued

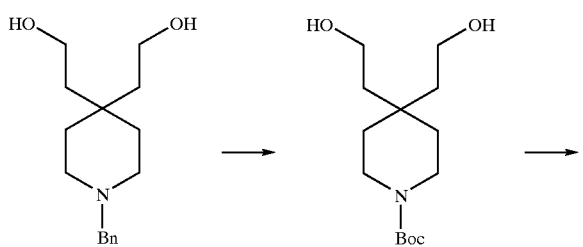

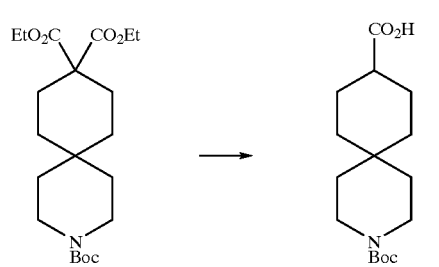

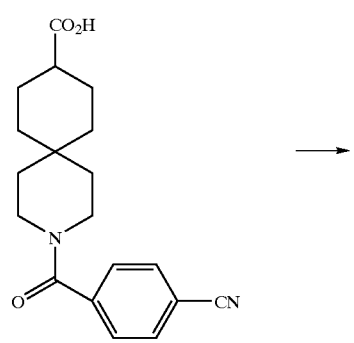

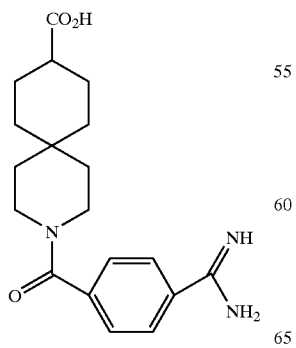

The Scheme 30 describes the synthesis of (3aza-spiro[5.5]undec-9-yl)formic acid) derivatives (see U.S. Pat. No. 5,451,578). The shown diester is formed by Knoevenagel condensation between N-benzylpiperdone and ethyl cyanoacetate. The hydrolysis and esterification is carried out with ethanol and sulfuric acid to give the diester. The diester after purification is reduced to diol with LAH. The debenzylation followed by Boc-protection was carried out in one step by hydrogenation with palladium hydroxide in presence of Boc2O. The diol was converted to mesylate, followed by condensation with diethylmalonate to afford the spirocyclic diester. The diester was hydrolyzed to diacid followed by decarboxylaton to afford the 3-aza-spiro[5.5]undec-9-yl) formic acid. The deprotection with TFA followed by acylation with p-cyanobenzoyl chloride and conversion of nitrile to amidino was carried out utilizing a three step protocol: 1) treatment with hydrogen sulfide in pyridine in the presence of triethylamine; 2) treatment with methyl iodide in acetone; and 3) treatment with ammonium acetate in ethanol, thus providing the amidino carboxylic acid.

Scheme 31

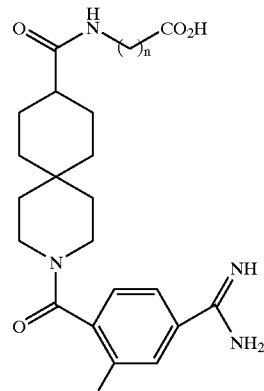

n = 1–4
X = H or F

The Scheme 35 describes the synthesis 3-{2-[(3-Azaspiro[5.5]undecane-9-carbonylamino}acetic acid. The BOC-acid from Scheme 34 is coupled with glycine ethyl ester or 3-aminoethylpropionate in presence EDC, HOBt, DIEA to afford the amide. The deprotection of Boc followed by acylation with p-cyanobenzoyl chloride, amidino formation, and hydrolysis of ester are carried out as described in the previous schemes.

Scheme 32

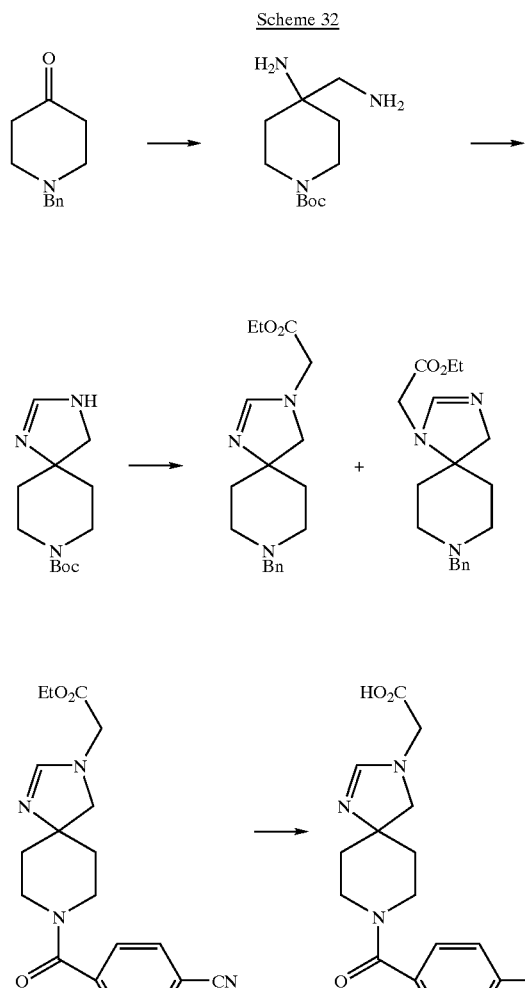

Scheme 33

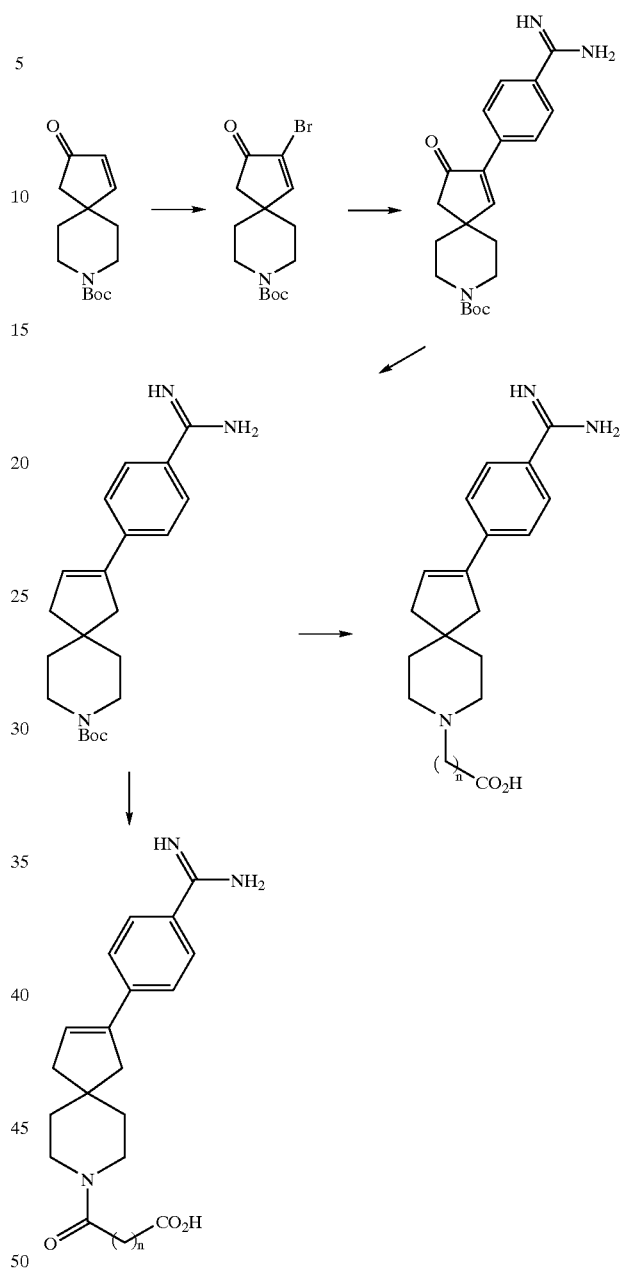

The Scheme 32 describes the synthesis of 8-benzoyl-1,3,8-triaza-spiro[4.5]dec-1-en. The spiro-imidazoline template is synthesized from N-Boc-4-piperidone, via synthesis of amino nitrile by the strecker reaction. Reduction of amino nitrile with LAH to ethylene diamine. Ethylene diamine is cyclized by mild reaction with formamidine acetate in ethanol at room temperature. The alkylation of spiro-imidazoline with appropriate halogenated alkyester gives mixture of N-1 and N-3 alkylated product which can be separated. The protecting group is removed with trifluoroacefic acid and N-8 is acylated with 4-cyanobenzoyl chloride. After basic hydrolysis of ester, the nitrile is converted to amidine utilizing the procedure as described in earlier schemes.

The Scheme 33 describes the synthesis of 8-aza-spiro[5.4]dec-3-en-2-one in which the nitrogen in the 8-position is alkylated or acylated depending of the derivative being synthesized. The intermediate aza-spiro[4.5]deca-enone template is prepared as described in Scheme 27. The α-bromination of the enone followed by palladium catalyzed coupling with 4-amidinoboronic acid will give the desired alkylated spiro-alkylated amidine. The reduction of tosylhydrazone of α,β-unsaturated ketones with sodium cyanoborohydride will give the alkene with the double bond migration (see R. O. Hutchins, M. Kaucher, and L. Rua, J. Org. Chem, 1975, 40, 923). The deprotection with TFA followed by alkylation with appropriate halogenated alkylester or acylation with appropriate ester-acid chloride will give the desired N-alkylated or N-acylated intermediates. After mild basic hydrolysis of the ester will give the desired amidino carboxylic acids.

tecting group is removed with trifluoroacetic acid followed by acylation with the 4-cyanobenzoyl chloride (or 2-fluoro-4-cyanobenzoyl chloride) in presence of base such as triethylamine. After mild basic hydrolysis of ester, the nitrile is converted to the amidine as described in earlier schemes, thus providing the desired amidino carboxylic acids.

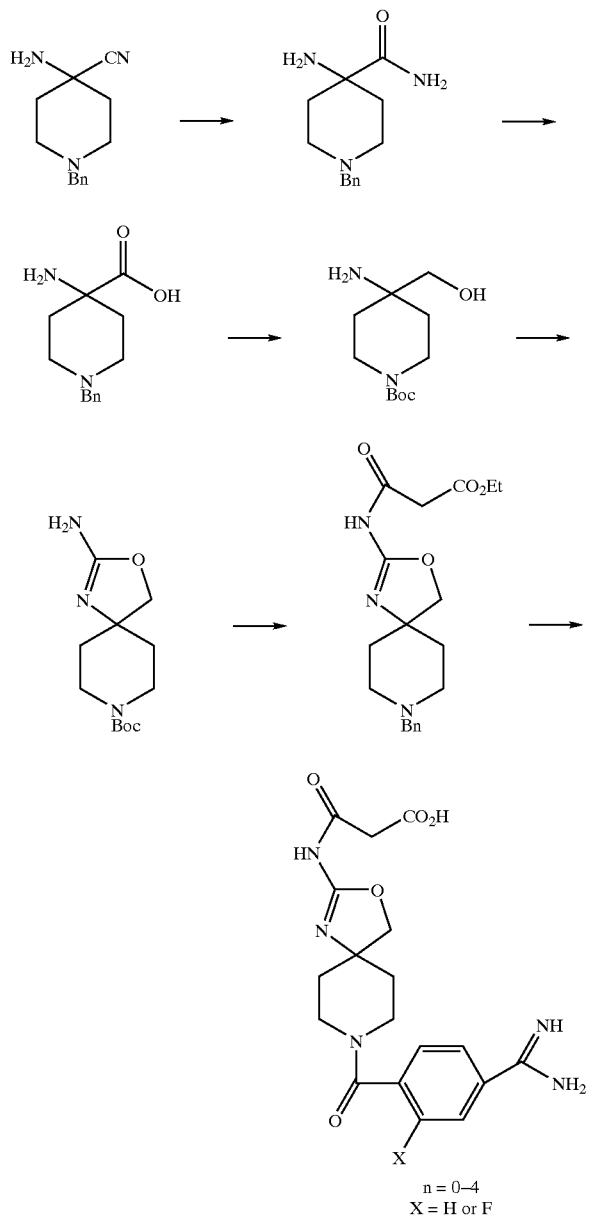

Scheme 34

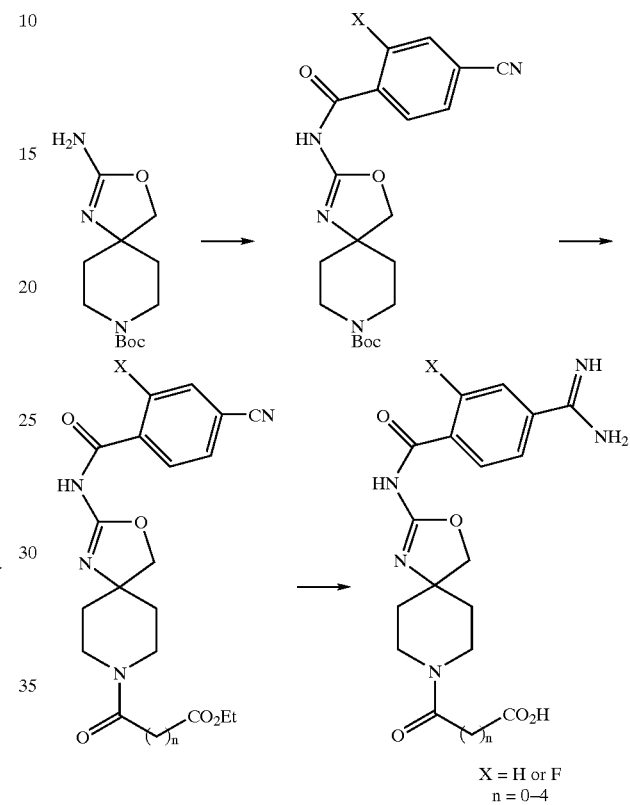

Scheme 35

The Scheme 35 describes the synthesis of 2-benzoyl-3-oxa-1,8-diaza-spiro[4.5]dec-1-ene in which the nitrogen in the 2-position is benzoylated. The 2-amino spiro-oxazoline is acylated with 4-cyanobenzoyl chloride. The protecting group is removed with trifluoroacetic acid followed by acylation with appropriate ester-acid chloride. After mild basic hydrolysis of ester, the nitrile is converted to amidino to give the desired product.

The Scheme 34 describes the synthesis of 8-benzoyl-2-amino-3-oxa-1,8-diaza-spiro[4.5]dec-1-enes in which the nitrogen in the 8-position is acylated. The N-Benzyl-4-piperidone was converted to the corresponding amino nitrile by the strecker reaction (see A. A. Cordi, J M. Lacoste, C. Courchay, P M. Vanhoutte, J. Med. Chem, 1995, 38, 4056). The stepwise hydrolysis of aminonitrile to amino acid followed by reduction of acid to alcohol. The debenzylation is carried out by catalytic hydrogenation and insitu protection with Boc-anhydride. The amino alcohol is cyclized with cyanogen bromide to give spiro-oxazoline ring. The 2-amino is acylated with appropriate ester-acid chloride or alkylated with appropriate halogenated alkylester. The pro- Scheme 36

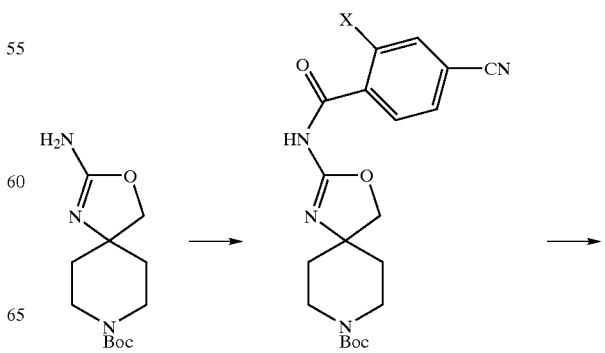

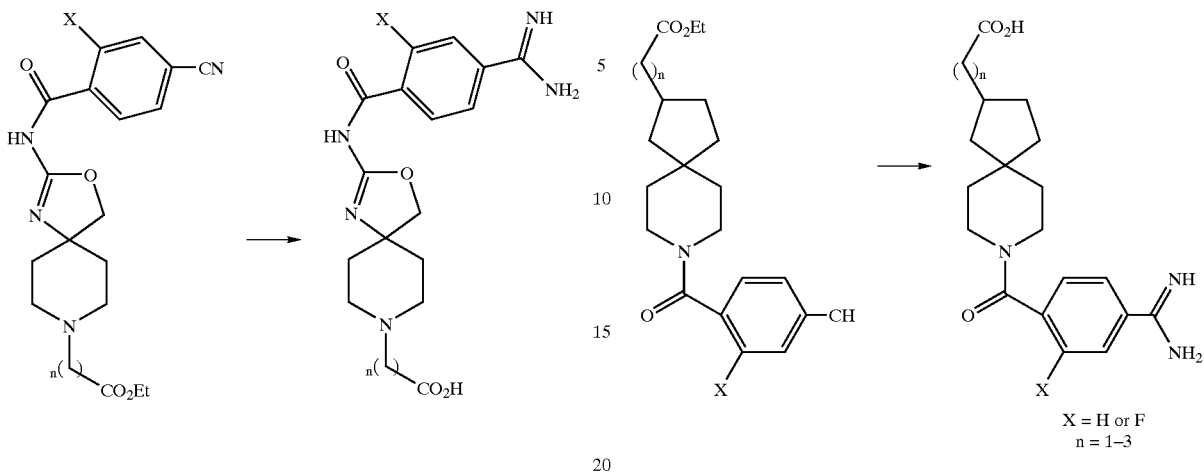

The Scheme 36 describes the synthesis of 2-benzoyl-3-oxa-1,8-diaza-spiro[4.5]dec-1-ene in which the nitrogen in the 2-position is benzoylated. The 2-amino spiro-oxazoline is acylated with 4-cyanobenzoyl chloride. The protecting group is removed with trifluoroacetic acid followed by alkylation with appropriate halogenated alkylester. After mild basic hydrolysis of ester, the nitrile is converted to amidino to give the desired product.

The Scheme 37 describes the synthesis of (8-benzoyl-aza-spiro[5.4]dec-3-yl)acetic acid derivatives. The reaction of N-benzyl-piperidone with diethyl lithiopyrrolidinomethyl phosphonate will give enamine. The enamine can be directly alkylated with 2-bromo-3-iodopropene, followed by aqueous hydrolysis to give the alkylated aldehyde. The hydrolysis of vinyl bromide can be readily achieved with mercuric acetate and boron trifluoride etherate in glacial acetic acid at room temperature (see S. F. Martin, and T. Chou, J. Org. Chem. 1978, 43, 1027). The γ-keto aldehyde will be treated with aqueous potassium hydroxide in methanol to afford cycloaldolization and dehydration to give the key intermediate spiro[4.5]dienone. The side chain is introduced by Horner-Emmons reaction with triethylphosphono acetate or triethyl phoshono propionate/sodium hydride. The bicyclic nucleus and the exo cyclic double bond are saturated and the protective group is removed by catalytic hydrogenation with palladium hydroxide on carbon. The subsequent acylation with 4-cyanobenzoyl chloride or (2-fluoro-4-cyanobenzoyl chloride), formation of amidine, and hydrolysis of the ester are carried out by methods described in the previous Schemes.

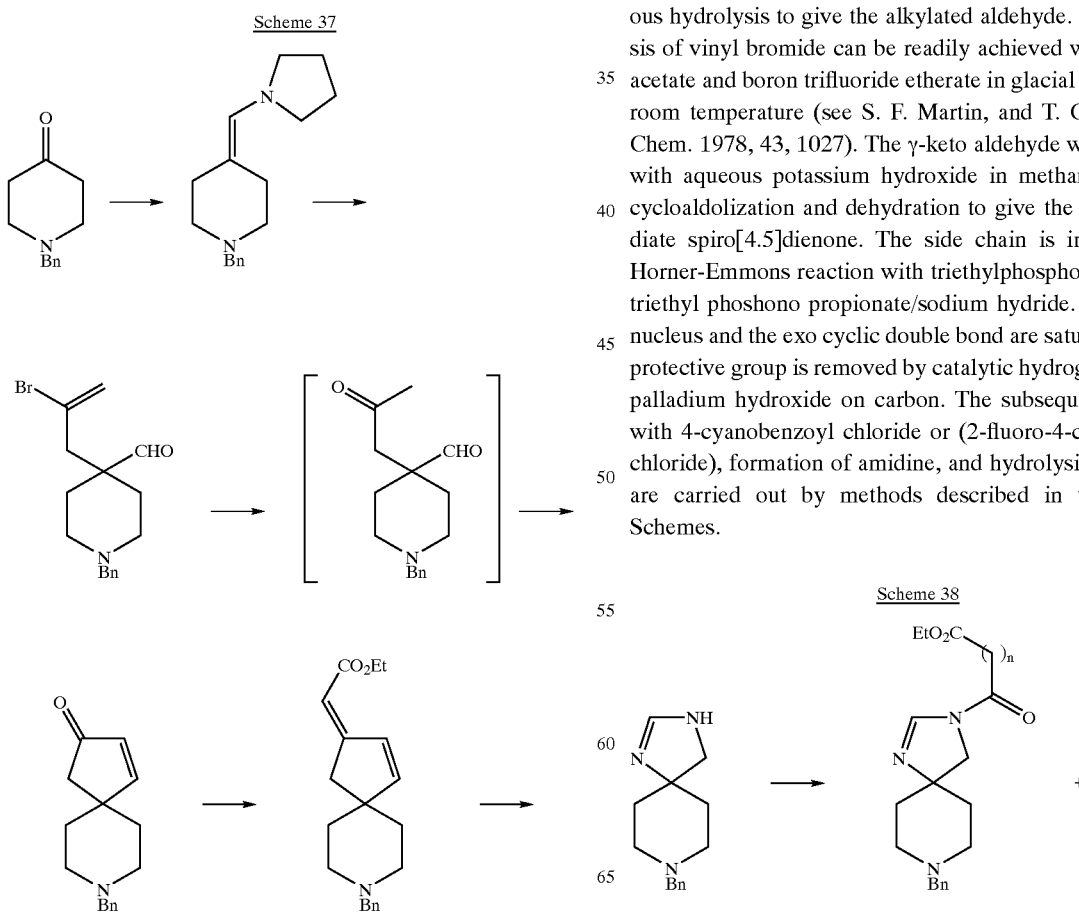

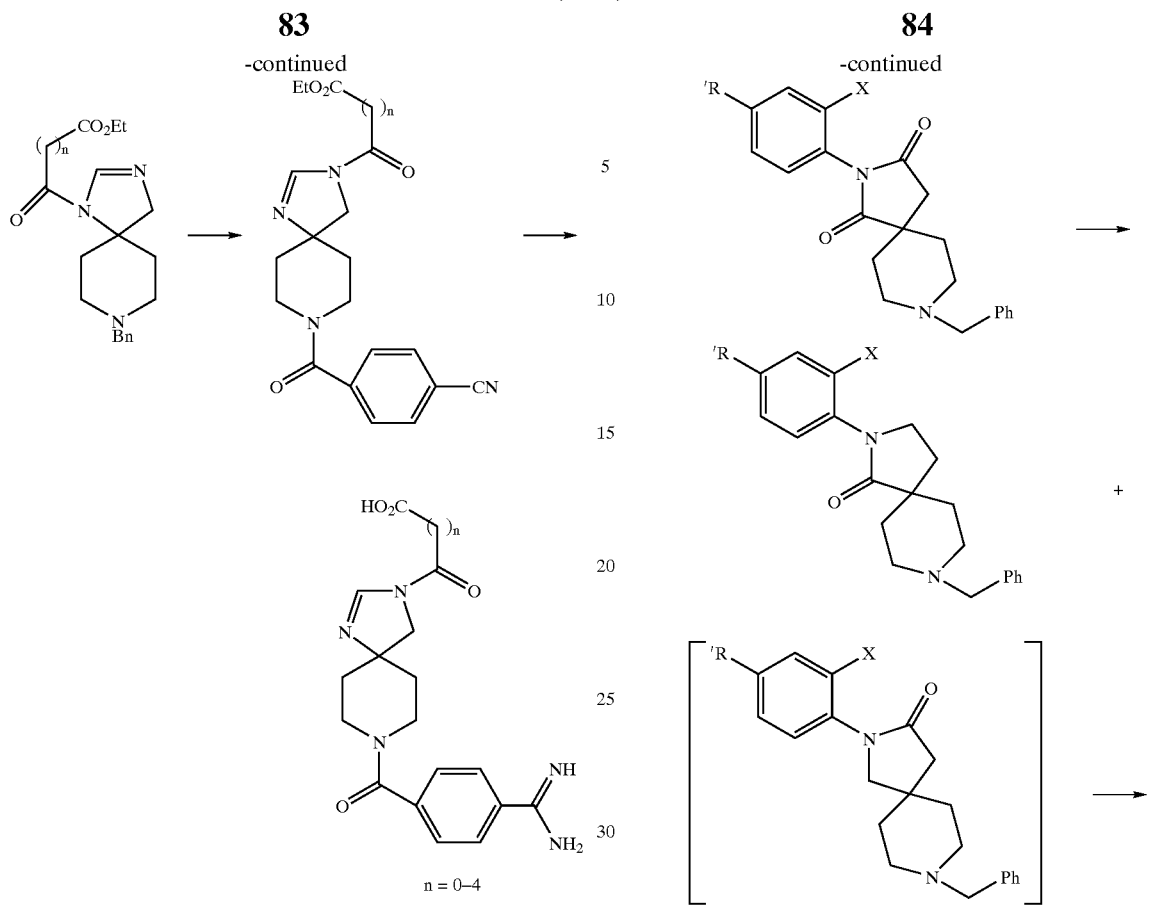

The Scheme 38 describes the synthesis 8-benzoyl-1-3-acyl-spiro[4.5]dec-1-en. The mono protected spiro-imidazoline from Scheme 33 is acylated with appropriate ester-acid chloride. The protecting group is removed followed with acylation with 4-cyanobenzoyl chloride (or 2-fluoro-4-cyanobenzoyl chloride) in presence of base such as triethylamine. After ester hyrolysis, the nitrile is converted to amidine funtionality as described in earlier schemes.

Scheme 39

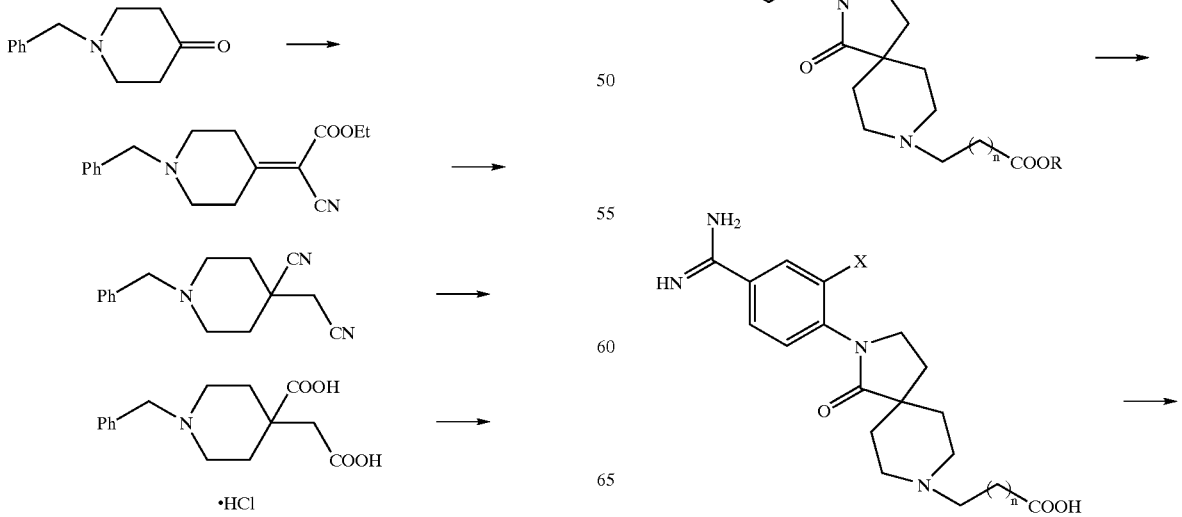

-continued
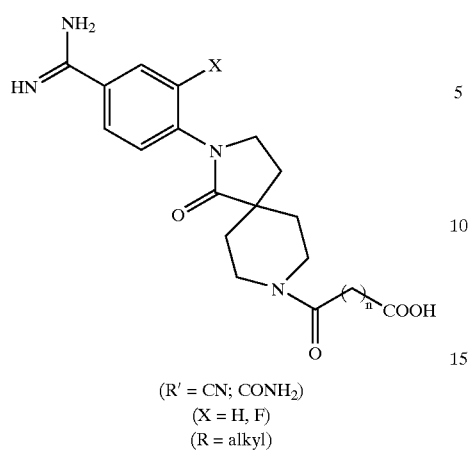
(R′ = CN; CONH₂)
(X = H, F)
(R = alkyl)
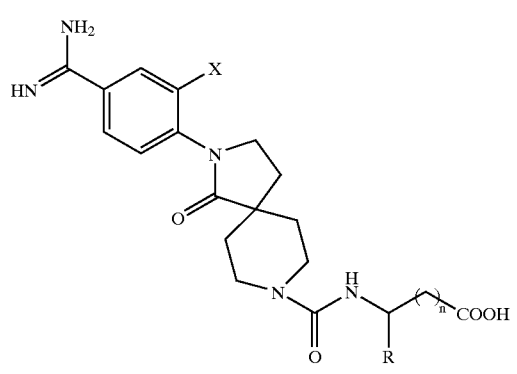
Scheme 40
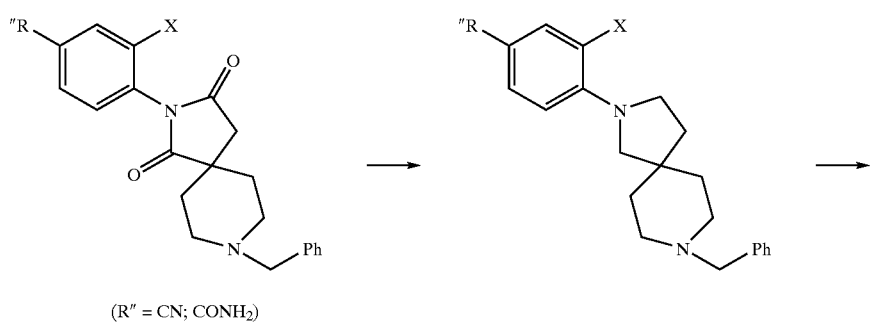
(R″ = CN; CONH₂)
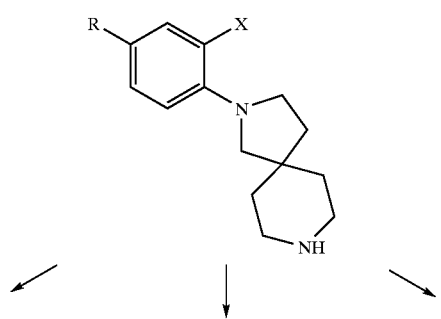

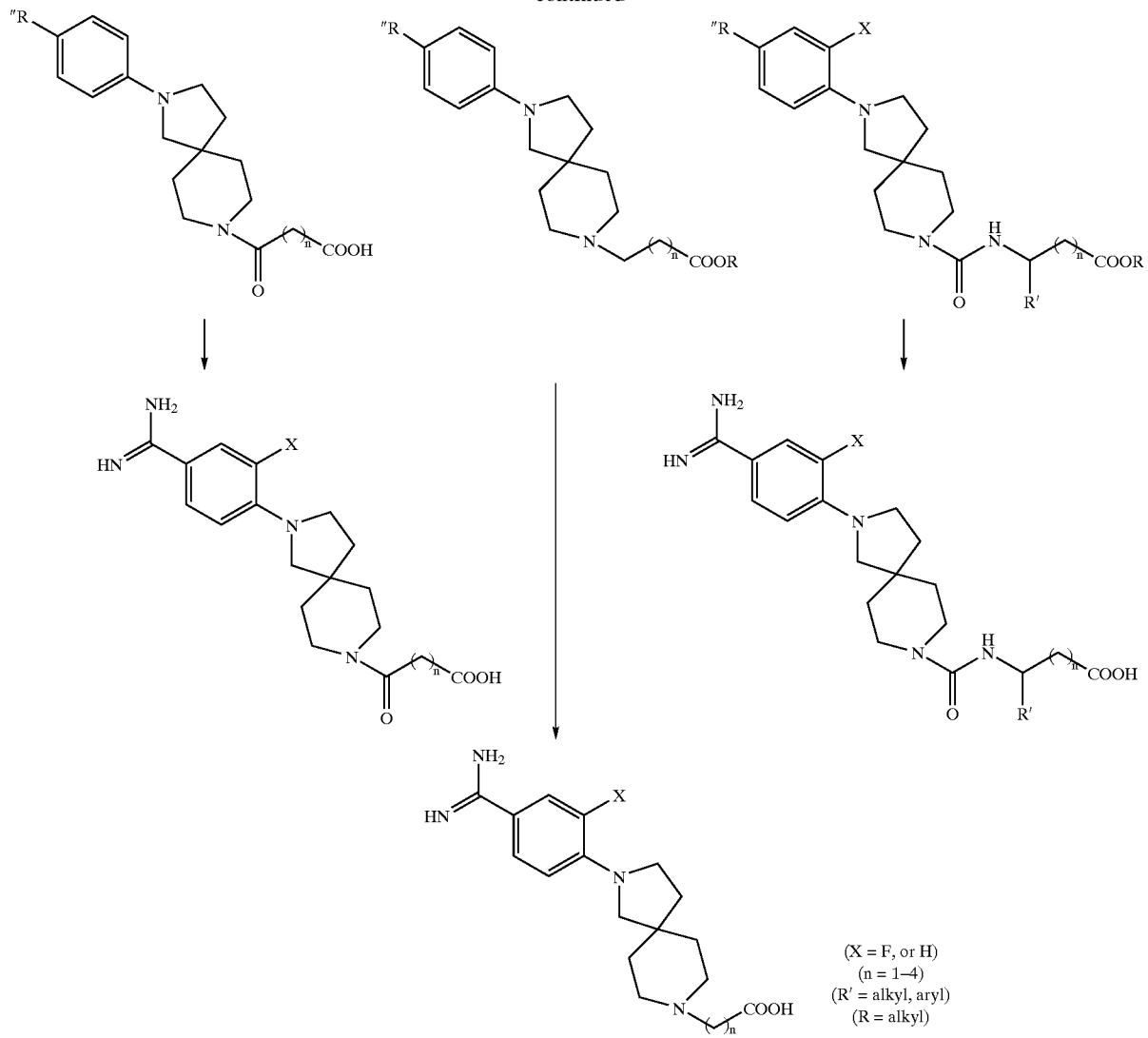

Scheme 40 describes the synthsis of a lactam. The imide was reduced with LiAlH$_4$ in THF to afford the amine. It was then N-debenzylated under hydrogenolysis conditions. The free piperidino compound was reacted with carboxy group bearing compounds as described before. De-protection of the carboxy groups followed by conversion of the cyano to amidino yielded the desired compounds.

Scheme 41

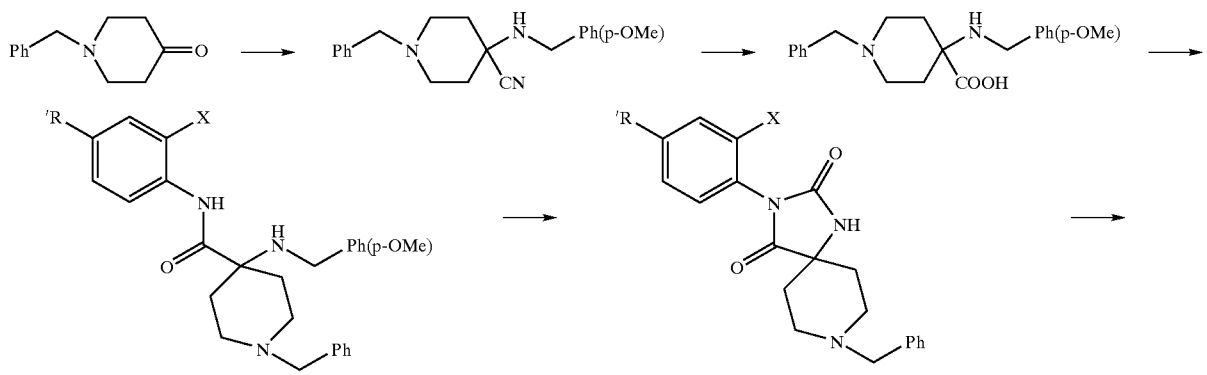

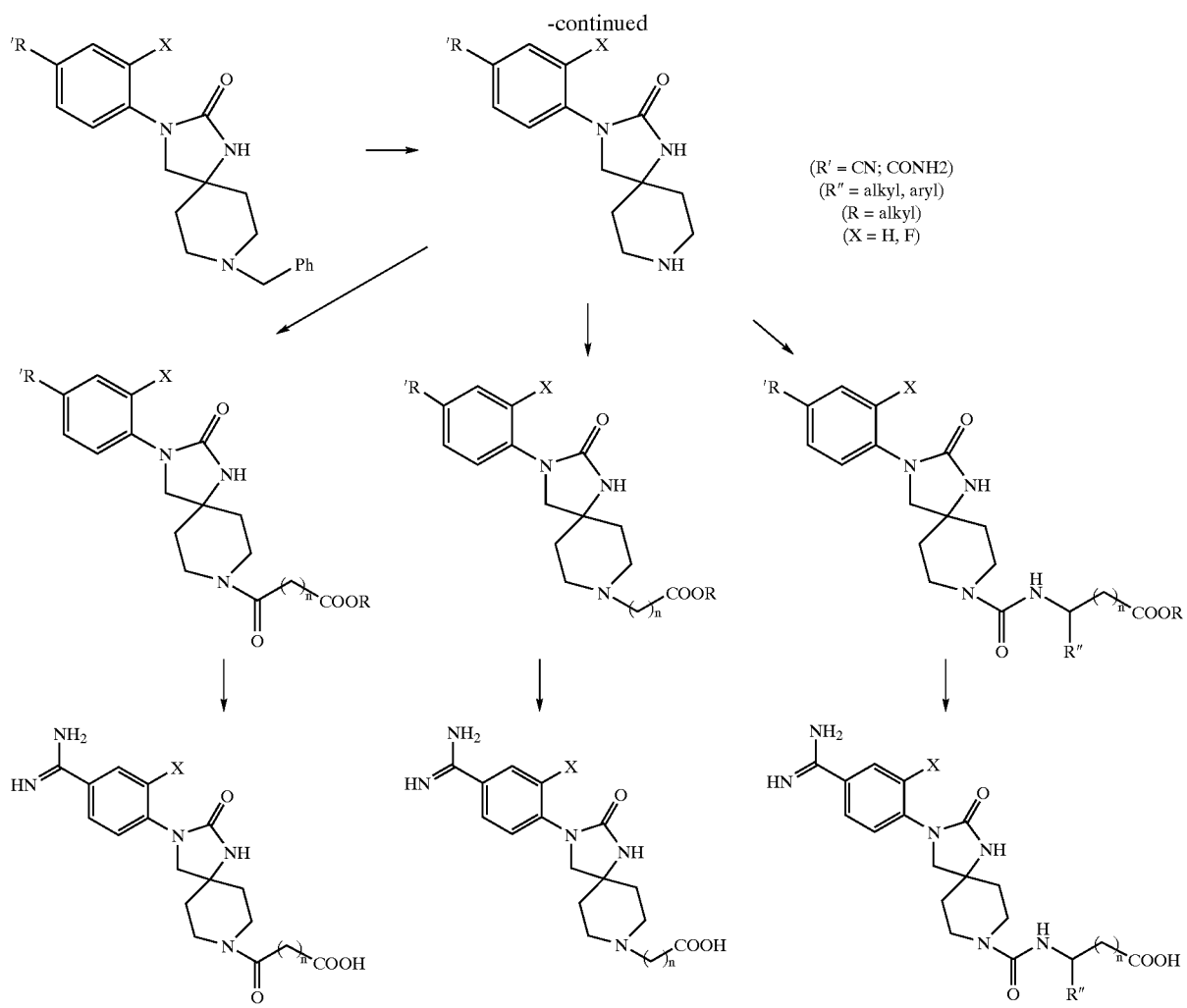

(R' = CN; CONH2)
(R'' = alkyl, aryl)
(R = alkyl)
(X = H, F)

Scheme 41 1-Benzylpiperidone was condensed with 4-methoxybenzylamine followed by reaction with potassium cyanide. The cyano group was hydrolysed by reaction with hot conc. HCl. Then it was coupled with 4-carboxyamido aniline to afford the amide. The 4-methoxy benzyl protective group was removed by reaction with DDQ, followed by reaction of the free amine with carbonyl diimidazole to give rise to urea derivative. N-Debenzylation was achieved under hydrogenolysis conditions, followed by coupling with carboxy group bearing synthons.

Scheme 42

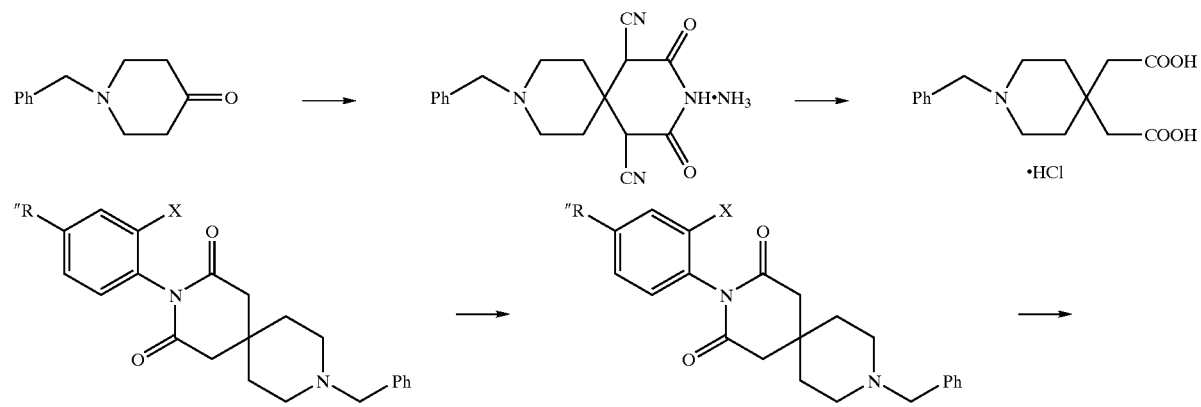

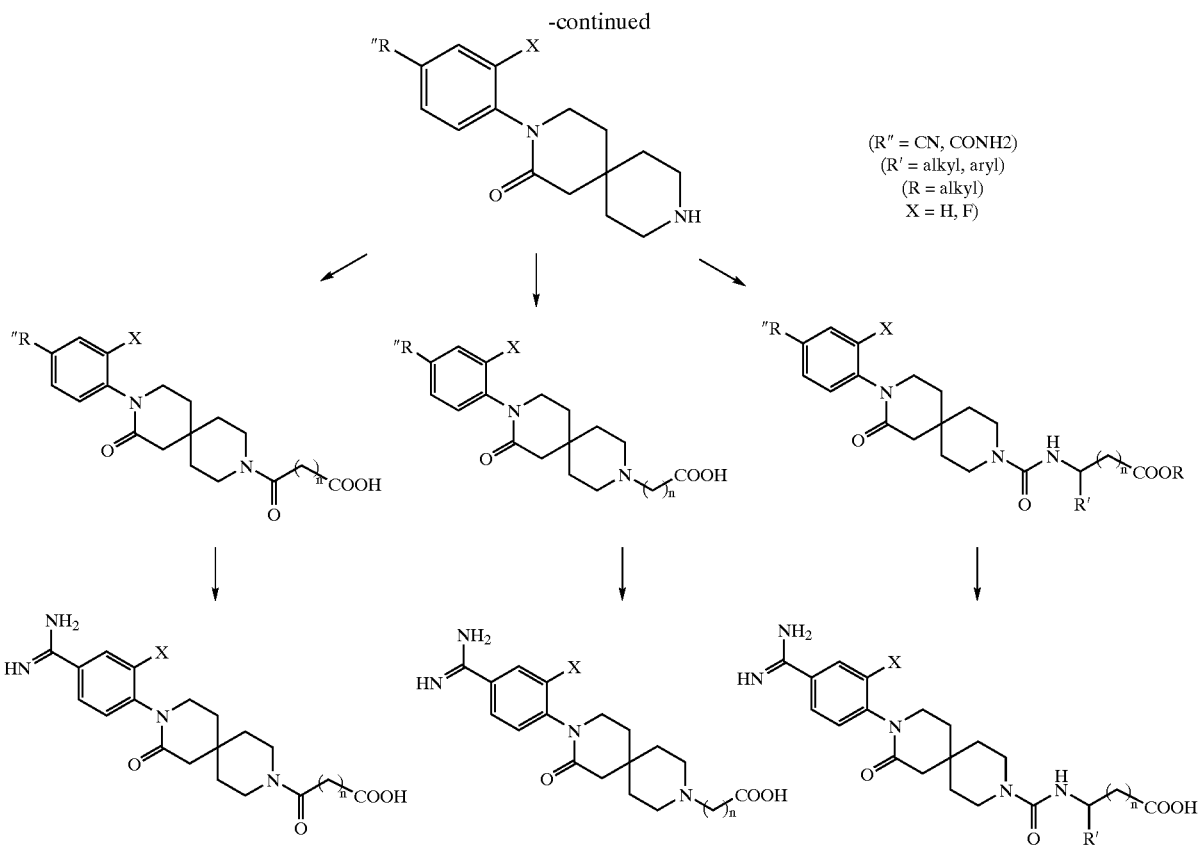

Scheme 42 1-Benzylpiperidone was condensed with ethyl cyanoacetate and ammonia in ethanol as described in the literature {S. M. McElvain, R. E. Lyle, Jr.; J. Amer. Chem. Soc. 72, 384 (1950)}. This was then treated with conc. Hcl at reflux for 3 days to afford the diacid, which was purified by its conversion to diethylester followed by hydrolysis back to diacid. This was then converted to the anhydride, and treated with 4-carboxyamido aniline as described in scheme 1 to afford the imide. This imide was converted to lactam by reaction with $NaBH_4$ as described in Scheme 39. The rest of the sequence was carried out as described elsewhere in this application.

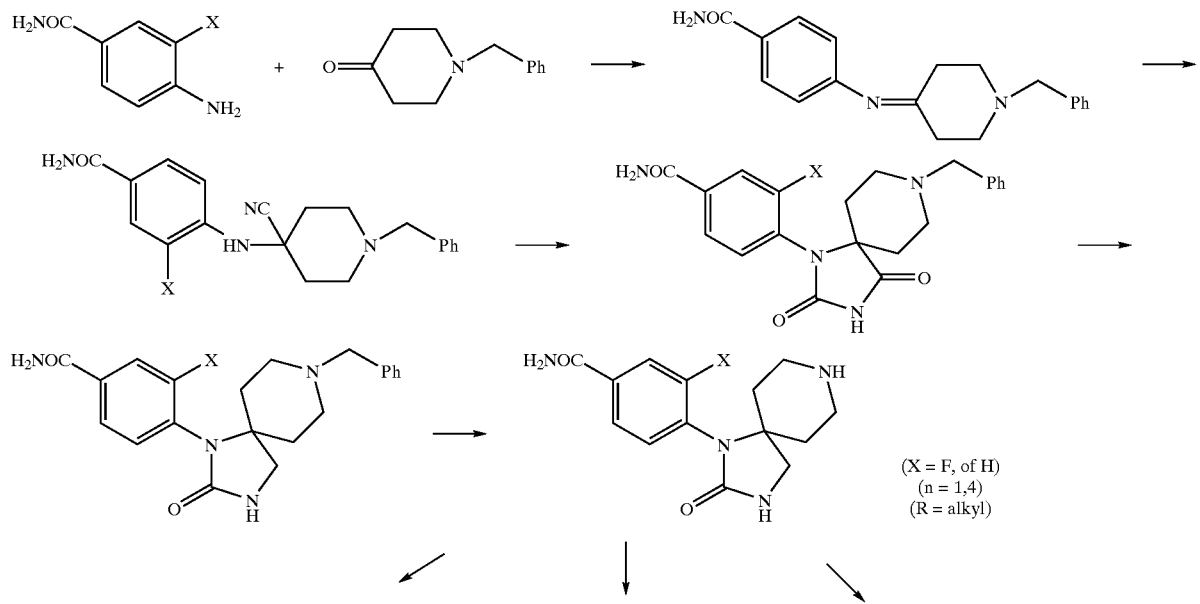

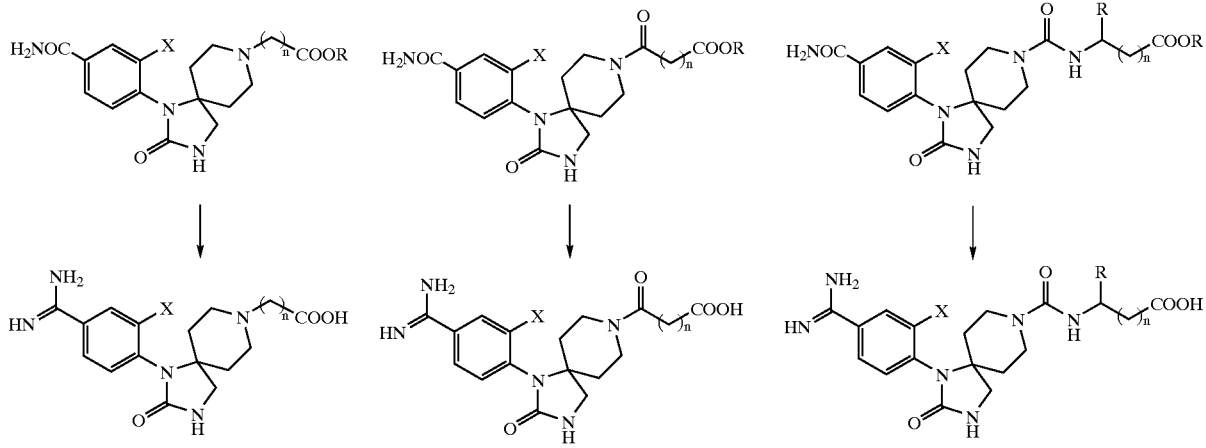
Scheme 43 1-Benzylpiperdone was coupled with 4-carboxyamide aniline, and the imide was reacted with potassium cyanide. This amine nitrile was reacted with potassium cyanate under acidic conditions to yield the hydantoin. The hydantoin functionality was reduced to urea by reaction with NaBH$_4$, as described before.
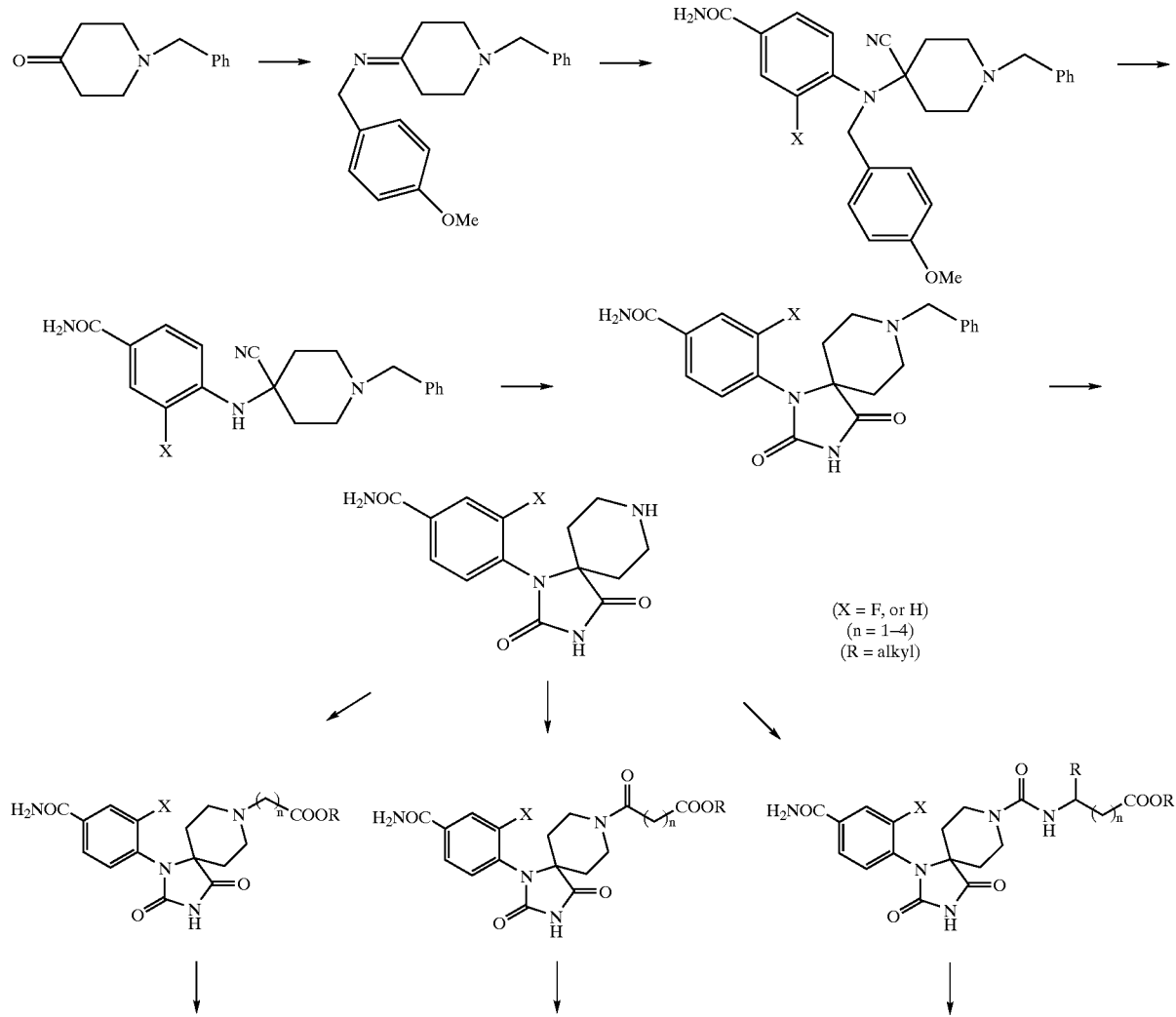
(X = F, or H)
(n = 1–4)
(R = alkyl)

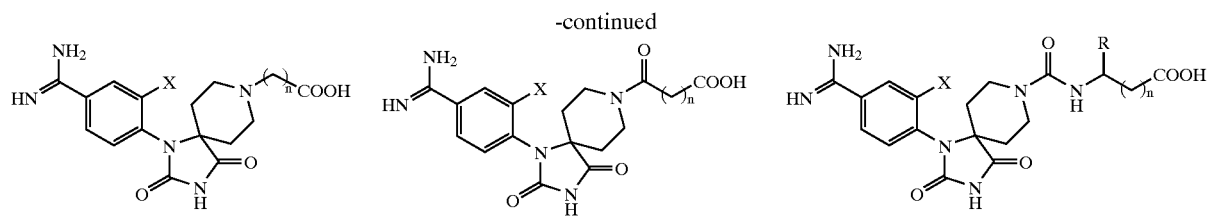

Scheme 44 1-Benzylpiperidone was coupled with 4-methoxy benzylamins, and the imine was then reacted with 4-carboxamide aniline to yield the amine nitrile. The 4-methoxy benzyl group was deprotected by reaction with DDQ. The free amine thus obtained was treated with potassium cyanate under acidic conditions to afford the hydantoin. The rest of the sequence is described elsewhere in this patent.

Scheme 45

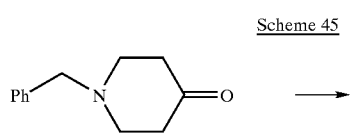

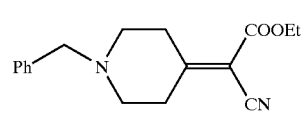

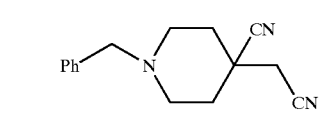

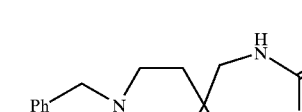

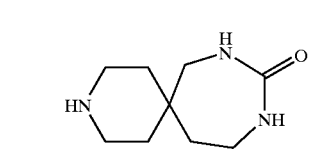

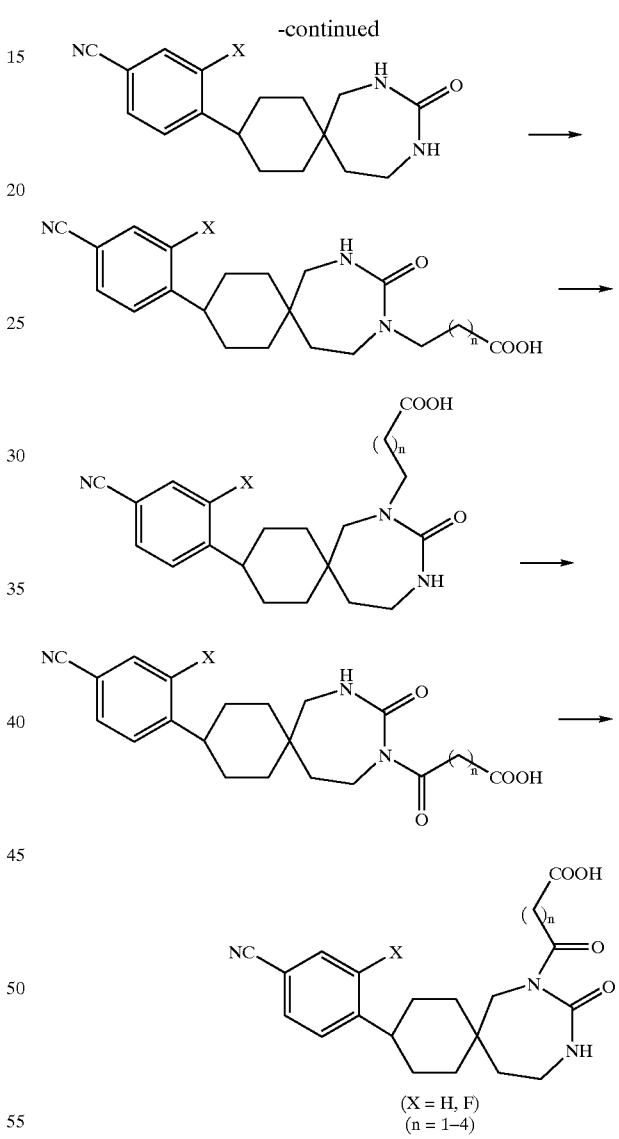

(X = H, F)
(n = 1–4)

Scheme 45 1-Benzylpiperidonewas coupled with ethyl cyanoacetate to afford the addition product, which was then reacted with potassium cyanide in ethanol/water at rellux to yield the dinitrile. It was reduced with LiAlH4 to afford the diamine. It was then reacted with carbonyl diimidazole to yield the 7-membered urea. This was subjected to N-debenzylation followed by coupling of the free piperidino compound with 4-cyano phenyl trflate under palladium catalysis. The rest of the sequence is described elsewhere.

Scheme 46

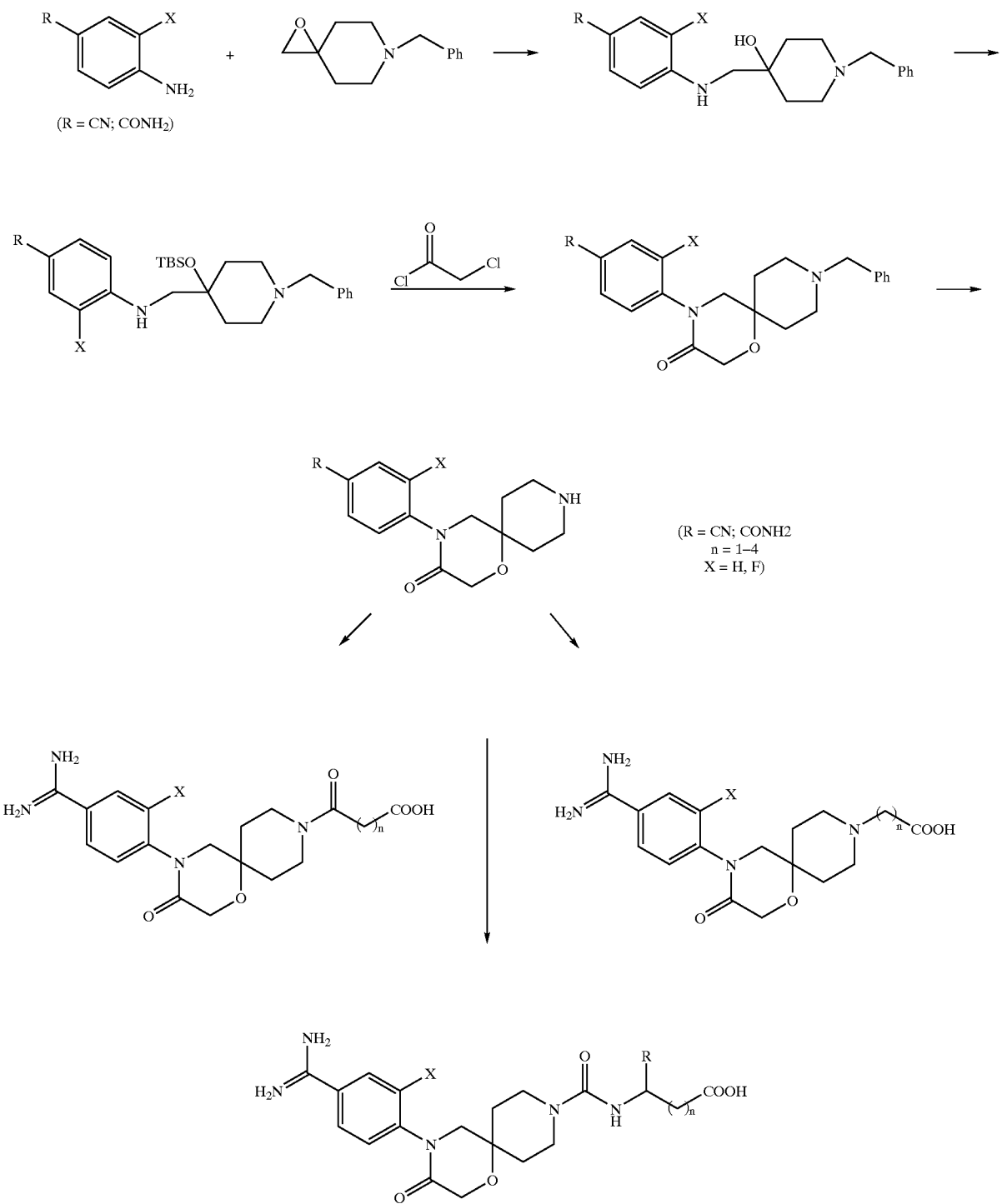

Scheme 46 4-carboxamide aniline was reacted with the epoxide (synthesis of it is described elsewhere in this application) to afford the aminol. The hydroxy group was protected as tert-butyl dimethylsilyl ether, and the amine was then reacted with chloro acetyl chloride. Then the TBS protective group was removed and the free hydroxy compound was cyclized to yield the spiro compound. The rest of the steps are identical to procedures described in other schemes The following Examples illustrate the practice of the invention.

EXAMPLE 1

Preparation of Ethyl (3-(4-(Aminoiminomethyl)benzoyl)-3-aza-spiro[5.5]undec-9-yl)acetate Hydrochloride

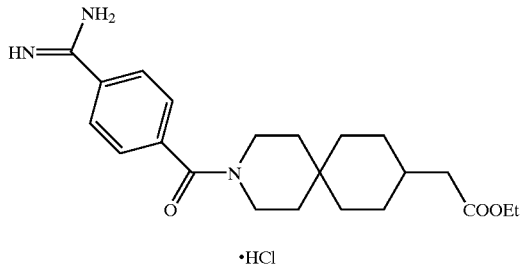

·HCl

Step A: Preparation of Benzyl 9-oxo-3-aza-Spiro[5.5]undec-7-ene-3-carboxylate

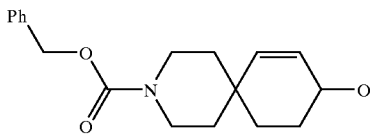

A solution of 0.98 g (3.96 mmol) benzyl 4-formylpiperidine-1-carboxylate (prepared by the method from Eur. J. Med. Chem. 1991, 26, 625) and 0.28 g (4.0 mmol) 3-buten-2-one in a mixture of 1 ml methanol and 1 ml water was added dropwise to a boiling solution of 0.015 g (0.27 mmol) potassium hydroxide in 1 ml methanol. After 1 hour heating with reflux the cooled mixture was poured into 50 ml water, and it was extracted with tert.-butylmethylether. The organic layer was dried over sodium sulfate and concentrated under reduced pressure. The title compound was obtained from the remaining oil by HPLC on silica gel with hexane/acetone 4:1.

yield: 0.23 g (19%) oil.

Step B: Preparation of Benzyl 9-((Ethoxycarbonyl)methylene)-3-aza-spiro[5.5]undec-7-ene-3-carboxylate

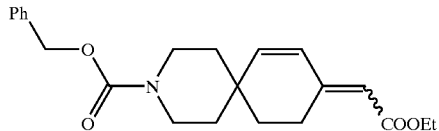

23.63 g (105.4 mmol) diethyl ethoxycarbonylmethylphosphonate were dissolved in 500 ml dry THF and the solution was kept under an atmosphere of nitrogen. After addition of 3.07 g (102.3 mmol) 80% sodium hydride in mineral oil the mixture was stirred for 30 min at 0° C. A solution of 30.0 g (100.2 mmol) of the spiro compound from the previous step in 33 ml dry THF was added dropwise, and it was stirred for 4 hours with warming to room temperature. The mixture was poured into water, and it was extracted with tert.-butylmethylether. The organic layer was washed two times with water and dried over sodium sulfate, and the solvent was removed in vacuo. The title compound was purified by chromatography on silica gel with hexane/acetone 4:1 and obtained in five oily fractions each of them containing some impurities. They were combined and used for the next step.

Total yield: 10.58 g (29%).

Step C: Preparation of Ethyl (3-aza-Spiro[5.5]undec-9-yl)acetate

9.6 g (26.0 mmol) of the protected spiro compound from Step B were dissolved in 400 ml ethanol, and the solution was filled into a hydrogenation vessel followed by 2 g Pd(II) hydroxide on charcoal. The reaction was carried out at 40° C. and 1 atm hydrogen, and it was complete after about 40 hours. The catalyst was removed by filtration through silica gel, and the filtrate was concentrated under reduced pressure. The remaining oil was treated with dry ether, filtered, and the filtrate was acidified with ethereal hydrochloric acid. The hydrochloride of the title compound was collected by filtration, washed two times with ether, dissolved in water, and the solution was made alkaline with 2 N aqueous sodium hydroxide solution. After extraction with dichloromethane the organic layer was dried over sodium sulfate and concentrated in vacuo.

yield: 3.43 g (55%) oil.

Step D: Preparation of Ethyl (3-(4-Cyanobenzoyl)-3-aza-spiro[5.5]undec-9-yl)acetate

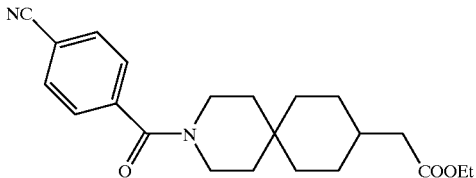

0.24 g (1.0 mmol) of the compound from the previous step and 0.6 ml dry pyridine were dissolved in 7 ml dry THF. The solution was kept below 5° C., while 0.165 g (1.0 mmol) 4-cyanobenzoyl chloride in 6 ml dry THF were added dropwise within 15 min. After 2 hours stirring at room temperature it was concentrated under reduced pressure. The residue was treated with water and extracted with ethyl acetate. The organic layer was washed with diluted aqueous Cu(II) sulfate solution, dried over sodium sulfate, and the solvent was removed in vacuo. The title compound was obtained by HPLC on silica gel with hexane/acetone 4:1 followed by 3:1.

yield: 0.19 g (51%) yellow oil.

Step E: Preparation of Ethyl (3-(4-(Aminoiminomethyl)benzoyl)-3-aza-spiro[5.5]undec-9-yl)acetate Hydrochloride A solution of 1.65 g (4.48 mmol) of the nitrile from the previous step in 75 ml ethanol was kept below 5° C. and saturated with gaseous hydrogen chloride. It was stirred over night at room temperature until the reaction was complete. and the solvent was removed under reduced pressure to give the crude intermediate imidoester. It was treated with 50 ml 12% ethanolic ammonia solution and stirred for two days at room temperature. The mixture was concentrated in vacuo, and the residue was stirred with 10 ml dichloromethane. Remaining solids were removed by filtration, and the solvent was evaporated from the filtrate under reduced pressure. The crude title amidine was obtained by chromatography on silica gel with dichloromethane containing between 5% and 10% ethanol. It solidified by stirring several times with ether, and it was further purified by HPLC using the same eluent.

yield: 0.18 g (9.5%) colorless crystals, m.p.>300° C.
ELISA: $IC_{50}$>10 µM PRP (ADP): $IC_{50}$=100 µM.

EXAMPLE 2

Preparation of (3-(4-(Aminoiminomethyl)benzoyl)-3-aza-spiro[5.5]undec-9-yl)acetic Acid Hydrochloride

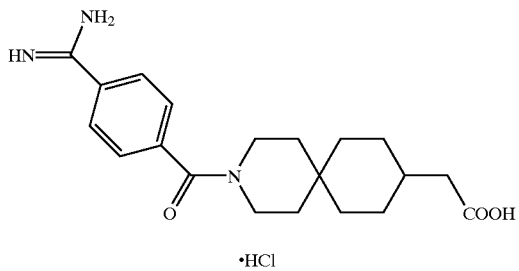

·HCl 70 mg (0.166 mmol) of the ester from Example 1 were treated with 2 ml 2 N aqueous hydrogen chloride and 5 ml water. After heating for 4 hours at 60° C. the solvent was removed under reduced pressure, and the remaining title acid was stirred with tert.-butylmethylether, collected by filtration, and dried in vacuo.

yield: 64 mg (98%) beige hygroscopic solid; ELISA: $IC_{50}=0.0082$ μM PRP (ADP): $IC_{50}=0.41$ μM

EXAMPLE 3

Preparation of Ethyl 4-(3-(4-(Aminoiminomethyl)phenyl)-2-oxo-1-oxa-3,8-diaza-spiro[4.5]dec-8-yl)butanoate Hydrochloride

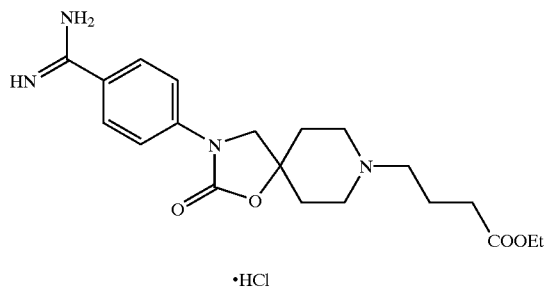

·HCl

Step A: Preparation of Benzyl 4-(N-(4-Cyanophenyl)amino)methyl)-4-hydroxypiperidine-1-carboxylate

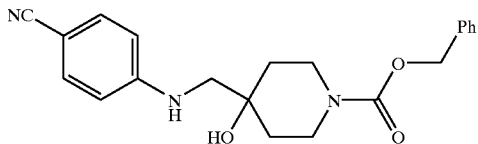

A mixture of 20.0 g (80.9 mmol) benzyl 1-oxa-6-aza-spiro[2.5]octane-6-carboxylate (prepared from the protected piperidone and dimethylsulfoxonium methylide according to J. Med. Chem. 1983, 26, 855; U.S. Pat. No. 4,353,901) and 47.0 g (397.8 nmmol) 4-aminobenzonitrile were heated at 160° C. for 30 hours until no starting epoxide could be detected by TLC. It was cooled to room temperature, and the excess of the aniline was removed by chromatography on silica gel with dichloromethane. The title compound was obtained after 4 enhancing the polarity of the eluent by addition of 5% ethanol.

yield: 24.5 g (83%) beige crystalline solid, m.p. 107–108° C.

Step B: Preparation of Benzyl (3-(4-Cyanophenyl)-2-oxo-1-oxa-3,8-diaza-spiro[4.5]dec-8-yl)carboxylate

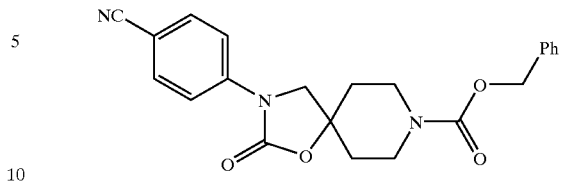

A solution of 18.5 g (50.6 muol) of the piperidine from Step A and 11.45 g (70.6 mmol) N,Ni-carbonyldiimidazole in 210 ml dry THF were heated with reflux for 8 hours under an atmosphere of argon. After addition of another 5.0 g (30.8 mmol) carbonyldiimidazole heating was continued overnight. The solvent was removed under reduced pressure, and the title compound was obtained by chromatography on silica gel with dichloromethane. It solidified from the combined pure fractions by stirring with hexane, was filtered, and dried in vacuo.

yield: 5.3 g (27%) pale yellow powder, m.p. 138–140° C.

Step C: Preparation of 4-(2-oxo-1-oxa-3,8-Diaza-spiro[4.5]dec-3-yl)benzonitrile Trifluoroacetate

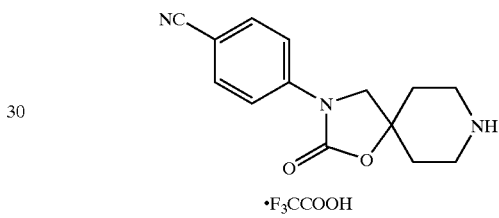

·F₃CCOOH 4.26 g (10.88 mmol) of the protected spiro compound from the previous step were added in small portions to 26 ml trifluoroacetic acid, while the temperature was kept below 10° C. After two days stirring at room temperature the mixture was poured into ice water and neutralized with sodium bicarbonate. It was treated with dichloromethane, and a precipitate of the title compound was formed between the two layers, which was collected by filtration and dried in vacuo.

yield: 4.0 g (99%) colorless crystals, m.p. 217–220° C.

Step D: Prepatation of Ethyl 4-(3-(4-Cyanophenyl)-2-oxo-1-oxa-3,8-diaza-spiro[4.5]dec-8-yl)butanoate

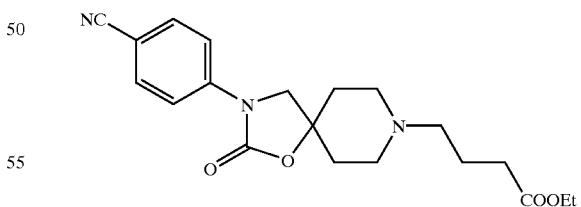

3.0 g (8.08 mmol) of the piperidine from the previous step were dissolved in 50 ml dry acetone followed by addition of 1.68 g (15.85 mmol) sodium carbonate and 1.56 g (8.00 mmol) ethyl 4-bromobutanoate. The mixture was heated with reflux is overnight, cooled to room temperature, and the inorganic solids were removed by filtration. The filtrate was concentrated under reduced pressure, and the title compound was obtained from the residue by chromatography on silica gel with dichloromethane/ethanol 40:1 and 20:1. The combined pure fractions solidified, and the crystalline ester was dried in vacuo at 50° C.

yield: 2.4 g (81%) colorless crystals, m.p. 78–80° C.

Step E: Prepatation of Ethyl 4-(3-(4-(Ethoxycarbonimidoyl) phenyl)-2-oxo-1-oxa-3,8-diaza-spiro[4.5]dec-8-yl) butanoate hydrochloride

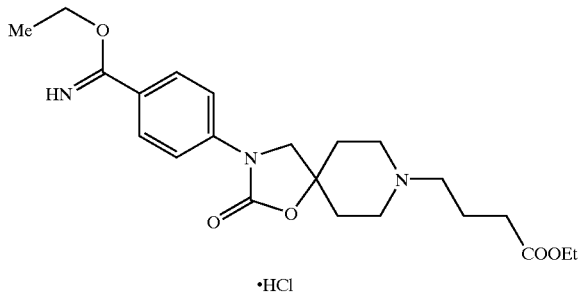
•HCl

A suspension of 2.4 g (6.46 mmol) of the nitrile from Step D in 140 ml dry ethanol was saturated with gaseous hydrogen chloride, while the temperature was kept below 10° C. It was stirred overnight at room temperature, and the solvent was removed under reduced pressure. The title intermediate crystallized by stirring with hexane. It was filtered with suction and dried in vacuo.

yield: 2.2 g (75%) pale yellow powder, m.p. 195–199° C.

Step F: Prepatation of Ethyl 4-(3-(4-(Aminoiminomethyl) phenyl)-2-oxo-1-oxa-3,8-diaza-spiro[4.5]dec-8-yl) butanoate hydrochloride 2.2 g (4.85 mmol) of the intermediate from the previous step were suspended in 130 ml saturated ethanolic ammonia solution. It was stirred overnight at room temperature, and after addition of another 30 ml ammonia solution stirring was continued for another day. The solvent was removed under reduced pressure., and the title amidine was obtained by chromatography on silica gel with dichloromethane/ethanol 2:1. It crystallized by stirring with tert.-butylmethylether, was filtered with suction, and dried in vacuo at 50° C.

yield=0.55 g (27%), white powder, m.p. 127–129° C.; ELISA: not tested PRP (ADP): not tested.

EXAMPLE 4

Preparation of 4-(3-(4-(Aminoiminomethyl)phenyl)- 2-oxo-1-oxa-3,8-diaza-5 spiro[4.5]dec-8-yl)butanoic Acid Bistrifluoroacetate

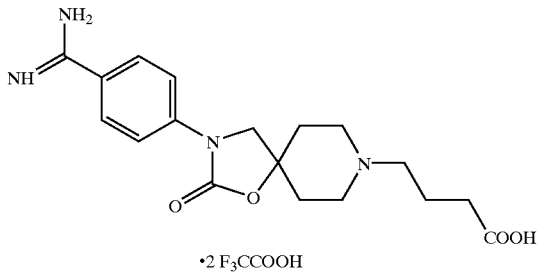
•2 F₃CCOOH

Step A: Preparation of tert.-Butyl 4-(3-(4-Cyanophenyl)-2-oxo-1-oxa-3,8-diaza-spiro[4.5]dec-8-yl)butanoate

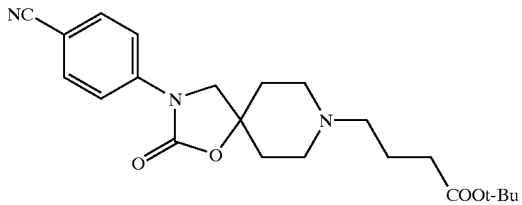

10.0 g (26.9 mmol) of the intermediate from Example 3, Step C were dissolved in 250 ml dry acetone followed by addition of 5.7 g (53.8 mmol) sodium carbonate and 4.81 g (26.9 mmol) tert.-butyl 4-chlorobutanoate (prepared according to Chem. Ber. 1965, 98, 2312). It was heated with reflux overnight. After addition of another 2.85 g (26.9 mmol) sodium carbonate and 2.4 g (13.4 mmol) of the tert.-butyl ester heating was continued for another day. The inorganic solids were removed by filtration, and the filtrate was concentrated under reduced pressure. The title nitrile was obtained as an oil, which solidified upon standing after chromatographic purification on silica gel with dichloromethane/ethanol 5 40:1 and 20:1.

yield: 1.87 g (17%) beige amorphous solid, m.p. 92–94° C. 4-((tert.-Butoxycarbonylamino)iminomethyl)phenyl)-2-oxo-1-oxa-3,8-diaza-spiro[4.5]dec-8-yl)butanoate

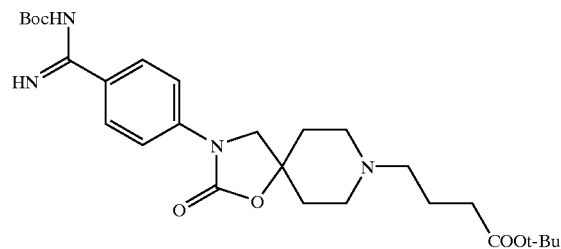

A steady stream of gaseous hydrogen sulfide was passed through a solution of 1.8 g (4.5 mmol) of the nitrile from the previous step in 67.5 ml dry pyridine and 7.2 ml triethylamine for about 1 hour. After stirring over night the conversion to the thioamide was complete. The mixture was poured into water and extracted three times with ethyl acetate. The combined organic layers were dried over sodium sulfate, and concentrated in vacuo. It was dissolved in 100 ml toluene, evaporated again under reduced pressure, and this procedure was repeated for two times to remove remaining pyridine.

The crude thioamide was suspended in 22.5 ml acetone followed by dropwise addition of 2.25 ml methyl iodide. It was stirred for 1 hour at room temperature, while the mixture became a clear solution, and evaporated to dryness in vacuo. The residue was treated with 18 ml methanol followed by 1.35 g (17.5 mmol) ammonium acetate, and the mixture was heated for 3 h at 60° C. After evaporation under reduced pressure the remaining oil was stirred two times with tert.-butylmethylether to leave the crude crystalline amidine.

It was added to the amidine a mixture of 45 ml THF/water 1:1 followed by 4.05 g (29.3 mmol) potassium carbonate and 4.5 g (20.6 mmol) Boc₂O. After 45 min. stirring at room temperature it was diluted with 50 ml water and extracted with ethyl acetate. The organic layer was dried over sodium sulfate and concentrated under reduced pressure. The title compound was obtained by chromatography on silica gel with dichloromethane/ethanol 20:1 followed by another chromatographic purification with dichloromethane/ethanol 40:1.

yield: 0.2 g (8.6%) yellow oil.

Step C: Preparation of 4-(3-(4-(Aminoiminomethyl)phenyl)-2-oxo-1-oxa-3,8-diaza-spiro[4.5]dec-8-yl)butanoic Acid Bistrifluoroacetate 0.2 g (0.39 mmol) of the protected amidine from Step B were treated with 2 ml trifluoroacetic acid, and the mixture was stirred at room temperature for 2 hours. It was evaporated to dryness in vacuo, and the solid residue was stirred several times with ether and with hexane. The title acid was collected by filtration and dried at 50° C. in vacuo.

yield: 0.12 g (53 1), beige crystalline solid, m.p. 122–125° C.; ELISA: not tested PRP (ADP): $IC_{50}$=3 μM.

EXAMPLE 5

Preparation of Ethyl (3-(4-(Aminoiminomethyl)phenyl)-1-oxa-2,8-diaza-spiro[4.5]dec-2-en-8-yl)acetate Hydrochloride

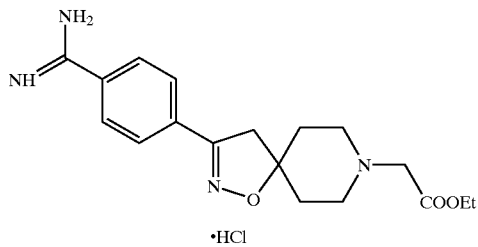

·HCl

Step A: Prepatation of tert.-Butyl (3-(4-Cyanophenyl)-1-oxa-2,8-diaza-spiro[4.5]dec-2-en-8-yl)carboxylate

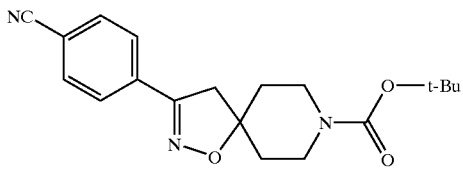

4-Cyanobenzohydroximinoyl chloride was prepared by chlorination of 4-cyanobenzaldehyde oxime with N-chlorosuccinimide according to the procedure from J. Org. Chem. 1980, 45, 3916 and tert.-butyl 4-methylenepiperidine-1-carboxylate according to the procedure from Int. Pat. Appl. WO 94/13696.

To a solution of 15.82 g (80.2 mmol) of the piperidine and 14.48 g (80.2 mmol) of the hydroximinoyl chloride in 150 ml dry methanol was added dropwise the same volume of a methanolic solution of 17.8 ml triethylamine, while the temperature was kept below 28° C. After stirring at room temperature for two days another 8.7 g (48.2 mmol) of the hydroximinoyl chloride and 10.7 ml triethylamine were added in three equal portions, each after a period of 2 hours. It was stirred over night, and the precipitate of the title compound was collected by filtration and washed with methanol. The crystals were stirred with tert.-butylmethylether, filtered with suction, and dried in vacuo. The combined filtrates were poured into water and extracted three times with tert.-butylmethylether. The combined extracts were dried over sodium sulfate, concentrated under reduced pressure to leave another crop of the title compound, which was washed with a small amount of methanol and dried in vacuo.

total yield: 26.0 g (95%) white powder, m.p. 169–171° C.

Step B: Preparation of 4-(1-oxa-2,8-Diaza-spiro[4.5]dec-2-en-3-yl)benzonitrile

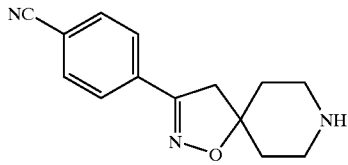

10.0 g (29.3 mmol) of the protected piperidine from the previous Step were added in small portions to 25 ml trifluoroacetic acid, while the temperature was maintained below 30° C. After 3 hours stirring at room temperature the mixture was carefully poured into saturated aqueous sodium bicarbonate solution and stirred for 20 min. A first crop of the title piperidine precipitated from the mixture and was collected by filtration, dried in vacuo at 40° C., stirred with ethyl acetate, and filtered again. The aqueous filtrate was adjusted to pH 11 with 2 N sodium hydroxide solution and extracted four times with ethyl acetate. The combined organic layers were dried over sodium sulfate, and two other crops were formed by gradual concentration under reduced pressure, which were washed with a small amount of ethyl acetate and filtered with suction.

total yield: 6.94 g (98%) colorless crystals, m.p.>199° C. (dec.).

Step C: Prepatation of Ethyl (3-(4-Cyanophenyl)-1-oxa-2,8-diaza-spiro[4.5]dec-2-en-8-yl)acetate

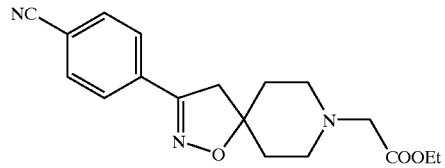

0.6 g (2.5 mmol) of the piperidine from Step B were dissolved in a mixture of 10 ml dry DMF and 10 ml dry ethanol followed by addition of 0.69 g (5.0 mmol) potassium carbonate. After 30 min stirring 0.42 g (2.5 mmol) ethyl bromoacetate were added dropwise, and the mixture was stirred overnight at room temperature. It was poured into water and extracted two times with ethyl acetate. The combined organic layers were washed two times with water, dried over sodium sulfate, and concentrated under reduced presure. The title compound was obtained from the residue by chromatography on silica gel with hexane/acetone 3:2 as an oil, which solidified upon standing.

yield: 0.52 g (64%) pale yellow crystals, m.p. 116–118° C.

Step D: Prepatation of Ethyl (3-(4-(Aminoiminomethyl)phenyl)-1-oxa-2,8-diaza-spiro[4.5]dec-2-en-8-yl)acetate Hydrochloride A solution of 0.5 g (1.53 mmol) of the nitrile from the previous Step in 35 ml dry ethanol was saturated with gaseous hydrogen chloride at 0° C. The mixture was stirred overnight at room temperature, concentrated under reduced pressure, and treated with 40 ml of a saturated ethanolic solution of ammonia. After stirring over night another 10 ml of the ammonia solution were added, and the reaction was brought to completion by standing at room temperature for another two days. The solvent was removed in vacuo, and the remaining solid title compound was purified by stirring with ethyl acetate, filtration, and chromatography on silica gel with dichloromethane/methanol 4:1.

yield: 0.23 g (40%), white powder; m.p.>254 Oc (dec.); ELISA: not tested PRP (ADP): not tested.

EXAMPLE 6

Preparation of (3-(4-(Aminoiminomethyl)phenyl)-1-oxa-2,8-diaza-spiro[4.5]dec-2-en-8-yl)acetic Acid

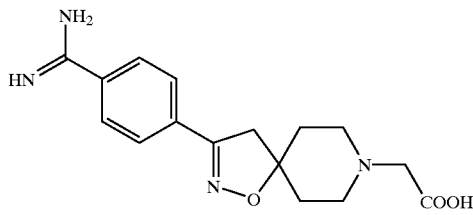

0.12 g (0.315 mmol) of the ester from Example 5 were dissolved in 2 ml ethanol, and after addition of 0.4 ml 2 N aqueous sodium hydroxide solution the mixture was stirred overnight at room temperature. It was adjusted to pH 4 with diluted acetic acid. The solvent was removed from the clear solution under reduced pressure to leave a brown oil, which solidified by stirring with a mixture of ethanol and water. It was filtered, stirred in a small amount of hot ethanol, filtered again, and dried in vacuo.

yield: 88 mg (88%) colorless amorphous solid, m.p.>265° C., ELISA: not tested PRP (ADP): $IC_{50}$=4 µM.

EXAMPLE 7

Preparation of Ethyl 4-(3-(4-(Aminoiminomethyl)phenyl)-1-oxa-2,8-diaza-spiro[4.5]dec-2-en-8-yl)butanoate Hydrochloride

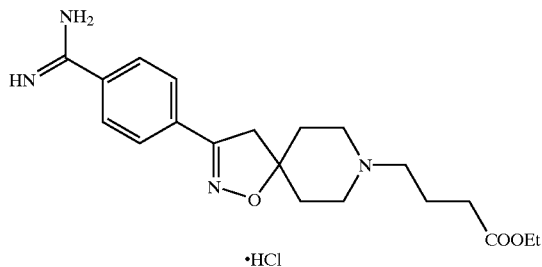

Step A: Prepatation of Ethyl 4-(3-(4-Cyanophenyl)-1-oxa-2,8-diaza-spiro[4.5]dec-2-en-8-yl)butanoate

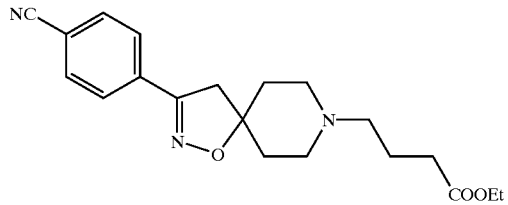

1.2 g (5.0 1mol) of the piperidine from Example 5, Step B, 1.37 g (9.9 mmol) potassium carbonate, and a catalytic amount of potassium iodide were suspended in 30 ml dry acetone followed by addition of 0.99 g (5.1 mmol) ethyl 4-bromobutanoate. The mixture was heated with reflux overnight, cooled to room temperature, diluted with water, and extracted three times with ethyl acetate. The combined organic layers were washed with water, dried over sodium sulfate, and concentrated under reduced pressure. The title compound was purified by chromatography on silica gel with dichloromethane containing 5% ethanol and recrystallized from ether.

yield: 0.59 g (33%) white powder, m.p. 85–88° C.

Step B: Prepatation of Ethyl 4-(3-(4-(aminoiminomethyl)phenyl)-1-oxa-2,8-diaza-spiro[4.5]dec-2-en-8-yl)butanoate hydrochloride 0.58 g (1.63 mmol) of the nitrile from Step A were dissolved in 35 ml dry ethanol and converted to the title amidine as described for Example 5, Step D. It was purified by chromatography on silica gel with dichloromethane/methanol 7:3.

yield: 0.4 g (60%) colorless foaml; ELISA: not tested PRP (ADP): $IC_{50}$=2.8 µM.

EXAMPLE 8

Preparation of 4-(3-(4-(Aminoiminomethyl)phenyl)-1-oxa-2,8-diaza-spiro[4.5]dec-2-en-8-yl)butanoic Acid

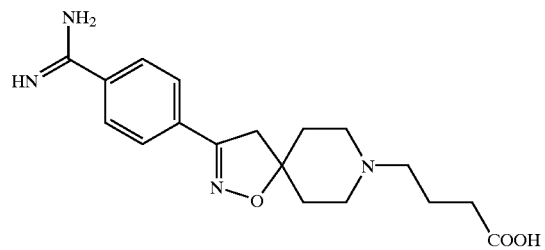

0.28 g (0.685 mmol) of the ethyl ester from Example 7 were hydrolized in a mixture of 4 ml ethanol and 0.9 ml 2 N queous sodium hydroxide solution according to the procedure rom Example 6. The title acid crystallized from water/thanol 1:2, and it was filtered and dried in vacuo.

yield: 0.09 g (38%), colorless crystals, m.p.>185° C. (dec.); ELISA: not tested PRP (ADP): $IC_{50}$=0.32 µM.

EXAMPLE 9

Ethyl 4-(3-(4-(Aminoiminomethyl)phenyl)-1-oxa-2,8-diaza-spiro[4.5]dec-2-en-8-yl)-4-oxobutanoate Hydrochloride

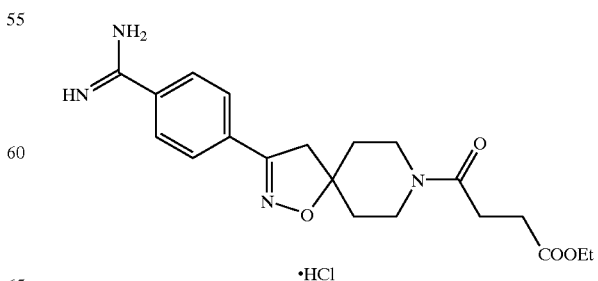

Step A: Preparation of 4-(3-(4-Cyanophenyl)-1-oxa-2,8-diaza-spiro[4.53]dec-2-en-8-yl)-4-oxobutanoic Acid

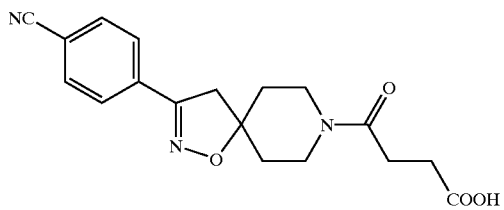

To a suspension of 1.2 g (5.0 mmol) of the intermediate from Example 5, Step B in 30 ml dry THF were added 0.5 g (5.0 mmol) succinic anhydride and 60 mg 4-N,N-dimethylaminopyridine (DMAP). After 30 min. heating with reflux another 0.15 g (1.5 mmol) succinic anhydride were added and refluxing was continued from 1.5 hours. The solvent was removed under reduced pressure, and the title compound was obtained by chromatography on silica gel with dichloromethane/ethanol 9:1. It was recrystallized from ether, filtered, and dried in vacuo.

yield: 0.98 g (58%) white powder, m.p. 167–170° C.

Step B: Prepatation of Ethyl 4-(3-(4-(Aminoiminomethyl)phenyl)-1-oxa-2,8-diaza-spiro[4.5]dec-2-en-8-yl)-4-oxobutanoate Hydrochloride A solution of 0.98 g (2.87 mmol) of the nitrile from Step A in 65 ml dry ethanol was converted to the amidine with by saturation with hydrogen chloride followed by addition of 65 ml saturated ethanolic ammonia solution as described for Example 5, Step D. It was purified by chromatography on silica gel with dichloromethane/ethanol 4:1.

yield: 0.48 g (40%), oil which solidified upon standing; ELISA: not tested PRP (ADP): not tested.

EXAMPLE 10

Preparation of 4-(3-(4-(Aminoiminomethyl)phenyl)-1-oxa-2,8-diaza-spiro[4.5]dec-2-en-8-yl)-4-oxobutanoic Acid

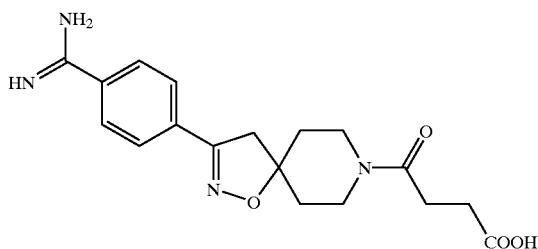

0.34 g (0.8 mmol) of the ethyl ester from Example 9 were hydrolized in a mixture of 5 ml ethanol and 1 ml 2 N aqueous sodium hydroxide solution according to the procedure from Example 6. A first crop (200 mg) of the title acid crystallized from water/ethanol 1:2. The mother liquid was concentrated, and a second crop (60 mg) was obtained by stirring with a mixture of ethyl acetate and ether. The crystals were filtered and dried in vacuo.

total yield: 0.26 g (90%) white powder, m.p.>255° C. (dec.); ELISA: not tested PRP (ADP): $IC_{50}=1$ $\mu$M.

EXAMPLE 11

Preparation of Ethyl 4-(9-(4-(Aminoiminomethyl)benzoyl)-3-oxo-1-oxa-4,9-diaza-spiro[5.5]undec-4-yl)butanoate Hydrochloride

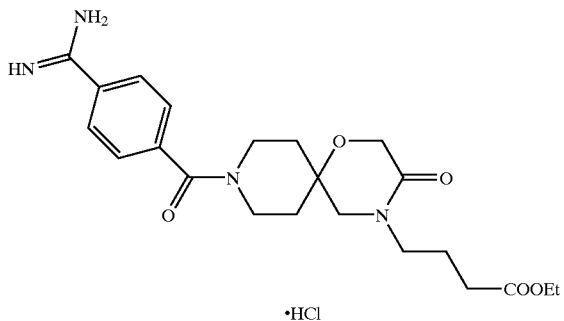

Step A: Preparation of 9-(4-Cyanobenzoyl)-3-oxo-1-oxa-4,9-diaza-spiro[5.5]undecane

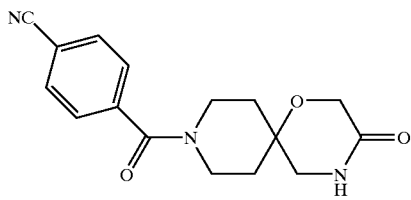

18.0 g (71.7 mmol) 3-oxo-1-oxa-4,9-diaza-spiro[5.5]undecane hydrobromide (prepared according to J. Med. Chem. 1983, 26, 855) were dissolved in 300 ml dry pyridine, and 11.9 g (71.9 mmol) 4-cyanobenzoyl chloride were added in small portions. The mixture was stirred over night at room temperature and evaporated under reduced pressure. The residue was dissolved in toluene, which was removed in vacuo. This process was repeated two times to remove remaining pyridine. It was treated with water and neutralized by addition of saturated aqueous sodium bicarbonate solution. The precipitate of the title compound was filtered with suction, washed with water, and dried in vacuo.

yield: 13.6 g (63%) white powder, m.p. 250–251° C.

Step B: Prepatation of Ethyl 4-(9-(4-Cyanobenzoyl)-3-oxo-1-oxa-4,9-diaza-spiro[5.5]undec-4-yl)butanoate

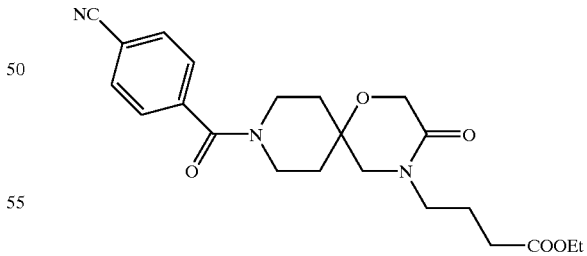

A mixture of 2.99 g (10.0 mmol) of the compound from the previous step and 100 ml dry DMF was warmed to 60° C. followed by addition of 0.44 g (11.0 mmol) sodium hydride (60% in mineral oil). It was kept with stirring for 30 min at this temperature until a clear solution was obtained. 2.14 g (10.97 mmol) ethyl 4-bromobutanoate were added dropwise after cooling to room temperature. The mixture was stirred over night, concentrated to dryness under reduced pressure, and treated with water and ethyl acetate.

1.7 g of remaining insoluble starting material was recovered by filtration. The organic layer was washed two times with brine, dried over sodium sulfate, and concentrated in vacuo. The title ester was obtained by chromatography on silica gel with ethyl acetate/ethanol 9:1.

yield: 0.8 g (19%) oil.

Ster C: Prepatation of Ethyl 4-(9-(4-(Aminoiminomethyl) benzoyl)-3-oxo-1-oxa-4,9-diaza-spiro[5.5]undec-4-yl) butanoate Hydrochloride A solution of 0.8 g (1.93 mmol) of the nitrile from the previous step in 50 ml dry ethanol was kept at 10° C. and saturated with gaseous hydrogen chloride. It was stirred over night at room temperature and concentrated to dryness under reduced pressure to leave the crude intermediate iminoester, which was treated with 50 ml 15% ethanolic ammonia and stirred again over night. The solvent was removed in vacuo, and the title amidine was obtained by chromatography on silica gel with ethanol/ethyl acetate 7:3.

yield: 0.11 g (12%) colorless foam; ELISA: not tested PRP (ADP): not tested.

EXAMPLE 12

Preparation of 4-(9-(4-(Aminoiminomethyl) benzoyl)-3-oxo-1-oxa-4,9-diaza-spiro[5.5]undec-4-yl)butanoic Acid Hydrochloride

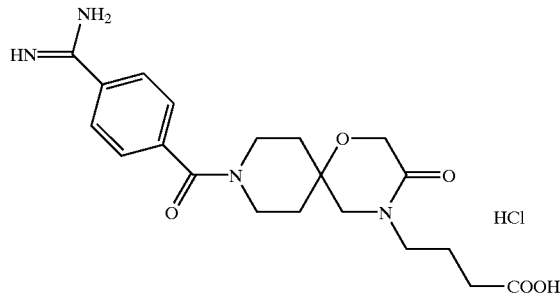

To a solution of 75 mg (0.16 mmol) of the ester from Example 11 in 10 ml ethanol was added 1 ml 2 N aqueous sodium hydroxide solution, and the mixture was stirred over night at room temperature. It was concentrated to dryness in vacuo, and the residue was dissolved in a small amount of water. It was acidified with 1 ml aqueous 2 N hydrochloric acid and the solvent was removed under reduced pressure. The residue was stirred several times with ethanol. The combined extracts were filtered through a plug of cotton wool and concentrated to dryness in vacuo to leave the pure title acid.

yield: 58 mg (82%) colorless foam; ELISA: not tested PRP (ADP): $IC_{50}$>10 µM.

EXAMPLE 13

Preparation of (8-(4-(Aminoiminomethyl)benzoyl)-1-phenylmethyl-2,4-dioxo-1,3,8-triaza-spiro[4.5] dec-3-yl)acetic Acid Trifluoroacetate

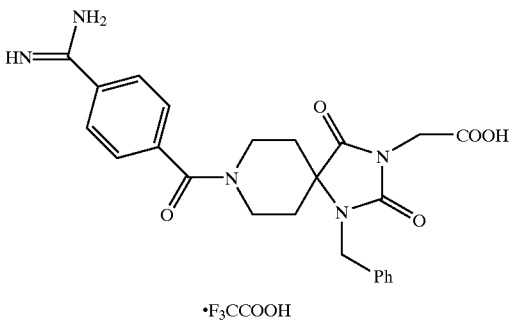

Step A: Pretaration of Benzyl 4-Benzylamino-4-cyanopiperidine-1-carboxylate Hydrochloride

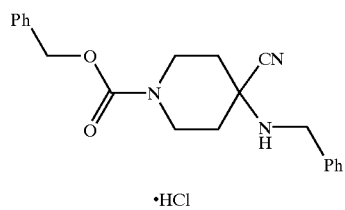

11.65 g (50 mmol) N-(benzyloxycarbonyl)piperidone (prepared from 4-piperidone and benzyl chloroformate according to Chem. Pharm. Bull. 1982, 30, 1084) and 7.2 g (50 mmol) benzylamine hydrochloride were dissolved in a mixture of 20 ml methanol and 10 ml water. The solution was kept at 0° C., while 15 ml of an aqueous solution of 3.26 g (50 mmol) potassium cyanide were added dropwise. After stirring overnight at room temperature a crystalline solid had been formed, which was collected by filtration. The filtrate was treated with a mixture of water and ether. The organic layer was separated and the aqueous layer extracted with ether. The combined organic layers were dried over sodium sulfate and added to the solid material. The title hydrochloride precipitated after treating with a saturated ethereal solution of hydrogen chloride, and it was isolated by filtration and dried in vacuo.

yield: 18.25 g (95%) white powder, m.p. 143–145° C. (dec.).

Step B: Pretaration of Benzyl 1-Benzyl-2,4-dioxo-1,3,8-triaza-spiro[4.5]decane-8-carboxylate

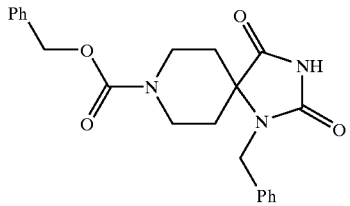

To a solution of 17.3 g (44.8 mmol) of the piperidine from the previous Step in 30 ml acetic acid were added 15 ml of an aqueous solution of 7.3 g (90.0 mmol) potassium cyanate. The mixture became a clear solution with slight warming. It was stirred for 30 min at room temperature followed by 45 min at 55° C. and poured into ice water. The aqueous solution was extracted two times with ethyl acetate, and the organic layer was concentrated in vacuo. The residue was treated with 45 ml 10% aqueous hydrochloric acid. It was kept at 55° C. for 15 min and diluted with water. After two extractions with ethyl acetate the combined extracts were washed with aqueous sodium bicarbonate solution, dried over sodium sulfate, and concentrated in vacuo. The remaining oil of the pure title hydantion slowly solidified upon standing.

yield: 13.25 g (75%) colorless amorphous solid; m.p. 123–125° C.

Step C: Preparation of 1-Phenylmethyl-2,4-dioxo-1,3,8-triaza-spiro[4.5]decane

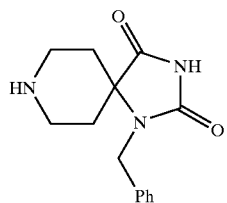

8.0 g (20.3 mmol) of the protected piperidine from Step C were dissolved in 100 ml ethanol. After addition of 500 mg 10 % Pd/C the mixture was filled into an autoclave and hydrogenated for 32 hours at 50 atm hydrogen and 50° C. The catalyst was removed by filtration, and the solution was concentrated under reduced pressure. The title compound was obtained from the residue by chromatography on silica gel with dichloromethane containing from 5% to 20% ethanol.

yield: 1.8 g (34%) pale yellow amorphous solid; m.p. 195–196° C.

Step D: Preparation of 8-(4-Cyanobenzoyl)-1-phenylmethyl-2,4-dioxo-1,3,8-triaza-spiro[4.5]decane

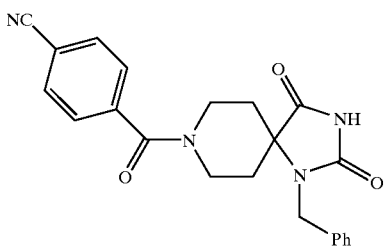

1.7 g (6.56 mmol) of the piperidine from the previous Step were dissolved in a mixture of 50 ml dry THF and 8 ml dry pyridine. After cooling with ice 1.1 g (6.64 mmol) 4-cyanobenzoyl chloride were added. It was stirred overnight at room temperature and poured into ice water. After two extractions with ethyl acetate the combined organic layers were successively washed two times with saturated aqueous Cu(II) sulfate solution and with brine. It was dried over sodium sulfate and concentrated under reduced pressure. The title compound was isolated from the residue by chromatography on silica gel with dichloromethane containing 4% ethanol.

yield: 0.92 g (36%) colorless crystals, m.p. 207–209° C.

Step E: Prepatation of tert.-Butyl (8-(4-Cyanobenzoyl)-1-phenylmethyl-2,4-dioxo-1,3,8-triaza-spiro[4.5]dec-3-yl)acetate

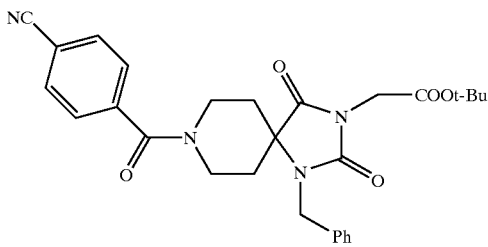

0.9 g (2.3 imol) of the compound from the previous Step were dissolved in 30 ml dry THF. After addition of 55 mg (2.3 mmol) sodium hydride it was stirred for 30 min at room temperature followed by addition of 0.585 g (3.0 mmol) tert.-butyl bromoacetate. The mixture was stirred for two days and poured into ice water. It was extracted two times with ethyl acetate. The combined organic layers were dried over sodium sulfate and concentrated in vacuo, and the title hydantion was obtained by chromatography on silica gel with dichloromethane/ethanol 96:4.

yield: 1.12 g (96%) oil.

Step F: Prepatation of tert.-Butyl (8-(4-((tert.-Butoxycarbonylamino)iminomethyl)benzoyl)-1-phenylmethyl-2,4-dioxo-1,3,8-triaza-spiro[4.5]dec-3-yl)acetate

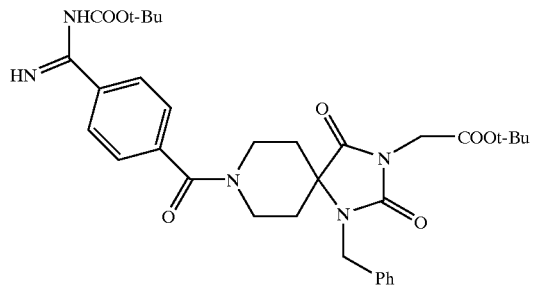

0.5 g (1.0 mmol) of the nitrile from Step E were dissolved in a mixture of 15 ml dry pyridine and 1.6 ml dry triethylamine. It was saturated with gaseous hydrogen sulfide, left at room temperature overnight, and poured into water. After three extractions with ethyl acetate the combined organic layers were dried over sodium sulfate and concentrated under reduced pressure. The residue was dissolved in 100 ml toluene, which was distilled off again in vacuo to remove traces of pyridine. To the remaining substance were added 5 ml acetone and 5 ml methyl iodide, and it was heated with reflux for 45 min, while a crystalline precipitate was formed. It was concentrated under reduced pressure, dissolved in 4 ml dry methanol, treated with 0.3 g (3.9 mmol) ammonium acetate and heated for 2 h at 60° C. The solvent was removed in vacuo, and the residue was stirred with ether. The solution was separated from the insoluble amidine, which was Boc-protected by dissolving in 10 ml of a 1:1 mixture of water and THF followed by addition of 0.9 g (6.5 mmol) potassium carbonate and 1.0 g (4.6 mmol) Boc2O and stirring for 1 hour at room temperature. It was diluted with water and extracted with ethyl acetate. The organic layer was dried over sodium sulfate and concentrated under reduced pressure, and the title compound was isolated by chromatography on silica gel with dichloromethane/ethanol 96:4.

yield: 0.24 g (39%) oil.

Step G: Preparation of (8-(4-(Aminoiminomethyl)benzoyl)-1-phenylmethyl-2,4-dioxo-1,3,8-triaza-spiro[4.5]dec-3-yl)acetic Acid Trifluoroacetate 220 mg (0.355 mmol) of the protected amidine from the previous Step were stirred at room temperature with 2 ml trifluoroacetic acid. After 2 hours the solvent was removed in vacuo, and the residue was dissolved in water. Again it was concentrated under reduced pressure. The title acid slowly precipitated by stirring with a mixture of ether and ethanol. It was collected by filtration and dried in vacuo.

yield: 0.05 g (24%) colorless powder, m.p.>197° C. (dec.); ELISA: not tested PRP (ADP): $IC_{50}$>100 μM.

EXAMPLE 14

Preparation of Ethyl 3-(3-(4-(Aminoiminomethyl)phenyl)-1-oxa-2,8-diaza-spiro[4.5]dec-2-en-8-yl)propanoate Hydrochloride

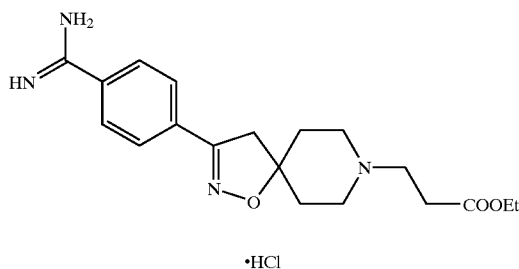

•HCl

Step A: Preparation of Methyl (3-(4-Cyanophenyl)-1-oxa-2,8-diaza-spiro[4.5]dec-2-en-8-yl)propanoate

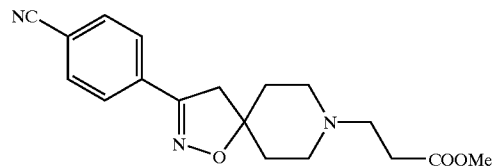

To a suspension of 2.0 g (8.3 mmol) of the intermediate from Example 5, Step B in 30 ml dry ethanol were added 0.715 g (8.3 mmol) methyl acrylate. The mixture was stirred over night at room temperature followed by 9 hours at 50° C. It was diluted with water and extracted five times with ethyl acetate. The combined organic layers were dried over sodium sulfate and concentrated under reduced pressure. One crop (0.64 g) of the title compound was obtained after chromatography on silica gel with ethyl acetate/ethanol 9:1 followed by recrystallization from ethanol. Another crop (0.23 g) was obtained by concentration of the aqueous layer to a small volume, filtration of the precipitate, stirring in hot ethanol, another filtration, and drying in vacuo.

total yield: 0.87 g (32%) colorless crystals, m.p.>225° C. (dec.).

Step B: Prepatation of Ethyl 3-(3-(4-(Aminoiminomethyl)phenyl)-1-oxa-2,8-diaza-spiro[4.5]dec-2-en-8-yl)propanoate Hydrochloride A solution of 0.39 g (1.19 mmol) of the nitrile from Step A in 30 ml dry ethanol was saturated with gaseous hydrogen chloride followed by treatment with 40 ml saturated ethanolic ammonia solution according to the procedure from Example 5, Step D. The title amidine was obtained by chromatography on silica gel with dichloromethane/methanol 3:1.

yield: 0.23 g (49%), pale yellow crystals, m.p.>192° C. (dec.); ELISA: not tested PRP (ADP): $IC_{50}$=0.64 μM.

EXAMPLE 15

Preparation of 4-(3-(4-(Aminoiminomethyl)phenyl)-1-oxa-2,8-diaza-spiro[4.5]dec-2-en-8-yl)propanoic Acid

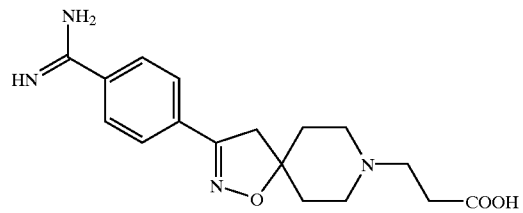

0.26 g (0.66 mmol) of the ester from Example 14 were hydrolized in a mixture of 4 ml ethanol and 0.9 ml 2 N aqueous sodium hydroxide solution as described in Example 6. The title acid crystallized from 1.5 ml ethanol/water 2:1.

yield: 0.1 g (46%) white powder, m.p.>243° C. (dec.); ELISA: not tested PRP (ADP): $IC_{50}$=0.11 μM.

EXAMPLE 16

Preparation of Ethyl 5-(3-(4-(Aminoiminomethyl)phenyl)-1-oxa-2,8-diaza-spiro[4.]dec-2-en-8-yl)-5-oxopentanoate Hydrochloride

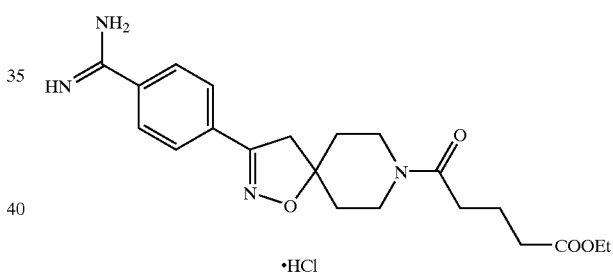

•HCl

Step A: Preparation of 5-(3-(4-Cyanophenyl)-1-oxa-2,8-diaza-spiro[4.5]dec-2-en-8-yl)-5-oxopentanoic Acid

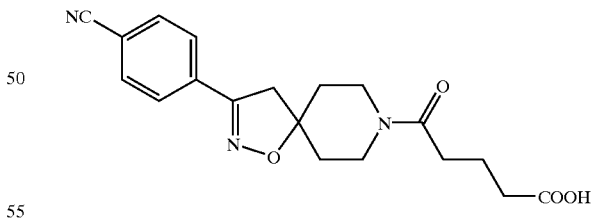

To a suspension of 1.5 g (6.22 mmol) of the intermediate from Example 5. Step B in 40 ml dry THF were added 0.71 g (6.22 mmol) glutaric anhydride and 76 mg 4-N,N-dimethylaminopyridine (DMAP). It was stirred for 1 h at room temperature followed by 2 h heating with reflux. The solvent was removed under reduced pressure, and the title compound was obtained by chromatography on silica gel with dichloromethane containing 4% ethanol. It was recrystallized from ethyl acetate/ether, and the crystals were collected by filteration and dried in vacuo.

yield: 0.97 g (44%) white powder, m.p. 183–185° C.

Step B: Prepatation of Ethyl 5-(3-(4-(Aminoiminomethyl)phenyl)-1-oxa-2,8-diaza-spiro[4.5]dec-2-en-8-yl)-5-oxopentanoate Hydrochloride A suspension of 0.91 g (2.56 mmol) of the nitrile from the previous Step in 60 ml dry ethanol was saturated with gaseous hydrogen chloride followed by treatment with 58 ml of a saturated ethanolic ammonia solution according to the procedure from Example 5. Step D. The mixture was concentrated under reduced pressure. A precipitate was removed by filtration after treatment with dichloromethane/ethanol 4:1, and the pure title amidine was obtained by chromatography on silica gel using the same solvent.

yield: 0.49 g (44%), pale yellow oil, which solidified upon standing; ELISA: not tested PRP (ADP): $IC_{50}$=0.2 µM.

EXAMPLE 17

Preparation of 5-(3-(4-(Aminoiminomethyl)phenyl)-1-oxa-2,8-diaza-spiro[4.5]dec-2-en-8-yl)-5-oxopentanoic Acid

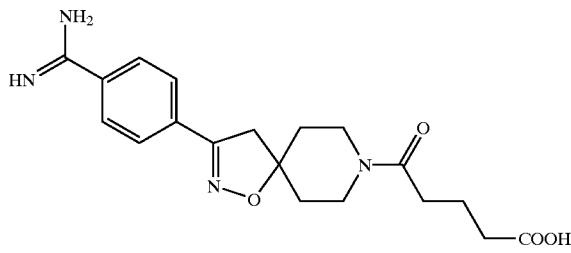

0.34 g (0.78 mmol) of the ethyl ester from Example 16 were dissolved in 5 ml ethanol, and after addition of 1 ml 2 N aqueous sodium hydroxide solution the mixture was stirred over night. It was brought to pH 5 with diluted acetic acid, stirred for 30 min, and the title acid was filtered with suction, washed with water and ethanol, successively, and dried in vacuo at 50° C.

yield: 0.28 g (97%), colorless crystals, m.p.>280° C. (dec.); ELISA: not tested PRP (ADP): $IC_{50}$=0.084 µM.

EXAMPLE 18

Preparation of Ethyl 5-(3-(4-(Aminoiminomethyl)phenyl)-1-oxa-2,8-diaza-spiro[4.5]dec-2-en-8-yl)pentanoate Hydrochloride

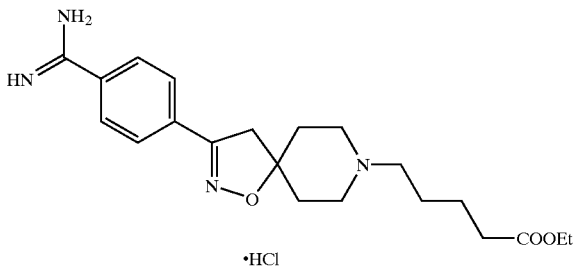

Step A: Prepatation of Ethyl 5-(3-(4-Cyanophenyl)-1-oxa-2,8-diaza-spiro[4.5]dec-2-en-8-yl)pentanoate

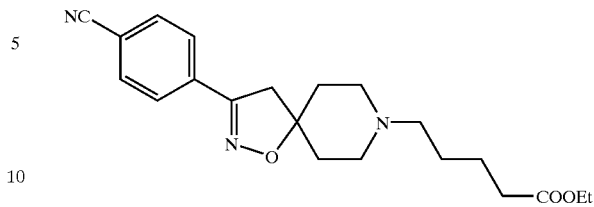

To a suspension of 1.1 g (4.56 mmol) of the intermediate from Example 5. Step B in 20 ml dry ethanol were added 1.26 g (9.12 mmol) potassium carbonate. After 15 min stirring at room temperature 1.03 g (4.93 mmol) ethyl 5-bromopentanoate and a catalytic amount of potassium iodide were added. It was stirred over night at room temperature, and the reaction was brought to completion by addition of another 0.52 g (2.49 mmol) ethyl 5-bromopentanoate and heating with reflux for 3 h. The mixture was poured into water and extracted three times with ethyl acetate. The combined organic layers were washed with water, dried over sodium sulfate, and concentrated under reduced pressure. The title compound was obtained by chromatography on silica gel with dichloromethane/ethanol 95:5 followed by 92:8.

yield: 0.57 g (34%), yellow oil, which solidified upon standing.

Step B: Prepatation of Ethyl 5-(3-(4-(Aminoiminomethyl)phenyl)-1-oxa-2,8-diaza-spiro[4.5]dec-2-en-8-yl)pentanoate Hydrochloride A solution of 0.55 g (1.49 mmol) of the nitrile from the previous step in 35 ml dry ethanol was saturated with gaseous hydrogen chloride and converted to the title amidine with 45 ml saturated ethanolic ammonia solution as described in Example 9. Step B. It was purified by chromatography on silica gel with dichloromethane/ethanol 4:1 followed by 3:1, and it solidified after addition of some drops of ethanolic ammonia.

yield: 0.51 g (81%), pale yellow amorphous solid, m.p. 146–148° C.; ELISA: not tested PRP (ADP): not tested.

EXAMPLE 19

Preparation of 5-(3-(4-(Aminoiminomethyl)phenyl)-1-oxa-2,8-diaza-spiro[4.5]dec-2-en-8-yl)pentanoic Acid

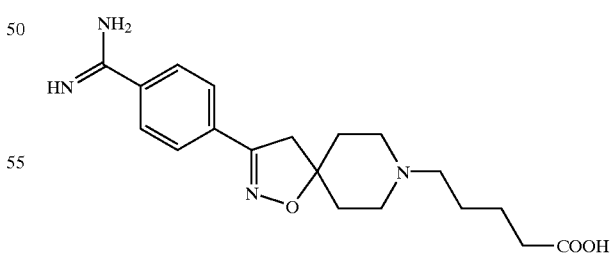

To a solution of 0.4 g (0.946 mmol) of the ester from Example 18 in 6 ml ethanol were added 1.2 ml 2 N aqueous sodium hydroxide solution. The mixture was stirred at room temperature over night, and stirring was continued for another 30 min after addition of another 0.2 ml sodium hydroxide. It was brought to pH 5 with diluted acetic acid, and the precipitate of the title compound was filtered with suction. After stirring with a small amount of water for 30 min, it was filtered again, washed with water and with ethanol, and dried in vacuo at 60° C.

yield: 0.125 g (37%) colorless amorphous solid, m.p. 236–238° C. (dec.); ELISA: not tested PRP (ADP): IC$_{50}$= 0.45 µM.

EXAMPLE 20

Preparation of (9-(2-(Pyridin-4-yl)ethyl)-3,9-diazaspiro[5.5]undec-3-yl)acetic Acid Bistrifluoroacetate

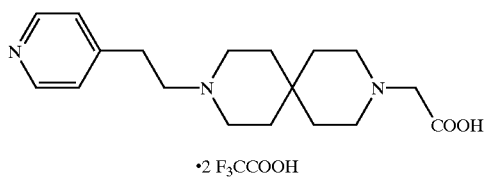

Step A: Preparation of 1,5-Dicyano-2,4-dioxo-9-phenylmethyl-3,9-diazaspiro[5.5]undecane

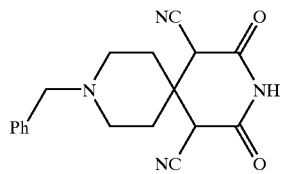

A mixture of 159.7 g (0.844 mol) N-benzylpiperidone and 191.0 g (1.689 mol) ethyl cyanoacetate was dissolved in a 12% ethanolic solution of ammonia, and it was kept in a refrigerator for 8 days, while the title compound precipitated from the solution. It was collected by filtration, washed with ethanol and ether, successively, and suspended in 910 ml water. It was brought to pH 6 with 2N hydrochloric acid, stirred for 1 h, filtered again, washed with water, and dried in vacuo.

yield: 177.2 g (65%) pale yellow crystals, m.p. 179–181° C.

Step B: Preparation of (4-(Hydroxycarbonylmethyl)-1-phenylmethyl piperidin-4-yl)acetic Acid Hydrochloride

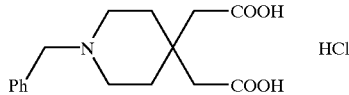

88.9 g (275.8 mmol) of the intermediate from the previous step were heated in 550 ml 18% hydrochloric acid for 24 h. After addition of 100 ml conc. HCl heating was continued for the same period. Solids were removed by filtration, and the title diacid precipitated upon concentration of the filtrate to 60% of its volume under reduced pressure. It was filtered with suction, washed with ethanol, and dried in vacuo.

yield: 46.0 g (51%) white powder, m.p. 223–225° C

Step C: Preparation of 9-Phenylmethyl-3,9-diazaspiro[5.5]undecan-2,4-dione

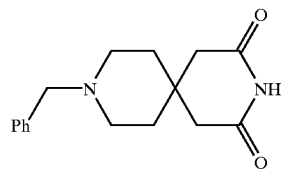

11.6 g (35.4 mmol) of the diacid from Stepn and 3.0 g (50.0 mmol) urea were thoroughly mixed in a mortar, and it was heated at 160° C. for 6 h. After 30 minutes no gas evolution could be observed. It was cooled to room temperature and stirred with ethanol. The solids were collected by filtration, suspended in saturated aqueous sodium bicarbonate solution, and stirred until gas evolution had ended. The title compound was filtered with suction, washed with water, and dried in vacuc.

yield: 6.05 g (63%) colorless needles, m.p. 209 210° C.

Step D: Preparation of 3-Phenylmethyl-3,9-diazaspiro[5.5]undecane

Under an atmosphere of argon was added in small portions to a suspension of 8.4 g (221.3 mmol) LiAlH$_4$ in 200 ml dry THF a suspension of 16.9 g (62.1 mmol) of the intermediate from the previous step in the same volume of THF, while the temperature was kept between 0° C. and 10° C. It was stirred for 1 h at room temperature and heated with reflux for another 4 h. The mixture was cooled and quenched with water. Solids were removed by filtration through a pad of silica gel, washed with ethanol, and the filtrate was concentrated under reduced pressure. The residue was stirred with ether, and it was filtered again. The pure title intermediate was obtained from the filtrate by evaporation of the solvent in vacuo.

yield: 11.7 g (77%) pale yellow amorphous solid, m.p. 105–106° C. (dec.).

Step E: Prepatation of tert.-Butyl (9-Phenylmethyl-3,9-diazaspiro[S.5]undec-3-yl)acetate

A mixture of 10.0 g (40.9 mmol) of the compound from the previous step, 8.55 g (43.83 mmol) tert.-butyl bromoacetate, and 6.2 g (44.9 mmol) dry potassium carbonate in 200 ml dry ethanol was heated with reflux for 3 h. After cooling to room temperature solids were removed by filtration and washed with ethanol. The filtrate was concentrated under reduced pressure, and the residue was stirred with tert.-butylmethylether. It was filtered again and washed with the same solvent. The filtrate was washed four times with water, dried over sodium sulfate, and concentrated in vacuo to leave the pure title compound.

yield: 9.37 g (64%) yellow oil.

Step F: Prepatation of tert.-Butyl (3,9-Diazaspiro[5.5]undec-3-yl)acetate

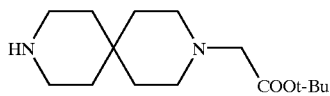

To a solution of 9.3 g (25.9 mmol) of the compound from step E in 400 ml dry ethanol were added 1.5 ml acetic acid and 0.7 g Pd(II) hydroxide. The mixture was filled into an autoclave and hydrogenated at 50 atm and 50° C. for 18 h. The solvent was removed under reduced pressure, and the residue was stirred with saturated aqueous sodium bicarbonate solution. It was extracted five times with 100 ml tert.-butylmethylether followed by three extractions with 100 ml dichloromethane. The extracts were dried over sodium sulfate and concentrated in vacuo, separately. The first extract contained a mixture of compounds, whereas the pure title intermediate was obtaind from the following.

yield: 5.52 g (79%) oil, which solidified upon standing.

Step G: Prepatation of tert.-Butyl (9-(2-(Pyridin-4-yl)ethyl)-3,9-diazaspiro[5.5]undec-3-yl)acetate

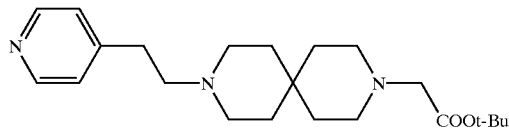

A solution of 2.5 g (9.3 nnol) of the compound from Step F and 0.98 g (9.3 mmol) 4-vinylpyridine in 20 ml dry acetonitrile was heated with reflux over night. The solvent was removed under reduced pressure, and the title compound was obtained from the residue by chromatography on aluminum oxide with dichloromethane followed by dichloromethane/ethanol 9:1.

yield: 2.49 g (72%) brown resin

Step H: Preparation of (9-(2-(Pyridin-4-yl)ethyl)-3,9-diazaspiro[5.5]undec-3-yl)acetic Acid Bistrifluoroacetate 0.1 g (0.268 mmol) of the ester from Step G in 2 ml trifluoroacetic acid were stirred at room temperature for 30 minutes. The solvent was removed under reduced pressure, and the remaining title compound was stirred with ether, collected by filtration, and dried in vacuo.

yield: 0.12 g (82%) beige hygroskopic crystalline solid; ELISA: not tested PRP (ADP): $IC_{50}$>100 $\mu$M.

EXAMPLE 21

Preparation of 4-(8-(4-(Aminoiminomethyl)benzoyl)-2,4-dioxo-1,3,8-triaza-spiro[4.5]dec-3-yl)butanoic Acid Trifluoroacetate

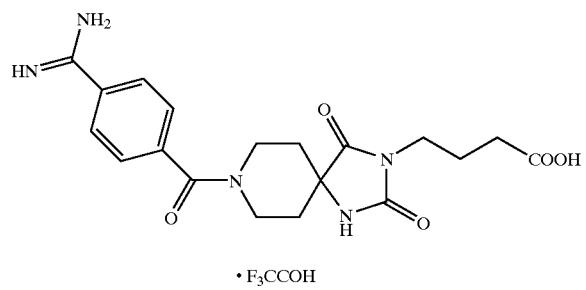

Step A: Preparation of 1,3,8-Triaza-spiro[4.5]decan-2,4-dione

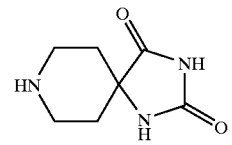

To a solution of 14.6 g (48.1 mmol) benzyl 2,4-dioxo-1,3,8-triaza-spiro[4.5]decan-8-carboxylate (prepared from N-(benzyloxycarbonyl)piperidone by the method from J. Med. Chem. 1995, a, 3772) in 250 ml dry ethanol were added 500 mg 10% Pd/C, and the mixture was filled into an autoclave. After stirring at 60° C. and 10 atm of hydrogen for 3 h no starting hydantoin could be detected by TLC. A precipitate had been formed which was redissolved by addition of 100 ml acetic acid. The catalyst was removed by filtration and the solution was concentrated in vacuo. Aqueous sodium bicarbonate solution was added until the mixture became a clear solution, and the title compound precipitated in two crops upon concentration in vacuo.

total yield: 8.1 g (99%), white powder, m.p. 303–304° C. (dec.).

Step B: Preparation of 8-(4-Cyanobenzoyl)-1,3,8-triaza-spiro[4.5]decan-2,4-dione

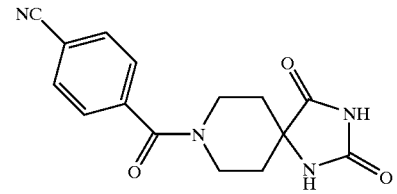

7.6 g (45.9 mmol) 4-cyanobenzoyl chloride were added to a cooled solution of 7.8 g (46.1 mmol) of the compound from the previous step in a mixture of 400 ml dry THF and 67 ml dry pyridine. After stirring over night at room temperature the mixture was poured into ice-cold water. It was extracted two times with ethyl acetate, and the combined organic layers were washed with diluted aqueous Cu(II) sulfate solution and with brine, successively. It was dried over sodium sulfate, and the title compound precipitated upon concentration under reduced pressure. It was collected by filtration and dried in vacuo.

yield: 4.9 g (36%), yellow crystalline solid, m.p. 144–146° C.

Step C: Prepatation of tert.-Butyl 4-(8-(4-Cyanobenzoyl)-2,4-dioxo-1,3,8-triaza-spiro[4.5]dec-3-yl)butanoate

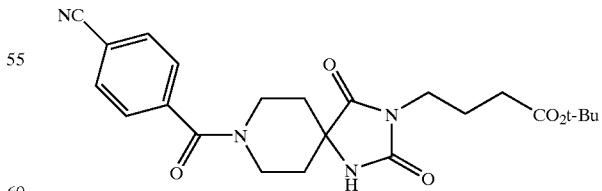

A mixture of 2.4 g (8.0 mmol) of the compound from Step B, 1.8 g (10.1 mmol) tert.-butyl 4-chlorobutanoate (prepared according to Chem. Ber. 1965, 98, 2312), 2.8 g (20.3 mmol) dry potassium carbonate, and a catalytic amount potassium iodide in 50 ml dry DMF was heated at 100° C. for 6 h until the conversion was complete. It was poured into ice-cold water, and the crude solid title compound was collected by filtration. It was redissolved in hot ethyl acetate and dried over sodium sulfate, which was removed by filtration. The title hydantoin crystallized from the filtrate by addition of hexane.

yield: 2.4 g (68%), colorless crystals, m.p. 225–226° C. (dec.).

Step D: Prepatation of tert.-Butyl 4-(8-(4-((tert.-Butoxycarbonylamino)iminomethyl)benzoyl)-2,4-dioxo-1,3,8-triaza-spiro[4.5]dec-3-yl)butanoate

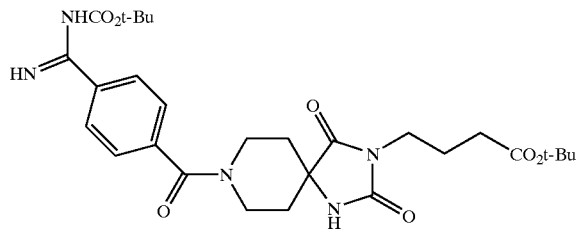

A solution of 0.9 g (2.0 nirol) of the comnpound from Step C in a mixture of 13 ml dry pyridine and 1.8 ml triethylamine was saturated with hydrogen sulfide during 2 h. After stirring over night at room temperature it was poured into water and extracted three times with ethyl acetate. The combined organic layers were dried over sodium sulfate and concentrated under reduced pressure followed by solution in 100 ml toluene. The solvent was evaporated in vacuo again, in order to remove remaining traces of pyridine. The residue was dissolved in 5 ml acetone, treated with 5 ml iodomethane, and heated with reflux for 75 minutes. It was concentrated to dryness, dissolved in 5 ml methanol, treated with 0.3 g (3.9 mmol) ammonium acetate, and heated for 2 h at 60° C. The solvent was removed in vacuo, and the solid residue was washed by stirring with ether, dissolved in 20 ml of a mixture of THF/water 1:1 followed by addition of 1.8 g (13.0 mmol) potassium carbonate and 2.0 g (9.2 mmol) Boc$_2$O. After stirring over night at room temperature it was diluted with water, extracted with ethyl acetate, and the organic layer was dried over sodium sulfate and concentrated under reduced pressure. The title compound was obtained from the residue by chromatography on silica gel with dichloromethane/ethanol 9:1.

yield: 0.41 g (36%), white powder, m.p. 133–135° C. (dec.).

Step E: Preparation of 4-(8-(4-(Aminoiminomethyl) benzoyl)-2,4-dioxo-1,3,8-triaza-spiro[4.5]dec-3-yl)butanoic Acid Trifluoroacetate 0.19 g (0.34 mmol) of the protected amidine from the previous step were stirred in 1 ml trifluoroacetic acid at room temperature for 45 minutes. The mixture was concentrated to dryness under reduced pressure, and the residue of the title compound crystallized by stirring in a mixture of ether and ethanol. It was filtered with suction and dried in vacuo.

yield: 0.14 g (80%), white powder, m.p. 226° C. (dec.); ELISA: not tested PRP (ADP): IC$_{50}$>10 µM.

EXAMPLE 22

Ethyl (3-(2-(Pyridin-4-yl)ethyl)-3-azaspiro[5.5] undec-9-yl)acetate

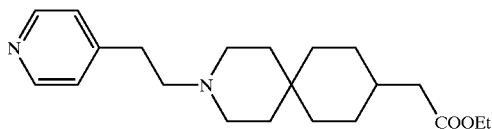

A solution of 0.48 g (2.0 mmol) of the intermediate from Example 1, Step C and 0.21 g (2.0 mmol) 4-vinylpyridine in 6 ml acetonitrile were heated at 80° C. over night. The solvent was removed under reduced pressure, and the remaining solid title compound was purified by stirring several times with tert.-butylmethylether, filtered with suction, and dried in vacuo.

yield: 0.17 g (25%), brown crystalline solid, m.p. 142° C.; ELISA: not tested PRP (ADP): IC$_{50}$>100 µM.

EXAMPLE 23

(3-(2-(Pyridin-4-yl)ethyl)-3-azaspiro[5.5]undec-9-yl) acetic Acid

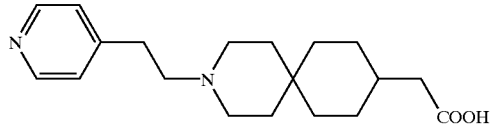

To a solution of 0.05 g (0.145 mmol) of the ester from Example 22 in 2 ml ethanol were added three drops of 2N aqueous sodium hydroxide solution. The mixture was heated at 70° C. for 3 h and diluted with 10 ml water. It was washed two times with dichloromethane, and the aqueous layer was adjusted to pH 7–8 with hydrochloric acid. After another extraction with dichloromethane the aqueous layer was concentrated under reduced pressure and the residue stirred with 20 ml of a mixture of ethanol/dichloromethane 9:1. Solids were removed by filtration, and the filtrate was concentrated in vacuo to leave the pure title acid.

yield: 0.2 g (44%), pale yellow resin; ELISA: not tested PRP (ADP): IC$_{50}$>100 µM.

Example 24

Ethyl (3-(2-(Piperidin-4-yl)ethyl)-3-azaspiro[5.5] undec-9-yl)acetate

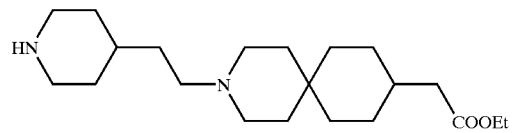

0.17 g (0.5 mmol) of the compound from Example 22 were dissolved in 25 ml 90% acetic acid followed by addition of 30 mg platinum(IV) oxide. The mixture was filled into an autoclave and hydrogenated for 4 h at room temperature and a pressure of 20 atm. The catalyst was removed by filtration and the solvent evaporated under reduced pressure. The residue was treated with water and neutralized with sodium carbonate followed by extraction with dichloromethane. The organic layer was dried over sodium sulfate and concentrated in vacuo to leave the pure title compound.

yield: 0.04 g (23%), brown resin; ELISA: not tested PRP (ADP): $IC_{50}$>100 μM.

EXAMPLE 25

(3-(2-(Piperidin-4-yl)ethyl)-3-azaspiro[5.5]undec-9-yl)acetic Acid

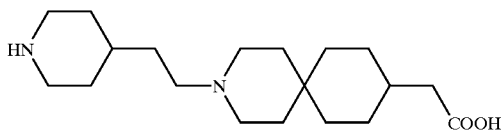

0.35 g (1.0 mmol) of the compound from Examrle 24 were hydrolized in 15 ml ethanol containing 7 drops aqueous sodium hydroxide as described for Example 23. The title acid solidified upon stirring in dichloromethane. It was filtered and dried in vacuo.

yield 0.03 g (9%), beige crystalline solid, m.p. 263–265 ° C.; ELISA: not tested PRP (ADP): $IC_{50}$>10 μM.

EXAMPLE 26

(9-(2-(Pyridin-4-yl)ethyl)-2,4-dioxo-3,9-diazaspiro [5.5]undec-3-yl)acetic Acid Trifluoroacetate

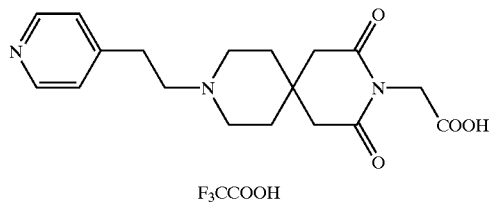

Step A: Prepatation of tert.-Butyl (9-Phenylmethyl-2,4-dioxo-3,9-diazaspiro[5.5]undec-3-yl)acetate

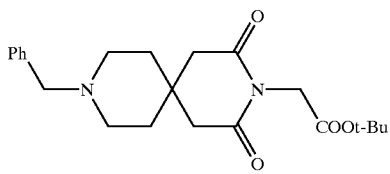

To a suspension of 10.0 g (36.7 mmol) of the imid from Example 20, Step C in 100 ml dry DMF were added in small portions 0.9 g (37.5 mmol) sodium hydride, which had been purified from mineral oil by washing with hexane, and the mixture was stirred for 30 minutes at 50° C. After addition of 7.0 g (35.9 mmol) tert.-butyl bromoacetate it was stirred at room temperature over night, poured into 300 ml water, and extracted two times with tert.-butylmethylether. The combined organic layers were dried over sodium sulfate, concentrated in vacuo, and the title ester was obtained by chromatography on silica gel with dichloromethane followed by dichloromethane/ethanol 96:4.

yield: 13.5 g (97%) oil, which solidified upon standing.

Step A: Prepatation of tert.-Butyl (2,4-Dioxo-3,9-diazaspiro [5.5]undec-3-yl)acetate

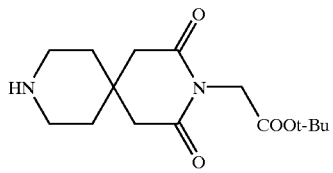

To a solution of 13.4 g (34.7 mmol) of the compound from Step a in 500 ml ethanol were added 2 ml acetic acid and 0.9 g Pd(II) hydroxide. The mixture was filled into an autoclave and hydrogenated at 50° C. and 50 atm for 20 h. The solvent was removed in vacuo, and the residue was stirred with saturated aqueous sodium bicarbonate solution. It was extracted several times with tert.-butylmethylether, and the combined extracts were dried over sodium sulfate and concentrated under reduced pressure. The title compound was obtained by chromatography on silica gel with dichloromethane followed by dichloromethane/ethanol 7:3.

yield: 6.8 g (66%) oil, which solidified upon standing.

Step C: Prepatation of tert.-Butyl (9-(2-(Pyridin-4-yl)ethyl)-2,4-dioxo-3,9-diazaspiro[5.5]undec-3-yl)acetate

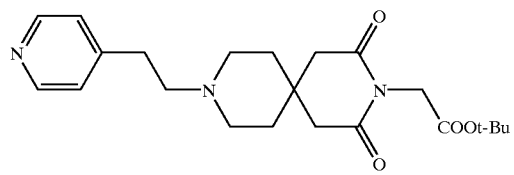

A solution of 3.0 g (10.1=mol) of the compound from the previous step and 1.05 g (10.0 mol) 4-vinylpyridine in 20 ml dry acetonitrile were heated with reflux for 6 h and stirred over night at room temperature. The solvent was removed under reduced pressure, and the title pyridine was obtained by chromatography on silica gel with dichloromethane followed by dichloromethane/ethanol 9:1.

yield: 2.25 g (56%) beige resinous crystals.

Step D: Preparation of (9-(2-(Pyridin-4-yl)ethyl)-2,4-dioxo-3,9-diazaspiro[5.5]undec-3-yl)acetic Acid Trifluoroacetate 0.1 g (0.25 mmol) of the ester from Step C were stirred in 2 ml trifluoroacetic acid at room temperature for 30 minutes. The solvent was removed in vacuo, and the remaining title compound was purified by treating with ethanol and dichloromethane, successively, which was removed under reduced pressure.

yield: 0.11 g (96%), beige resinous crystals; ELISA: not tested PRP (ADP): $IC_{50}$>100 μM.

EXAMPLE 27

(9-(2-(Piperidin-4-yl)ethyl)-3,9-diazaspiro[5.5] undec-3-yl)acetic Acid Tristrifluoroacetate

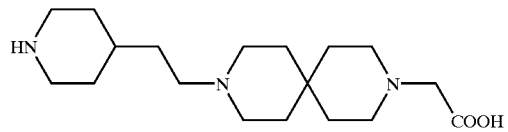

Step A: Prepatation of tert.-Butyl (9-(2-(Piperidin-4-yl)ethyl)-3,9-diazaspiro[5.51]undec-3-yl)acetate

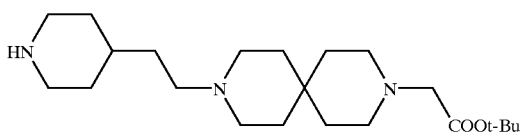

0.83 g (2.22 imol) of the pyridine from Example 20 Step G were dissolved in 50 ml dry ethanol followed by addition of 0.13 ml acetic acid and 0.1 g platinum(IV) oxide. The mixture was filled into an autoclave and hydrogenated at 50° C. and 100 atm. After three days the same amounts of acetic acid and of the catalyst were added, but even after eight days the conversion was not complete. The solvent was removed under reduced pressure, and the residue was stirred with 5% aqueous sodium carbonate solution. It was extracted with tert.-butylmethylether, and the organic layer was dried over sodium sulfate and concentrated in vacuc. The acetate of the title compound, which was neutralized by washing a dichloromethane solution with 2N aqueous sodium hydroxide, was obtained by chromatography on aluminum oxide with dichloromethane followed by dichloromethane/ethanol 7:3.

yield: 0.42 g (50%) beige resin.

Step B: Preparation of (9-(2-(Piperidin-4-yl)ethyl)-3,9-diazaspiro[5.5]undec-3-yl)acetic Acid Tristrifluoroacetate 0.1 g (0.263 mmol) of the ester from qten A were cleaved with trifluoroacetic acid as described for Example 26. Step D.

yield: 0.14 g (80%) beige amorphous solid; ELISA: not tested PRP (ADP): $IC_{50}$=100 μM.

EXAMPLE 28

(9-(2-(Piperidin-4-yl)ethyl)-2,4-dioxo-3,9-diazaspiro[5.5]undec-3-yl)acetic Acid Diacetate

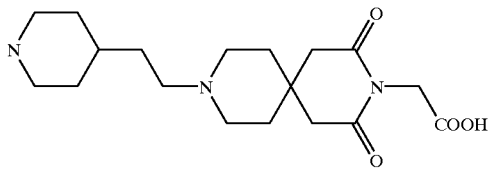

2 H₃CCOOH

To a solution of 0.5 g (1.25 mmol) of the compound from Example 26, Step C in 40 ml 90% acetic acid were added 100 mg $PtO_2$. The mixture was filled into an autoclave and hydrogenated at 20 atm and room temperature for 22 h. The solvent was removed under reduced pressure, and the residue was stirred with ether. The insoluble title compound was separated and dried in vacuo.

yield: 0.56 g (95%) pale yellow resin; ELISA: not tested PRP (ADP): not tested.

EXAMPLE 29

(S)-5-(9-(3-((Aminoiminomethyl)amino)-1-oxopropyl)-3,9-diazaspiro[5.5]undecan-3-yl)-2-benzenesulfonylamino-5-oxopentanoic Acid Hydrochloride

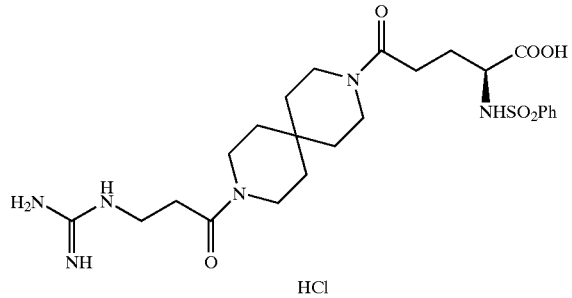

HCl

Step A: Preparation of (S)-2-Aminopentanedioic Acid 1-tert.-Butyl Ester

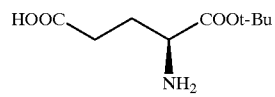

To a solution of 25.0 g (74.1 mmol) (S)-2-(benzyloxycarbonylamino)pentanedioic acid 1-tert.-butyl ester (prepared according to Liebigs Ann. Chem. 1961, 646, 127) in 500 ml dry methanol were added 2.5 g 10% Pd/C, and the mixture was stirred over night at room temperature under an atmosphere of hydrogen. The catalyst was removed by filtration through celite and the filtrate was concentrated under reduced pressure. The remaining solid title compound was purified by stirring with a small amount of ethanol, filtered with suction, and dried in vacuo. Another crop (1.7 g) was obtained after concentration of the mother liquid and stirring of the residue with ethyl acetate.

total yield: 11.55 g (77%), white powder, m.p. 114–116° C.

Step B: Preparation of (S)-2-(Benzenesulfonylamino)pentanedioic Acid 1-tert.-Bbutyl Ester

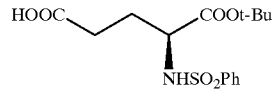

11.5 g (56.6 mmol) of the amino acid from the previous step were dissolved in a mixture of 710 ml water and 57 ml 1N aqueous sodium hydroxide solution, and the solution was cooled to 0° C. 6.6 g (62.3 mmol) sodium carbonate were added followed by dropwise addition of 11.0 g (62.3 mmol) benzenesulfonyl chloride. After 1 h at 0° C. stirring was continued over night at room temperature, while the pH of the mixture dropped from pH 10 to pH 7. It was extracted two times with ethyl acetate, and the aqueous layer was adjusted to pH 2 with 2N hydrochloric acid. The solution was extracted four times with ethyl acetate, and the combined organic layers were washed with brine and with water, successively, dried over sodium sulfate, and concentrated under reduced pressure to leave the pure title sulfonamide.

yield: 13.0 g (67%) pale yellow sirup, which solidified immediately upon standing.

Step C: Preparation of (S)-tert.-Butyl 2-Benzenesulfonylamino-5-oxo-5-(9-phenylmethyl-3,9-diazaspiro[5.5]undecan-3-yl)pentanoate

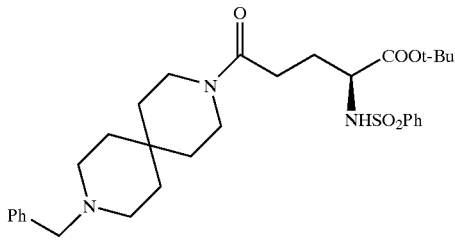

A solution of 6.82 g (19.86=mol) of the intermediate from Step B in 20 ml dry THF containing 2.8 ml triethylamine was cooled to −10° C. 2.15 g (19.8 mmol) ethyl chloroformate were added dropwise, and the mixture was stirred for ten minutes, while a precipitate was formed spontaneously. A solution of 4.85 g (19.86 mmol) of the intermediate from Example 20. Step D in a mixture of 24 ml dry ThF and 5.3 ml triethylamine was added quickly in small portions. It was warmed to room temperature, stirred over night, poured into water, and extracted three times with ethyl acetate. The combined organic layers were washed with water, dried over sodium sulfate, and concentrated under reduced pressure, and the title compound was obtained by chromatography on silica gel with dichloromethane/ethanol 93:7.

yield: 3.9 g (34%) colorless crystalline solid, m.p. 134–136° C.

Step D: Preparation of (S)-tert.-Butyl 2-Benzenesulfonylamino-5-(3,9-diazaspiro[5.5]undecan-3-yl)-5-oxopentanoate Acetate

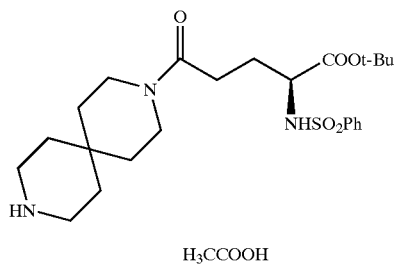

To 200 mg 10% Pd/C were added 30 ml dry methanol and 6 drops acetic acid. A stream of hydrogen was passed through the mixture for 20 minutes, and 2.0 g (3.5 mmol) of the intermediate from the previous step were added. It was stirred at room temperature for four days followed by addition of another 100 mg of the catalyst and 6 drops acetic acid, and stirring was continued for an additional day. The catalyst was removed by filtration through celite, and the filtrate was concentrated under reduced pressure to leave the title compound, which was purified by crystallization from ethyl acetate.

yield: 1.15 g (61%) white powder, m.p. 153–156° C.

Step E: Preparation of (S)-tert.-Butyl 2-Benzenesulfonylamino-5-(9-(3-benzyloxycarbonylamino-1-oxopropyl)-3,9-diazaspiro[5.5]undecan-3-yl)-5-oxopentanoate

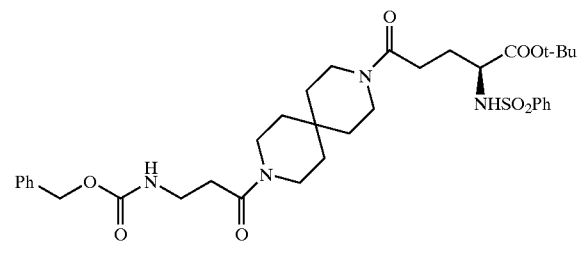

The reaction was carried out as described in Step C. A solution of 0.51 g (2.3 mmol) 3-(benzyloxycarbonylamino) propionic acid in 3 ml THF and 0.65 ml triethylamine was treated with 0.25 g (2.3 mmol) ethyl chloroformate followed by a solution of 1.1 g (2.04 mmol) of the compound from the previous step in a mixture of 4 ml THF, 0.6 ml triethylamine, and 1 ml water. It was stirred for two days at room temperature, and the pure title intermediate was obtained after chromatography on silica gel with dichloromethane containing 4% ethanol.

yield: 0.86 g (62%) colorless crystals, m.p. 50–54° C.

Step F: Preparation of (S)-tert.-Butyl 5-(9-(3-Amino-1-oxopropyl)-3,9-diazaspiro[5.5]undecan-3-yl)-2-benzenesulfonylamino-5-oxopentanoate

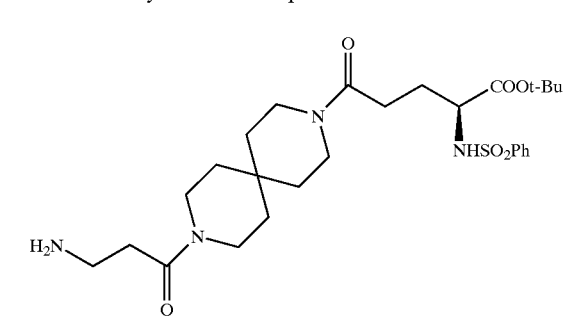

To a solution of 0.74 g (1.08 mmol) of the compound from Step E in 10 ml ethanol were added 70 mg 10% Pd/C. It was stirred over night at room temperature, while a slight stream of hydrogen passed through the mixture. The catalyst was removed by filtration through celite, and the filtrate was concentrated in vacuo to leave the pure title amine.

yield: 0.56 g (94%) pale yellow foam.

Step G: Preparation of (S)-tert.-Butyl 2-Benzenesulfonylamino-5-(9-(3-(((tert.-butoxycarbonylamino)(tert.-butoxycarbonylimino)methyl)amino)-1-oxopropyl)-3,9-diazaspiro[5.5]undecan-3-yl)-5-oxopentanoate

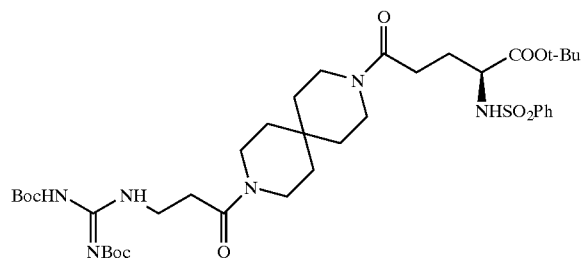

To a suspension of 0.44 g (2.03 mmol) mercury(II) oxide in 25 ml dry dioxane were added successively 0.56 g (1.02 mmol) of the amine from the previous step and 0.28 g (1.05 nmmol) N,N'-bis(tert.-butoxycarbonyl)thiourea (prepared according to Tetrahedron Lett. 1992, 33, 5933), each dissolved in a small amount of dioxane. After two days stirring at room temperature another 50 mg mercury(II) oxide were added and stirring was continued for the same time. It was filtered through a pad of celite, and the filtrate was concentrated under reduced pressure. The title compound was obtained from the residue by chromatography on silica gel with dichloromethane containing 4% ethanol.

yield: 0.52 g (64%) pale yellow film, which solidified upon standing.

Step H: Preparation of (S)-5-(9-(3-((Aminoiminomethyl) amino)-1-oxopropyl)-3,9-diazaspiro[5.5]undecan-3-yl)-2-benzenesulfonylamino-5-oxopentanoic Acid Hydrochloride A stream of gaseous hydrogen chloride was passed for 40 minutes through a solution of 0.3 g (0.38 mmol) of the protected guanidine from the previous step in 15 ml dry dichloromethane at 0° C., while a precipitate was formed. It was stirred for additional 2 h at room temperature, and the solvent was removed under reduced pressure. The solid residue of the title compound was stirrred with ether, filtered with suction, washed with ether, and dried in vacuo at 50° C.

yield: 206 mg (95%) colorless crystalline solid, m.p.>127° C. (dec.). ELISA: not tested PRP (ADP): $IC_{50}$=.

EXAMPLE 30

Preparation of (8-(4-(Aminoiminomethyl)benzoyl)-2-oxo-1-oxa-3,8-diaza-spiro[4.5]dec-3-yl)acetic Acid

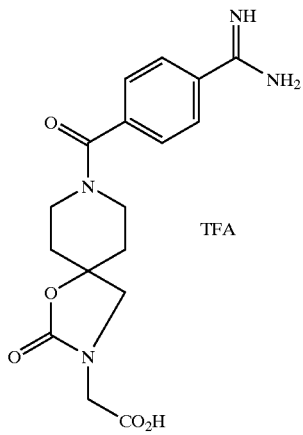

Step A: Preparation of t-Butyl 8-Benzyl-(2-oxo-1-oxa-3,8-diaza-spiro[4.5]dec-3-yl)acetate.

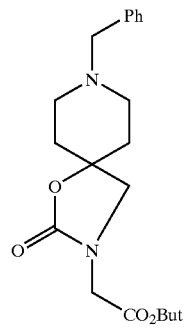

A solution of 8-benzyl-2-oxo-1-oxa-3,8-diazo-spiro[4.5]decane (0.83 g, 3.89 mmol), prepared as described in J. Med. Chem, 24, 1320–1328(1981), and tetrahydrofuran (5 mL) was treated with sodium hydride (0.102 g of a 60% dispersion in oil, 4.28 mmol). The resulting mixture was heated to reflux. After one hour, the mixture was allowed to cool to room temperature. This solution was treated with t-butyl bromoacetate (0.7 mL, 4.28 mmol) by dropwise addition. After one hour, the resulting mixture was diluted with ethyl acetate (50 mL) and washed with water.

The organic phase was concentrated in vacuo. The residue was chromatographed on silica gel, eluting with hexanes/ethyl acetate (1:1), to give the title compound as a solid.

Yield=1.12 g (83%), m.p. 157–159° C., FDMS m/z=360.

Step B: Preparation of t-Butyl (2-oxo-1-oxa-3,8-Diaza-spiro[4.5]dec-3-yl)acetate.

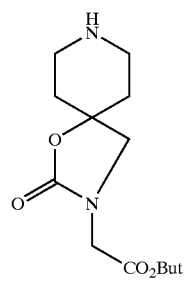

A mixture of the compound prepared in Example 30A (0.60 g, 1.66 mmol), 10% palladium in carbon (0.5 g), ethylacetate (200 mL), and ethanol (20 mL) was stirred under a $H_2$ atmosphere. After four hours, the reaction mixture was filtered, and the filtrate was concentrated in vacuo.

Yield=0.41 g, m.p. 76–85° C., FDMS m/z=270.

Step C: Preparation of t-Butyl (8-(4-Cyanobenzoyl)-2-oxo-1-oxa-3,8-diaza-spiro[4.5]dec-3-yl)acetate.

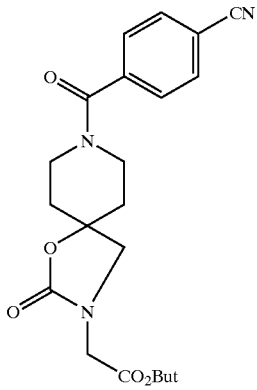

A solution of the compound prepared in Example 30B (0.15 g, 0.556 mmol), methylene chloride (2.0 mL), and pyridine (2.0 mL) was treated with 4-cyanobenzoyl chloride (0.103 g, 0.611 mmol). After two hours at room temperature, the mixture was diluted with ethyl acetate (50 mL). The resulting mixture was washed with water, and concentrated in vacuo. The residue was chromatographed on silica gel, eluting with ethyl acetate.
Yield=0.18 g FDMS m/z=400.3.

Step D: Preparation of t-Butyl (8-(4-(N-t-Butoxycarbonyl-aminoiminomethyl)benzoyl)-2-oxo-1-oxa-3,8-diaza-spiro[4.5]dec-3-yl)acetate.

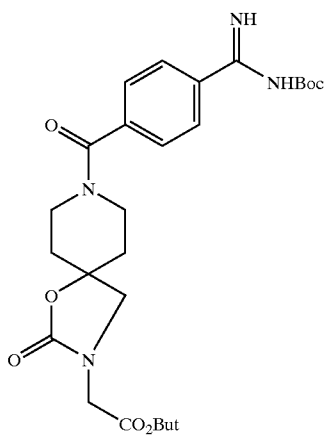

A mixture of the compound prepared in Example 30C (0.179 g, 0.45 mmol), pyridine (10 mL), and triethylamine (1 mL) was saturated with $H_2S$, then allowed to stand at room temperature. After 18 hours, this mixture was concentrated to dryness. The residue was suspended in a mixture of acteone (5.0 mL) and methyl iodide (5.0 mL). The resulting mixture was heated at reflux for 1 hour. The reaction solution was then allowed to cool to room temperature and concentrated to dryness. The residue was disolved in methanol (5 mL), and treated with ammonium acetate (0.10 g, 1.35 mmol). The resulting solution was heated at 60° C. for 2 hours. This material was concentrated to dryness. The residue was suspended in a mixture of tetrahydrofuran and water (10 mL, 1:1) and treated with potassium carbonate (0.37 g, 2.7 mmol) and di-tert-butyl dicarbonate (0.49 g, 2.2 mmol). The resulting mixture was stirred at room temperature for 2 hours, then diluted with ethyl acetate (100 mL). The resulting mixture was washed with water, then the organic phase was concentrated. The residue was purified by chromatography, eluting with tetrahydrofuran/chloroform (1:8) giving the title compound.
Yield=0.175 g FDMS m/z=517.

Step E: Preparation of (8-(4-(Aminoiminomethyl)benzoyl)-2-oxo-2-oxa-3,8-diaza-spiro[4.5]dec-3-yl)acetic Acid.

A mixture of the compound prepared as described in Example 30D (0.175 g, 0.33 mmol) and trifluoroacetic acid (10 mL) was maintained at room temperature for 1 hour, then concentrated to dryness. The residue was triturated with diethyl ether, and the solid collected by filtration.
Yield=0.17 g FAB MS m/z=361. ELISA: $IC_{50}$=29 μM PRP (ADP): $IC_{50}$=80 μM.

EXAMPLE 31

Preparation of (8-(2-(4-Aminoiminomethyl)acetyl)-2-oxo-1-oxa-3,8-diaza-spiro[4.5]dec-3-yl)acetic Acid.

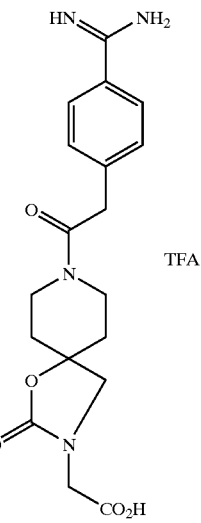

Step A: Preparation of t-Butyl (8-(2-(4-Cyanophenyl)-acetyl)-2-oxo-1-oxa-3,8-diaza-spiro[4.5]dec-3-yl)acetate.

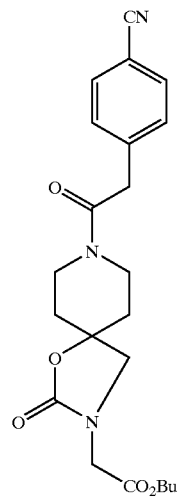

A mixture of the compound prepared as described in Example 30B (0.08 g, 0.29 mmol), 4-cyanophenylacetic acid (0.051 g, 0.322 mmol) and methylene chloride (2.0 mL) was treated with 1-(3-dimethylaminopropyl)-3-ethylcarbodiimide (0.087 g, 0.44 mmol), and dimethylaminopyridine (catalitic amount). Resulting mixture was stirred at room temperature for about 2 hours. The reaction mixture was diluted with ethyl acetate and washed with water. The organic phase was concentrated and the residue purified by chromatography, eluting with ethyl acetate.

Yeild=0.11 g (85%) FABMS m/z=414.

Step B: Preparation of t-Butyl (8-(2-(4-N-t-Butoxycarbonyl aminoiminomethyl)acetyl)-2-oxo-1-oxa-3,8-diaza-spiro [4.5]dec-3-yl)acetate.

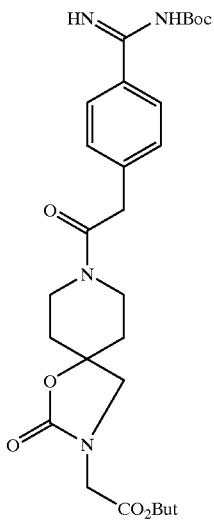

The compound was prepared using the procedure substantially as described in Example 30D.

FDMS m/z=414.

Step C: Preparation of (8-(2-(4-Aminoiminomethyl)acetyl)-2-oxo-1-oxa-3,8-diaza-spiro[4.5]dec-3-yl)acetic Acid.

Compound was deprotected was trifluoroacetic acid following the procedure substantially as described in Example 30E.

FABMS m/z=488. ELISA: IC$_{50}$=0.074 μM PRP (ADP): IC$_{50}$=1.11 μM.

EXAMPLE 32

Preparation of ((9-(2-(4-(Aminoiminomethyl)phenyl) acetyl)-2-oxo-1-oxa-3,9-diaza-spiro[5.5]dec-3-yl)acetic Acid

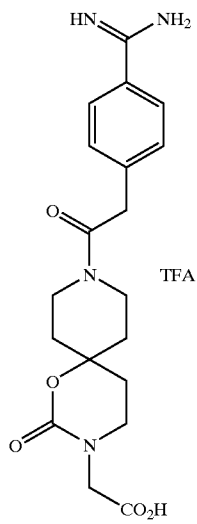

Step A: Preparation of t-Butyl (9-Benzyl-2-oxo-1-oxa-3,9-diaza-spiro[5.5]undec-3-yl)acetate.

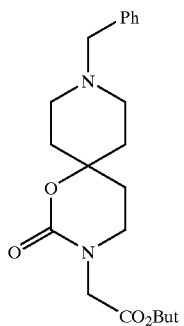

The title compound was prepared from spirocarbonate prepared as described in Eur. J. Med. Chem. Ther., 9, 416–423 (1974), using the procedure substantially as described in Example 30A.

m.m. 113–144° C. FDMS m/z=374.

Step B: Preparation of t-Butyl (2-oxo-1-oxa-3,9-diaza-spiro [5.5]undec-3-yl)acetate.

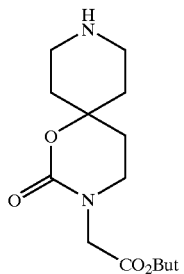

A mixture of the compound prepared as described in Step A (0.53 g), 10% palladium on carbon (0.5 g) and ethenol (10 mL) were maintained under hydrogen for 2 hours. The reaction mixture was filtered, and the filtrated concentrate in vacuo. Recrystallization of the residue from hexane provided the title compound m.p. 110–115° C. FDMS m/z–284.

Step C: Preparation of C-Butyl ((9-(2-(4-cyanophenyl)-acetyl)-2-oxo-1-oxa-3,9-diaza-spiro[5.5]undec-3-yl)acetate.

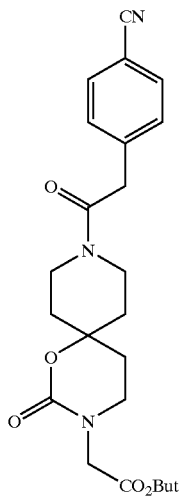

The title compound was prepared using the procedure substantially as described in Example 31A.

FDMS m/z=427.

Step D: Preparation of t-Butyl ((9-(2-(4-(N-t-Butoxycarbonylaminoiminomethyl)phenyl)acetyl)-2-oxo-1-oxa-3,9-diaza-spiro[5.5]undec-3-yl)acetate.

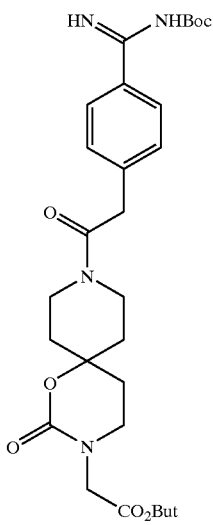

The title compound was prepared using the procedure substantially as described in Example 30D.

FDMS m/z=545.

Step E: Preparation of ((9-(2-(4-(Aminoiminomethyl)phenyl)-acetyl)-2-oxo-1-oxa-3,9-diaza-spiro[5.5]undec-3-yl)acetic Acid.

The title compound was prepared using the procedure substantially as described in Example 30E.

FABMS m/z=389. ELISA: $IC_{50}$=0.20 $\mu$M PRP (ADP): $IC_{50}$=2.13 $\mu$M.

EXAMPLE 33

Preparation of (9-(4-(Aminoiminomethyl)benzoyl)-2-oxo-1-oxa-3,9-diaza-spiro[5.5]undec-3-yl)acetic Acid

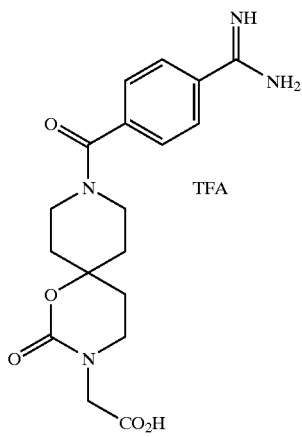

Step A: Preparation of t-Butyl (9-(4-Cyanobenzoyl)-2-oxo-1-oxa-3,9-diaza-spiro[5.5]undec-3-yl)acetate.

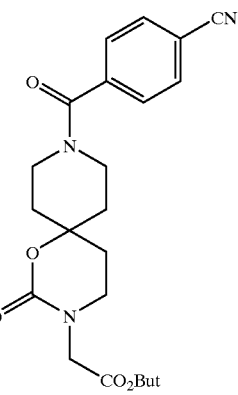

The title compound was prepared using the procedure substantially as described in Example 30C.

FDMS m/z=413.

Step B: Preparation of t-Butyl (9-(4-(N-t-Butoxycarbonylaminoiminomethyl)benxoyl)-2-oxo-1-oxa-3,9-diaza-spiro[5.5]undec-3-yl)acetate.

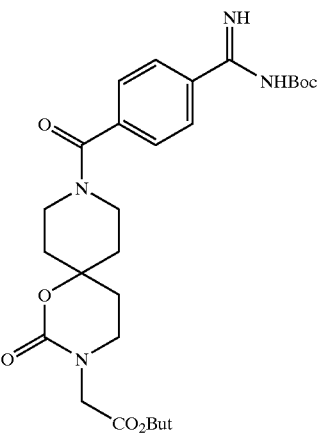

The title compound was prepared using the procedure substantially as described in Example 30D.

FDMS m/z=531.

Step C: Preparation of (9-(4-(Aminoiminomethyl)benzoyl)-2-oxo-1-oxa-3,9-diaza-spiro[5.5]undec-3-yl)acetic Acid.

The title compound was prepared using the procedure substantially as described in Example 30E.

FABMS m/z=375. ELISA: $IC_{50}$=16.5 $\mu$M PRP (ADP): $IC_{50}$=66 $\mu$M.

EXAMPLE 34

Preparation of (8-(4-(Aminoiminomethyl) benzyloxy)-2-oxo-1-oxa-3-aza-spiro[4.5]dec-3-yl) acetic Acid

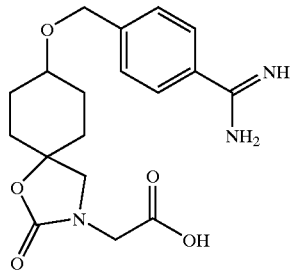

Step A: Preparation of 8-(Ethylene Ketyl)-2-oxo-1-oxa-3-aza-spiro[4.5]decane-3-yl).

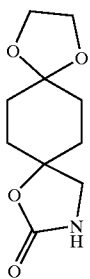

A solution of 1,4-cyclohexanedione mono-ethylene ketal (10 g, 64 mmol) in anhydrous methelane chloride (65 mL) was treated with trimethylsylyl cyanide (9.4 mL, 70.4 mmol), and 18-crown-6 (catalitic). The mixture was stirred at 0° C. under nitrogen for 35 minutes, then diluted with 5 volumes of ethyl acetate. The organic phase was washed with saturated sodium bicarbonate solution, then the organic phase was concentrated in va cuo. The residue was dissolved in tetrahydrofuran, and the resulting solution treated with lithium aluminun hydride. After 1 hour, the reaction mixture was worked-up using the Steinhardt procedure (Fieser & Fieser, Reagents for Organic Synthesis, volume 1, page 584). The filtrate was concentrated in vacuo and the resulting oil dissolved in methanol (50 mL). This'solution was treated with potassium carbonate (8.85 g, 64 mmol). After 1 hour at room temperature, the potassium carbonate was removed by filtration, and the filtrate concentrated in vacuo. The residue was treated with diethyl carbonate (65 mL) and a catalytic amount of sodium hydride. The resulting solution was heated to 125° C. and methanol collected by distillation. After all the methanol had been distilled, a few milliliters of diethyl carbonate were collected by distillation, then the solution was allowed to cool to room temperature. After dilution with ethyl acetate (10 volumes), the organic phase was washed with water and concentrated. The title compound was recrystallized from ethyl acetate/hexane.

Yield=5 g (37%) m.p. 182–184° C.

Step B: Preparation of t-Butyl 8-(Ethylene Ketal)-2-oxo-1-oxa-3-aza-spiro[4.5]dec-3-yl)acetate.

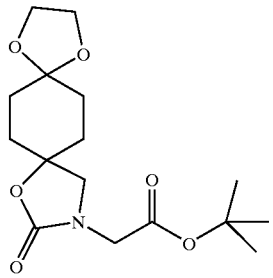

The compound prepared in Step A (2.0 g, 9.38 mmol) in tetrahydrafuran (25 mL) was treated with sodium hydride (60% dispersion in oil, 0.39 g, 10.3 mmol). After heating at reflux for 1 hour, t-Butyl-alpha-bromoacetate (1.32 mL, 10.3 mmol) was added to the reaction mixture. After an additional 1 hour at reflux, the solution was allowed to cool to room temperature. This solution was diluted with ethyl acetate (10 volumes), washed with water, and concentrated in vacuo. The title compound was recrystallized from ethyl acetate/hexane.

Yield=2.8 g (91%) m.p. 144–146° C.

Step C: Preparation of t-Butyl 8-oxo-2-oxo-1-oxa-3-aza-Spiro(4.5]dec-3-yl)acetate.

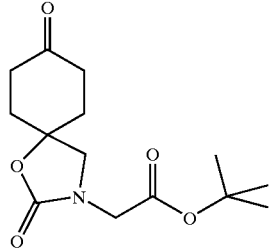

The compound from Step B (3.1 g, 9.47 mmol) in acetone/water (3:1) was treated with pyridinium tosylate. After heating at 65° C. for 16 hours, the reaction was diluted with ethyl acetate (10 volumes). The organic phase was washed with 10% sodium bicarbonate, then concentrated in vacuo. The title compound was recrystallized from ethyl acetate/hexane.

Yield=2.1 g (78%) m.p. 126–129° C. FDMS m/z=284.

Step D: Preparation of (8-(4-Cyanobenzyloxy)-2-oxo-1-oxa-3-aza-spiro[4.5]dec-3-yl)acetate.

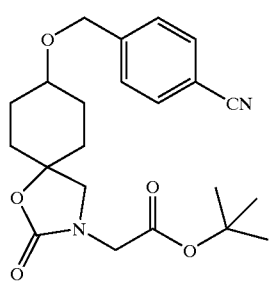

The compound from Step C (0.25 g, 0.882 mmol) in methanol was treated with sodium borohydride (0.033 g, 0.882 mmol). After 2 hours under nitrogen atmosphere, the reaction mixture was concentrated in vacuo. The residue was diluted with tetrahydrafuran (2.5 mL), then treated with sodium hydride (60% dispersion in oil, 0.034 g, 0.882 mmol). After 1 hour at room temperature under nitrogen, this mixture was treated with bromo-p-tolunitrile (0.173 g, 0.882 mmol). After an additional 72 hours, the reaction mixture was diluted with ethyl acetate. The organic phase was washed with water and concentrated in vacua. The residue was purified by silica-gel chromatography, eluting with chloroform/methanol (9:1).

Yield=12 mg (3.3%).

Step E: Preparation of (8-(4-(Aminoiminomethyl) benzyloxy)-2-oxo-1-oxa-3-aza-spiro[4.5]dec-3-yl)acetic Acid.

The compound from Step D (0.012 g, 0.03 mmol) was converted to the title compound using the procedure substantially as described in Examples 30D and 30E.

Yield=6 mg (43%) FDMS m/z=362. ELISA: $IC_{50}$=0.35 μM PRP (ADP): $IC_{50}$=1.29 μM.

EXAMPLE 35

Preparation of (8-(2-(4-(Aminoiminomethyl)phenyl) acetamido)-2-oxo-1-oxa-3-aza-spiro[4.5]dec-3-yl) acetic Acid

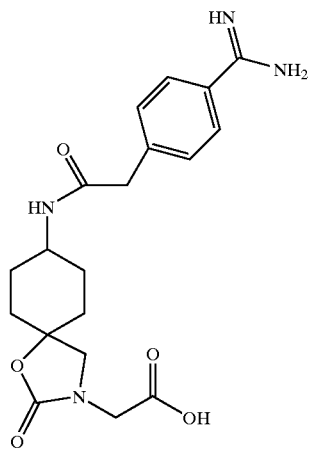

Step A: Preparation of t-Butyl (8-(2-(4-Cyanophenyl)-acetamido)-2-oxo-1-oxa-3-aza-spiro[4.5]dec-3-yl)acetate.

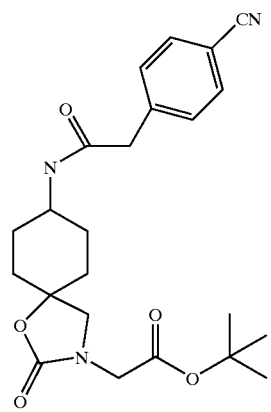

The ketone prepared as described in Example 34C was converted to the title compound using the procedure substantially as described in Example 36A.

Yield=56 mg (15%) FDMS m/z=428.

Step B: Preparation of (8-(2-(4-(Aminoiminomethyl) phenyl)-acetamido)-2-oxo-1-oxa-3-aza-spiro[4.5]dec-3-yl) acetic Acid.

The compound of Step A was converted to the title compound using the procedure substantially as described in Example 36B.

Yield=10 mg (15%) m.p. 193–196° C. FABMS m/z=389. ELISA: $IC_{50}$=0.19 μM PRP (ADP): $IC_{50}$=0.77 μM.

EXAMPLE 36

Preparation of (8-(4-(Aminoiminomethyl) benzamido)-2-oxo-1-oxa-3-aza-spiro[4.5]dec-3-yl) acetic Acid

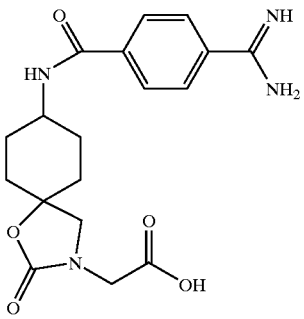

Step A: Preparation of t-Butyl (8-(4-Cyanobenzamido)-2-oxo-1-oxa-3-aza-spiro[4.5]dec-3-yl)acetate.

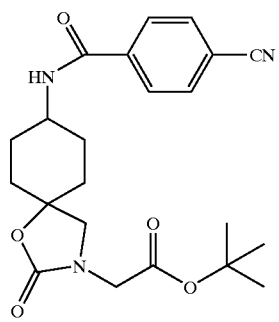

The ketone prepared as described in Example 34C (0.25 g, 0.882 mmol), ammonium acetate (0.68 g, 8.82 mmol), methanol (1.5 mL), was treated with sodium cyanoborohydride (0.055 g, 0.882 mmol). The resulting mixture was stirred at room temperature for 16 hours, then concentrated in vacuo. The residue was dissolved in water, the pH adjusted to pH 10, and the product extracted with ethyl acetate. The combined organic extracts were concentrated in vacua, and the residue dissolved in methylene chloride/pyridine (2.5/1.5 mL). This solution was treated with a solution of 4-cyanobenzoyl chloride (0.160 g, 0.97 mmol) in methylene chloride (1 mL). The resulting solution was stirred under nitrogen for about 1 hour, then diluted with ethyl acetane (10 volumes). The organic phase was washed with water and concentrated in vacuo. The title compound was purified by silica-gel chromatography, eluting with 1% methanol in chloroform. The product was recrystallized from ethyl acetate/hexane.

Yield=105 mg (30%) m.p. 200–205° C. FDMS m/z=414.

Step B: Preparation of (8-(4-(Aminoiminomethyl) benzamido)-2-oxo-1-oxa-3-aza-spiro[4.5]dec-3-yl)acetic Acid.

The product from Step A was converted to the title compound using the procedure substantially as described in Example 34E.

Yield=30 mg (65%) m.p. 280–284° C. FDMS m/z=375. ELISA: $IC_{50}$=0.17 µM PRP (ADP): $IC_{50}$=0.51 µM.

EXAMPLE 37

Preparation of ((8-(4-N-benzyloxycarbonylamino)-1-oxobutyl)-2-oxo-1-oxa-3,8-diaza-spiro[4.5]dec-3-yl)acetate

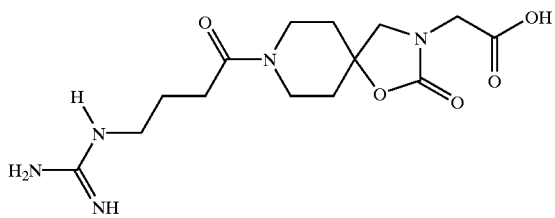

Step A: Preparation of ((8-(4-N-benzyloxycarbonylamino)1-oxobutyl)-2-oxo-1-oxa-3,8-diaza-spiro[4.5]dec-3-yl) acetate.

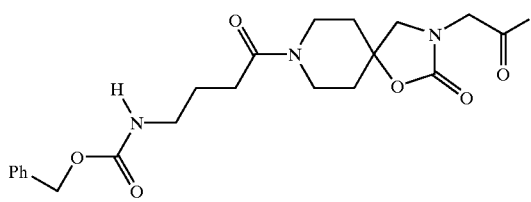

The amine prepared as described in Example 30B was reacted with 4-(N-benzyloxycarbonylamino)butyric-acid using the procedure as described in Example 38A.

Yield=169 mg (93%) FDMS m/z=490.

Step B: Preparation of t-Butyl (8-(4-(di-t-butoxycarbonyl-amninoiminomethyl)-1-oxobutyl)-2-oxo-1-oxa-3,8-diaza-spiro-[4.5]dec-3-yl)acetate.

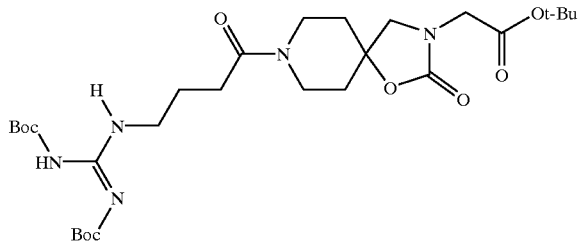

The title compound was prepared from the compound of Step A using the procedures substantially as described in Example 38B.

Yield=160 mg (83%) FDMS m/z=598.

Step C: Preparation of ((8-(4-N-Benzyloxycarbonylamino)-1-oxobutyl)-2-oxo-1-oxa-3,8-diaza-spiro[4.5]dec-3-yl) acetate.

The title compound was prepared from the compound of Step B using the procedure substantially as described in Example 38C.

Yield=90 mg (79%) FDMS m/z 342. ELISA: $IC_{50}$=19 µM PRP (ADP): $IC_{50}$=52 µM.

EXAMPLE 38

Preparation of (8-(4-(Aminoiminomethyl)-1-oxopentyl)-2-oxo-1-oxa-3,8-diaza-spiro[4.5]dec-3-yl)acetic Acid

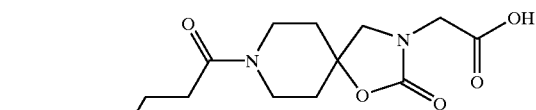

Step A: Preparation of t-Butyl (8-(5-(N-Benzyloxycarbonyl-amino)-1-oxopentyl)-2-oxo-1-oxa-3,8-diaza-spiro[4.5]dec-3-yl)acetate.

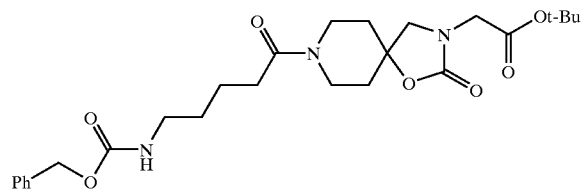

A solution of the amine prepared as described in Example 30B (0.100 g, 0.37 mmol), 5-(N-benzyloxycarbonylamino)-pentolic acid (0.103 g, 0.41 mmol), EDCI (0.105 g, 0.55 mmol), HOBT (0.074 g, 0.55 mmol) 4-DMAP (catalytic) and methylene chloride (2 mL) was stirred at room temperature for 1 hour. This solution was then diluted with ethyl acetate (15 volumes). The resulting solution was washed with water and concentrated in vacuo. The residue was purified by silica-gel chromatography, eluting with chloroform/methanol (95:5).

Yield=160 mg (86%) FDMS m/z=504.

Step B: Preparation of t-Butyl (8-(5-(di-t-Butoxycarbonyl-aminoiminomethyl)-1-oxopentyl)-2-oxo-1-oxa-3,8-diaza-spiro-[4.5]dec-3-yl)acetate.

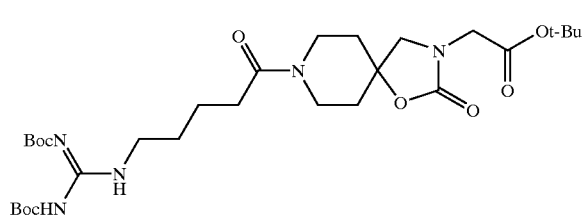

The compound from Step A (0.15 g, 0.298 mmol) and 5% palladium on carbon in absolute ethanol (10 mL) was rapidly stirred under a hydrogen atmosphere for 1 hour. The catalyst was removed by filtration and the filtrate concentrated in vacuo. The residue was treated with bis-Boc-thiourea (0.082 g, 0.298 mmol), triethylamine (0.14 mL, 0.983 mmol) mercury (II) chloride (0.89 g, 0.328 mmol), and dimethylformamide (2 mL). The resulting mixture was stirred at 0° C. for 1½ hours, then at room temperature for 1 hour. This mixture was diluted with ethyl acetate (15 volumes). The resulting mixture was washed with water and concentracted in vacuo. The residue was purified by silica-gel chromatography, eluting with chloroform/methanol (97:7).

Yield=160 mg (88%) FDMS m/z=612.

Step C: Preparation of (8-(4-(Aminoiminomethyl)-1-oxopentyl)-2-oxo-1-oxa-3,8-diaza-spiro[4.5]dec-3-yl)acetic Acid.

The compound from Step B (0.15 g, 0.245 mmol) was treated with trifluoroacetic acid (5 mL). After 1 hour at room temperature, the solution was concentrated in vacuo. The residue was dissolved in water and lyophilized.

Yield=100 mg (88%) FABMS m/z=356. ELISA: $IC_{50}$=1.85 µM PRP (ADP): $IC_{50}$=7 µM.

EXAMPLE 39

Preparation of (8-(6-(Aminoiminomethyl)-1-oxohexyl)-2-oxo-1-oxa-3,8-diaza-spiro[4.5]dec-3-yl)acetic Acid

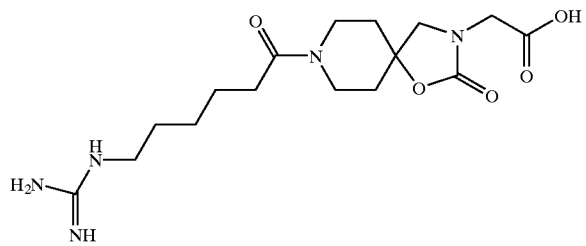

Step A: Preparation of t-Butyl (8-(6-(Benzyloxycarbonyl-amino)-1-oxohexyl)-2-oxo-1-oxa-3,8-diaza-spiro[4.5]dec-3-yl)acetate.

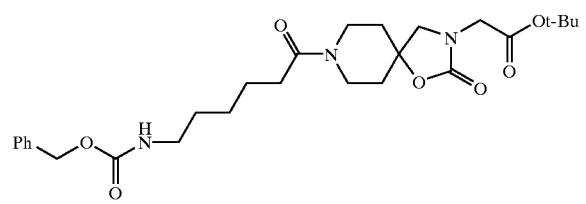

The title compound was prepared from the amine of (6-(N-benzyloxycarbonylamino)hexoic acid substantially as described in Example 38A.

Yield=230 mg (73%) FDMS m/z=518.

Step B: Preparation of t-Butyl (8-(6-(di-t-Butoxytoxy-carbonylaminoiminomethyl)-1-oxohexyl)-2-oxo-1-oxa-3,8-diaza-spiro[4.5]dec-3-yl)acetate.

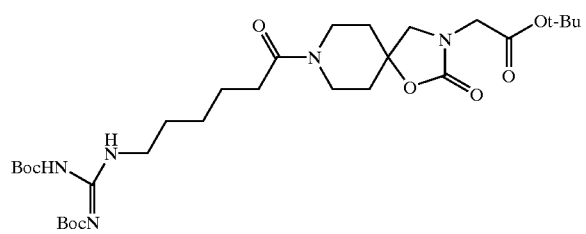

The compound was prepared from the compound of Step A using the procedure substantially as described in Example 38B.

Yield=250 mg (98%) FDMS m/z=626.

Step C: Preparation of (8-(6-(Aminoiminomethyl)-1-oxohexyl)-2-oxo-1-oxa-3,8-diaza-spiro[4.5]dec-3-yl)acetic Acid.

The compound was prepared from the compound of Step B using the procedure substantially as described in Example 38C.

Yield 156 mg (85%), FABMS m/z=370. ELISA: $IC_{50}$=2.7 µM PRP (ADP): $IC_{50}$=12 µM.

EXAMPLE 40

Preparation of 2-(tert-Butoxycarbonyl)-2,9-diaza-spiro[5.5]undecane

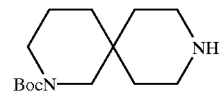

The synthesis of the 2,9-diaza-spiro[5.5]undecane template was accomplished by slightly modifying the procedure utilized for the preparation of the 3,9-diaza-spiro[5.5]undecane as described in U.S. Pat. No. 5,451,578.

Step A:

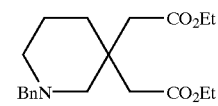

Commercially available 1-benzyl-3-piperidone hydrochloride hydrate (1.89 g) was dissolved in $H_2O$ (10 mL) and then 1M NaOH (9 mL) was added. The solution was stirred at rt for 5 minutes. Extraction with $CH_2Cl_2$ (3×20 mL), drying with $Na_2SO_4$, and removal of solvent under vacuum afforded 1.52 g of the neutralized material.

This material was then dissolved in ice cold EtOH (15 mL) which was saturated with $NH_3$. Then ethyl cyanoacetate (1.7 mL) was added via syringe. The resulting solution was let standing at 0° C. overnight. Evaporation of the solvent gave 2.8 g of a viscous syrup. This syrup was dissolved in $H_2O$ (11 mL) containing concentrated $H_2SO_4$ (13 mL) and the resulting solution was gently refluxed for 3 days. Removal of most of the $H_2O$ under vacuum was followed by azeotropic removal of the rest of the $H_2O$ using EtOH (4×50 mL). The product was then dissolved in EtOH (50 mL) and refluxed overnight. Most of the EtOH was then evaporated. After cooling to 0° C., $H_2O$ (25 mL) added, and then $K_2CO_3$ (19 g) was carefully added with vigorous stirring. The mixture was carefully diluted with $H_2O$ (200 mL) and washed with $CH_2Cl_2$ (2×150 mL). After the organics were dried with $Na_2SO_4$, the solvent was evaporated to afford 2.01 g (69% yield) of the desired diester which was used without further purification.

MS(ES): $(M+H)^+$=348.

Step B:

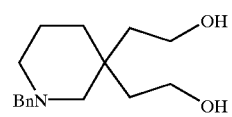

The diester (1.93 g) was dissolved in THF (10 mL) and cooled to −40° C. A commercially available solution of LAH in $Et_2O$ (1M, 8.9 mL) was then slowly added via syringe followed by stirring for 40 minutes as it warmed to rt. After the reaction was cooled to 0° C., sequential addition of $H_2O$ (0.35 mL), 1M NaOH (0.7 mL) and $H_2O$ (0.8 mL) followed. The suspension was stirred vigorously for 1 h at 0° C., diluted with $Et_2O$ (20 mL), and filtered. After thorough rinsing of the solid with $Et_2O$ (150 mL), the solvent was removed under vacuum to afford 1.38 g of the desired diol (94% yield) which was used without further purification.

MS(ES): (M+H)$^+$=264.

Step C:

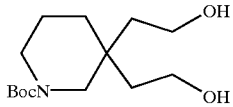

A solution of the N-benzyl diol (1.3 g), di-tert-butyl dicarbonate (1.1 g), and 10%Pd(OH)$_2$/C (130 mg) in MeOH (35 mL) was stirred at 50 psi of H$_2$ overnight. The mixture was filtered through celite and rinsed thoroughly with MeOH. Evaporation of the solvent afforded 859 mg (64% yield) of the desired carbamate which was used without further purification.

MS(ES): (M+H)$^+$=274.

Step D:

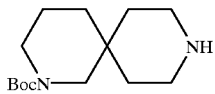

The carbamate (825 mg) was dissolved in anhydrous CH$_2$Cl$_2$ (15 mL) under an argon atmosphere and cooled to −20° C. To this solution was added Et$_2$N (1.23 mL) and then methanesulfonyl chloride (0.51 mL). The solution was stirred for 1 h, then poured into ice cold 1M citric acid (40 mL). This mixture was washed with Et$_2$O (4×30 mL). The combined organic washes were then extracted with saturated NaHCO$_3$ (1×30 mL), dried with MgSO$_4$ and evaporated to give 604 mg (47% yield) of the di-mesylate intermediate which was used without further purification.

MS(ES): (M+H)$^+$=430.

The di-mesylate (600 mg) was dissolved in MeOH (10 mL). Concentrated NH$_4$OH (5 mL) was added and the rection vessel was sealed stirred at 55° C. overnight. After cooling to 0° C., the solution was poured into ice cold 0.5M NaOH (40 mL). Washing with EtOAc (3×50 mL), drying the organics with K$_2$CO$_3$ and solvent evaporation afforded 210 mg of the desired spirocycle.

MS(ES): (M+H)$^+$=254.

EXAMPLE 41

Preparation of 4-((3-(4-Aminoiminomethyl) benzoyl)-3,9-diaza-spiro[5.5]undec-9–25 yl)-4-oxobutanoic Acid

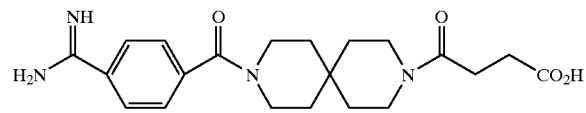

Step A: Preparation of 3-tert-Butoxycarbonyl-9-(4-cyanobenzoyl)-3,9-diaza-spiro[5.5]undecane

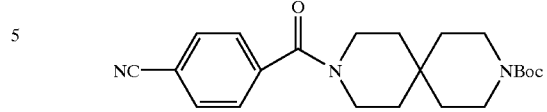

The synthesis of the starting material, 3-tert-butoxycarbonyl-3,9-diaza-3,9-spiro[5.5]undecane, was accomplished as described in U.S. Pat. No. 5,451,578. This material (1.45 g) was dissolved in CH$_2$Cl$_2$ (25 mL) and cooled to 0° C. under an argon atmosphere. To this solution was added triethylamine (1.67 mL) and 4-dimethylaminopyridine (70 mg) followed by 4-cyanobenzoyl chloride (1.04 g). The mixture was stirred overnight as it warmed to rt. It was cooled to 0° C., and ice cold 1M HCl (30 mL) was carefully added. The resulting mixture was washed with EtOAc (3×30 mL). Then washing the EtOAc with saturated NaHCO$_3$ and brine followed by drying with MgSO$_4$ and evaporation of the solvent under reduced pressure afforded the title compound (1.62 g, 74%) as a yellow foam. Chromatography on silica gel with hexanes/ethyl acetate (2:1) as eluant gave pure compound.

MS(ES): (M+H)$^+$=384.

Step B: Preparation of 4-(3-(4-Cyanobenzoyl)-3,9-diaza-spiro[5.5]undec-9-yl)-4-oxobutanoic acid:

To the material obtained in step A (100 mg) was added 40% TFA in CH$_2$Cl$_2$ (2.5 mL) at rt. After stirring for ½ h, the solvent was evaporated. The resultant residue was dissolved in anhydrous CH$_2$Cl$_2$ (3 mL) under argon and cooled to 0° C. After adding triethylamine (0.13 mL), succinic anhydride (30 mg) in CH$_2$Cl$_2$ (1.4 mL) was added. Stirring was continued overnight as it warmed to rt. The solvent was then evaporated and the residue was partitioned between 1M HCl (15 mL) and EtOAc (4×15 mL). The combined organics were washed with brine (30 mL), dried with MgSO$_4$, and evaporated to afford 73 mg (74% yield) of the desired acid.

MS(ES): (M+H)$^+$=384.

Step C: Preparation of the Title Compound:

H$_2$S gas was bubbled gently for 10 minutes into a pyridine (4 mL) solution of the cyano acid (70 mg) obtained in part B containing triethylamine (0.22 mL). After the resultant solution was stirred at rt overnight, argon was bubbled through the solution for ½ h to remove excess H$_2$S. This pyridine solution was poured into 1M HCl (50 mL) and then saturated with NaCl. This solution was then washed with EtOAc (6×20 mL). The combined EtOAc was dried over MgSO$_4$ and evaporated to give 73 mg of a yellow semi-solid.

The yellow semi-solid was suspended in acetone (10 mL) and then methyl iodide (3 mL) was added. After stirring overnight at rt the solvent was evaporated to give 103 mg of a yellow semi-solid.

This material was then dissolved in ETOH (15 mL) and then ammonium acetate (2 g) was added. The resultant solution was stirred at 60° C. overnight. Evaporation of the solvent afforded crude product which was then purified using reversed phase high pressure liquid chromatography (RP-HPLC).

MS(ES): (M+H)$^+$=401. ELISA: IC$_{50}$=15 μM. PRP (ADP): IC$_{50}$=14 μM.

EXAMPLE 42

Preparation of 5-((3-(4-Aminoiminomethyl)benzoyl)-3,9-diaza-spiro[5.5]undec-9-yl)-5-oxopentanoic Acid

The title compound was prepared by substantially following the procedure in Example 40 except that glutadc anhydride was used in place of succinic anhydride in step B.

MS(ES): (M+H)$^+$=415. ELISA: IC$_{50}$=3.5 μM. PRP (ADP): IC$_{50}$=10 μM.

EXAMPLE 43

Preparation of Ethyl (3-(4-Aminolminomethyl)benzoyl)-2-aza-spiro[5.5]undec-9-yl)acetate Hydrochloride

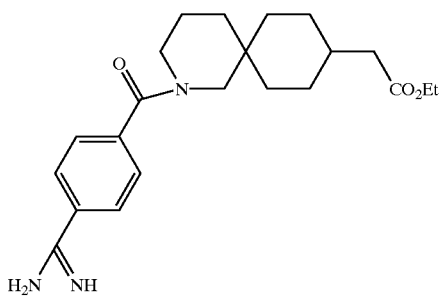

Step A: Preparation of Benzyl-9-oxo-2-aza-spiro[5.5]undec-7-ene-3-carboxylate

A solution of benzyl-3-formylpiperidine-1-carboxylate (1 mmol) and methylvinyl ketone (1.2 mmol) was dissolved in MeOH (1 mL) and H$_2$O (1 mL). To this added catalytic amount of KOH and the solution was refluxed for 1 hour. To this then added powdered molecular sieves and refluxed for another 1 h. The HPLC analysis showed the completion of the reaction. The molecular sieves are filtered and the filtrate was evaporated. The residue was disssolved in CH$_2$Cl$_2$ and washed with water, dried, filtered and evaporated to give the desired spirocyclic enone as a yellow oil in 60% yield.

Step B: Preparation of Benzyl-9(ethoxycarbonyl)methylene)2-aza-spiro[5.5]undec-7-ene-3-carboxylate

To the suspension of sodium hydride (3mmol) in THF (2 mL) at 0° C. was added triethylphoshonoacetate and then stirred for 30 min at 0° C. A solution of spiro compound (1 mmol) from previous step in THF (2 mL), and the reaction was heated to 50° C. for 8 h. The mixture was poured into water and extracted with ethylacetate. The title compound was purified by flash chromatography on silica gel using ethylacetate/hexane to give the desired pure compound as a colorless oil (50%)

Step C: Preparation of Ethyl (2-aza-spiro[5.5]undec-9-yl)acetate

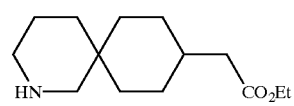

The protected spiro compound from Step B was dissolved in 10 mL of ethanol, and to this added Pd(II) hydroxide on carbon. The reaction was carried at 50 psi H2 pressure for 18 h. The catalyst was removed by filtering through celite, and the filtrate concentrated to give oil in 70% yield.

Step D: Preparation of Ethyl (3(4-cyanobenzoyl)-2-aza-spiro[5.5]undec-9-yl)acetate

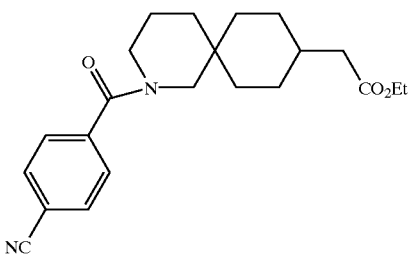

The 1 mmol of compound from previous step and triethylamine (3 mmol) were dissolved in dry CH$_2$Cl$_2$. To this added 4-cyanobenzoyl chloride (1.1 mmol) and solution was stirred for 12 hours at room temperature. The solvent was evaporated and the residue treated with water and extracted the product with ethylacetate. The organic layer was washed with 10% HCl solution, dried, and solvent removed to afford crude product. The product was purified on reverse phase HPLC to afford desired material as a yellow oil (60%).

Step E: Preparation of Ethyl (34-(Hydroxyiminomethyl)benzoyl)-2-aza-spiro[5.5]undec-9-yl)acetate Hydrochlorlde To a solution of nitrile (1 mmol) in ethanol (5 mL) was added hydroxylamine hydrochloride (2 mmol) and triethylamine (2 mmol). The reaction mixture was heated to 65° C. and stirred for 3 hours. The solvent was evaporated and diluted with water and extracted the product with ethylacetate. The organic layer was dried, filtered and evaporated to afford hydroxyamidino compound as a white solid.

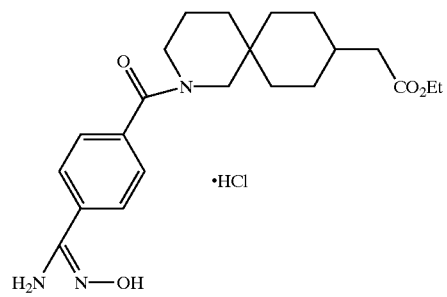

Step F: Preparation of Ethyl (3(4-Aminoiminomethyl) benzoyl)-2-aza-spiro[5.5]undec-9-yl)acetate.

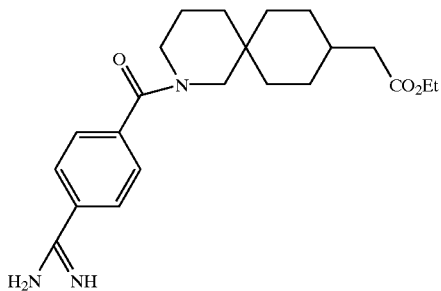

To a suspension of the product from Step E in HOAc was added 5% Pd/C (50% wet). The mixture was heated at 50° C. using 45 psi H2 for 18 hours. The catalyst was filtered and the solvent evaporated under reduced pressure. The crude residue from this step was taken to next step without further purification Step G: Preparation of (3-(4-Aminolminomethyl)benzoyl)-2-aza-spiro[5.5]undec9-yl)acetic Acid

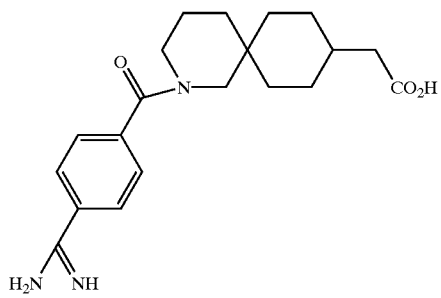

50 mg of the ester from step F was treated with LiOH (4 eq) in H$_2$O and THF. The solution was stirred overnight, HPLC analysis showed completion of the reaction. The solvent was evaporated and the residue was purified on reverse phase HPLC to afford the desired pdt as a white solid in 50% yield. ESMS: 358(MH+)

EXAMPLE 44

Preparation of (3-(4-(Aminomethyl)benzoyl)3-asa-spiro[5.5]undec-9-yl)propionlc Acid

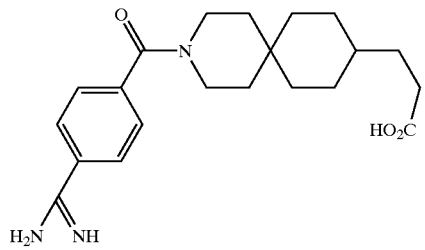

Step A Preparation of Benzyl -9-(ethoxycarbonyl)ethylene) 3-aza-spiro[5.5]undec-7-ene-carboxylate

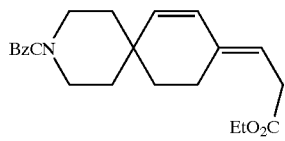

The spiro ketone (1 mmol), synthesized from N-carbobenzyloxy-4-formylpiperidine following the same procedure as in Example 1 (Step A) in THF was added to THF solution of triethyl phosphonopropionate and sodium hydride. The reaction mixture was heated at 50° C. for 8 h, followed by addition of water and extracting the product with dichloromethane. The dichloromethane layer was dried, filtered, evaporated to give light yellow oil. This was purified by silica gel chromatography to give colorless oil as the desired product Step B: Preparation of Ethyl (3-aza-Spiro[5.5]undec-9-yl) propionate

The protected spiro compound from Step A was dissolved in 10 mL of ethanol, and to this added Pd(II) hydroxide on carbon. The reaction was carried at 50 psi H2 pressure for 18 h. The catalyst was removed by filtering through celite, and the filtrate concentrated to give oil.

Step C: Preparation of Ethyl (3-(4-Cyanobenzoyl)-3-aza-spiro[5.5]undec-9-yl)propionate

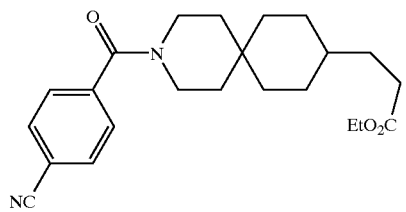

The 1 mmol of compound from previous step and triethylamine (3 mmol) were dissolved in dry CH$_2$Cl$_2$. To this added 4-cyanobenzoyl chloride (1.1 mmol) and solution was stirred for 12 hours at room temperature. The solvent was evaporated and the residue treated with water and extracted the product with ethylacetate. The organic layer was washed with 10% HCl solution, dried, and solvent removed to afford crude product. The product was purified on reverse phase HPLC as a yellow oil.

Step D: Preparation of Ethyl (3-(4-(Hydroxyiminomethyl) benzoyl)-3-aza-spiro[5.5]undec-9-yl)propionate Hydrochloride To a solution of nitrile (1 mmol) in ethanol (5 mL) was added hydroxylamine hydrochloride (2 mmol) and triethylamine (2 mmol). The reaction mixture was heated to 65° C. and stirred for 3 hours. The solvent was evaporated and diluted with water and extracted the product with ethylacetate. The organic layer was dried, filtered and evaporated to afford hydroxyamidino compound as a white solid.

Step E: Preparation of Ethyl (3-(4-Aminoiminomethyl)benzoyl)-3-aza-spiro[5.5]undec-9-yl)propionate.

To a suspension of the product from Step E in HOAc was added 5% Pd/C (50% wet). The mixture was heated at 50° C. using 45 psi $H_2$ for 18 hours. The catalyst was filtered and the solvent evaporated under reduced pressure. The crude residue from this step was taken to next step without further purification Step F: Preparation of (3-(4-Aminoiminomethyl)benzoyl)-3-aza-spiro[5.5]undec-9-yl)proplonic Acid

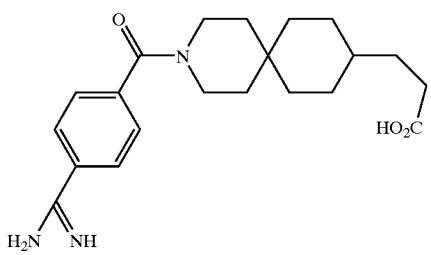

50 mg of the ester from step F was treated with LiOH (4 eq) in $H_2O$ and THF. The solution was stirred overnight, HPLC analysis showed completion of the reaction. The solvent was evaporated and the residue was purified on reverse phase HPLC to afford the desired pdt as a white solid.

EXAMPLE 45

Preparation of (3-(4-Aminoiminonethyl)benzoyl)-3-aza-spiro[5.5]undec-9-carbonyl)formic Acid Hydrochloride

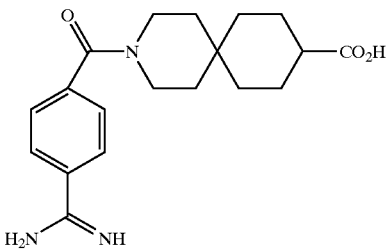

Step A Preparation of 3-{2[(3-Azaspiro[5.5]undecane-9-diethyl Ester

1-Benzyl-4-piperidone was converted to the bismesylate as described in (see Patent No. 5,451,578 for detailed procedure). To a slurry of 60% NaH (3 mmol) in toluene (10 mL) under argon, was slowly added diethyl malonate (1.5 mmol). The mixture was cooled to 0° C. and bis-mesylate (1 mmol) was added and the mixture heated to reflux for 18 h. The reaction was quenched into 10% citric acid and product extracted with dichloromethane. The crude residue was purified by flash chromatography to give the desired diester in 65% yield.

Step B. Preparation of 3-{2[(3-Azaspiro[5.5]undecane-9-carbonyl)formic Acid

To a solution of diester (300 mg) in THF (5 mL) is added 1N LiOH (4 mL) and stirred the reaction for 3 days at room temperature. The pH was adjusted to 2.5 and product extracted with ethylacetate. This mixture was redissolved in THF and added 1N LiOH and the reaction was heated at 80° C. overnight. The pH was again adjusted to 2 and the desired acid extracted with ethylacetate. The organic layer was dried, filtered and evaporated to give desired Boeacid as white foam (200 mg, 80%).

Step C: Preparation of (3-(4-Cyano)benzoyl)-3-aza-spiro[5.5]undec-9-carbonyl)formic Acid Hydrochloride

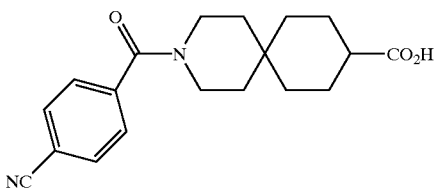

To a solution of the BOC-acid (150 mg) in $CH_2Cl_2$ (2 mL) at 0° C. is added TFA(2 mL). The solution is stirred at 0° C. for 2 h. The solvent and excess TFA are evaporated to an oily residue, which was used as such for the acylation step. The acid (1 mmol) is dissolved in $CH_2Cl_2$ (5 mL), added triethylamine (2 mmol) followed by p-cyanobenzoyl chloride (1.05 mmol). The solution was stirred for 12 hours at room temperature. The solvent was evaporated and residue was suspended in water and extracted the product with ethyl acetate. The organic layer is dried, filtered and evaporated to give crude product. The desired acylated material was isolated as a pure material after silica gel chromatography in approximately 60% yield. ES-MS: 327 (M+H+)

Step D: Preparation of (3-4-Aminoiminomethyl)benzoyl)-3-aza-spiro[5.5]undec-9-carbonyl)formic Acid Hydrochloride

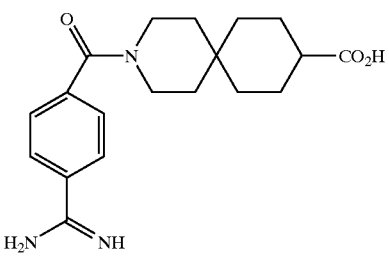

A solution The nitrilewas dissolved in a mixture of pyridine and triethylamine, and this was saturated with hydrogen sulfide,left at room temperature overnight. Then poured into water and extracted with ethylacetate. The ethylacetate layer was concentrated and to this added acetone and methyl iodide followed by reflux for 2 h. After that concentrated the precipitate, dissolved in ethanol, treated with ammonium acetate and heated for 2 h at 60° C. The solvent was removed to give the amidine functionality.

The following assay methods are suitable for evaluating the compounds of the invention.

No. 1—The ELISA IIb-IIIa Assay:

In the following assay, GPIIb-IIIa is prepared in purified form, by a method such as described by Fitzgerald, L. A., et al., *Anal Biochem* (1985) 151:169–177, (the disclosure of which is incorporated herein by reference). GPIIb-IIIa is coated onto microtiter plates. The coated support is then contacted with fibrinogen and with the test material (e.g., compounds of Formula I) and incubated for a sufficient time to permit maximal binding of fibrinogen to the immobilized GPIIb-IIIa. Fibrinogen is typically provided at a concentration of about 5–50 nM and the test material can, if desired, be added at a series of dilution. Typical incubations are 2 to 4 hours at 25° C., the time and temperature being interdependent.

After incubation, the solution containing the fibrinogen and test material is removed and the level of binding of fibrinogen measured by quantitating bound fibrinogen to GPIIb-IIIa. Any suitable means of detection may be used, but it is convenient to employ labeled fibrinogen, for example using biotinylated labels. Such methods are well known in the art.

A. Description of Assays—Plate Assays

Purified platelet GPIIb-IIIa receptor was prepared as described by Fitzgerald, L. A., et al., *Anal Biochem* (1985) 151:169–177 (1985). Vitronectin receptor was prepared as described by Smith, J. W., *J. Biol Chem* (1988) 263:18726–18731. After purification, the receptors were stored in 0.1% Triton X-100 at 0.1–1.0 mg/ml.

The receptors were coated to the wells of 96-well flat-bottom ELISA plates (Linbro EIA-Plus microtiter plate, Flow Laboratories) after diluting 1:200 with a solution of 20 mM Tris-HCl, 150 mM NaCl, 1 mM $CaCl_2$, pH 7.4, to reduce the Triton X-100 concentration to below its critical micellar concentration and adding an aliquot of 100 ul to each well. The wells were all allowed to incubate overnight at 4° C., and then aspirated to dryness. Additional sites were blocked by the addition of bovine serum albumin (BSA) at 35 mg/ml in the above buffer for two hours at 30° C. to prevent nonspecific binding. The wells were then washed once with binding buffer (50 nM Tris-HCl, 100 mM NaCl 2 mM $CaCl_2$, 1 mg/ml BSA).

The corresponding ligands (fibrinogen, von Willebrand Factor, or vitronectin) were conjugated to biotin using commercially available reagents and standard protocols. The labeled ligands were added to the receptor-coated wells at final concentration of 10 nM (100 ul/well) and incubated for 3 hours at 25° C. in the presence or absence of the test samples. After incubation, the wells are aspirated to dryness and bound ligand is quantitated.

The bound protein is detected by the addition of antibiotin antibody conjugated to alkaline phosphatase followed by addition of substrate (p-nitrophenyl phosphate), and determination of the optical density of each well at 405 nM. Decreased color development is observed in wells incubated with test samples which inhibit binding of ligand to receptor.

No. 2—The Platelet Aggregation Assay

In addition to the ELISA IIb-IIIa assay previously described the Aggregation-Human PRP/ADP Assay is useful for evaluating therapeutic compounds.

Platelet-rich plasma was prepared from healthy human volunteers for use in determining inhibition of platelet aggregation by the compounds. Blood was collected via a 21-gauge butterfly cannula, using a two-syringe technique into 1/10 volume of 3.8% trisodium citrate.

Platelet-rich plasma was prepared at room temperature by centrifugation of the citrated whole blood at 100×g for twelve minutes. The platelet rich plasma contained approximately 200–400,000 platelets/$\mu$l.

Platelet-poor plasma was prepared by centrifugation of citrated whole blood at 12,000×g for 2 minutes.

Platelet aggregation was assayed in a 4-channel platelet aggregatiob profiler (PAP-4, Biodata, Hatboro, Pa.) according to the manufacturers directions. Inhibition of platelet aggregation was studied by adding varying amounts of adenosine diphosphate (ADP) to stirred human platelet-rich plasma. Specifically, the human platelet-rich plasma was incubated with the compound being tested for 1 minute at 37° C. prior to the addition of a variety of aggregating agents most often ADP 5 $\mu$M, but also 1 $\mu$g/ml collagen, 1 $\mu$M U46619 and 0.3 $\mu$M platelet activating factor.

Pharmaceutical Compositions

Pharmaceutical formulations containing compounds of the invention can be administered orally in the form of tablets, capsules, solutions, emulsions or suspensions, inhaled liquid or solid particles, as a spray, through the skin by an appliance such a transdermal patch (such as described in U.S. Pat. Nos. 5,296,222 and 5,271,940, the disclosures of which are incorporated herein by reference) or rectally, for example, in the form of suppositories. The lipophilic pro-drug derivatives of the invention are particularly well suited for transdermal absorption administration and delivery systems. Administration can also take place parenterally, for example in the form of injectable solutions.

Tablets are prepared by mixing the Active Ingredient ("Active Ingredient" is one or more spiro bicyclic compounds of the invention inclusive of those corresponding to formulae I) with pharmaceutically inert, inorganic or organic carriers, diluents, and/or excipients. Examples of such excipients which can be used for tablets, are lactose, maize starch or derivatives thereof, talc, stearic acid or salts thereof. Examples of suitable excipients for soft gelatin capsules are vegetable oils, waxes, fats, semisolid and liquid polyols.

Suitable excipients for the preparation of solutions and syrups are water, polyols, sucrose, invert sugar and glucose.

Suitable excipients for injectable solutions are water, alcohols, polyols, glycerol and vegetable oils.

These pharmaceutical products can additionally contain preservatives, solubilizers, stabilizers, wetting agents, emulsifiers, sweeteners, colorants, flavorings, buffers, coating agents and antioxidants.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use.

The.Active Ingredient can also be made in micro-encapsulated form.

Exemplary formulations using the Active Ingredient are described below:

Formulation 1

Hard gelatin capsules are prepared using the following ingredients:

|  | (mg/capsule) |
| --- | --- |
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the ingredients below:

|  | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

|  | Weight % |
|---|---|
| Active ingredient | 5 |
| Lactose | 95 |

The active mixture is mixed with the lactose and the mixture is added to a dry powder inhaling appliance.

Formulation 4

Tablets, each containing 60 mg of active ingredient, are prepared as follows:

|  | (milligrams) |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules as produced are dried at 50–60° C. Iand passed through a 16 mesh U.S. sieve. The sodium carboxymethyl starch, magnesium stearate, and talc, previously passed through a No. 30 mesh U.S. sieve, are then added to the granules which, after mnixing, are compressed on a tablet machine to yield tablets each weighing 150 mg.

Formulation 5

Capsules, each containing 80 mg of medicament are made as follows:

|  | (milligrams) |
|---|---|
| Active ingredient | 80.0 |
| Starch | 109.0 |
| Magnesium stearate | 1.0 |
| Total | 190.0 |

The active ingredient, cellulose, starch, and magnesium stearate are blended passed through a No. 20 mesh U.S. sieve, and filled into hard gelatin capsules in 190 mg quantities.

Formulation 6

Suppositories, each containing 225 mg of active ingredient are made as follows:

| Active Ingredient | 225 mg |
|---|---|
| Saturated fatty acid glycerides to | 2000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

| Active ingredient | 50.0 mg |
|---|---|
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of medicament, are made as follows:

|  | (milligrams) |
|---|---|
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Method of Treatment

This invention provides a method of preventing or treating thrombosis in mammals, especially humans, which method comprises administering to the human or mammal a therapeutically effective amount of the compounds of this invention. The platelet aggregation inhibitors of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation on vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the compounds, the amount of which will vary depending upon the length of proposed storage time, the conditions of storage, the ultimate use of the stored material, etc.

Preferably, the compounds of this invention are administered in the form of a pharmaceutical formulation. Thus, the compounds of this invention may be administered orally, parenterally, topically, rectally and etc., in, appropriate dosage units, as desired.

The term parenteral as used herein includes subcutaneous, intravenous, intraarterial, injection or infusion techniques, without limitation. The term, "topically" encompasses administration rectally and by inhalation spray, as well as the more common routes of the skin and the mucous membranes of the mouth and nose.

Actual dosage levels of active ingredients in the pharmaceutical compositions of this invention may be varied so as to administer an amount of the active compound(s) that is effective to achieve the desired therapeutic response for a particular patient.

The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

The range of therapeutic dosages is from about 0.01 to about 10,000 milligrams per day, with from 1 to 300 milligrams being preferred.

Many modifications and variations of this invention may be made without departing from its scope, as is apparent to those skilled in the art. The specific embodiments described herein are offered by way of example only, and the invention is to be limited only by the terms of the appended claims.

What is claimed is:

1. A compound of formula (I):

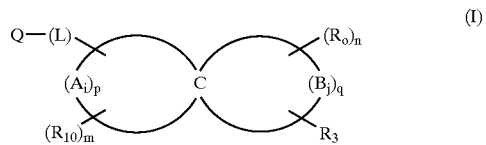

wherein;

the spirocycle having $(A_i)_p$, C, and $(B_j)_q$ is

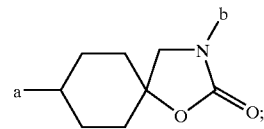

m is a number from zero to 9;

$R_{10}$ is the same or different and is a non-interfering substituent independently selected from alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, or sulfo;

n is a number from zero to 2;

$R_0$ is the same or different and is a non-interfering substituent independently selected from alkyl, halosubstituted alkyl, alkenyl, alkynyl, cycloalkyl, aryl, arylalkyl, hydroxy, alkoxy, arylalkoxy, amino, substituted amino, carbamoyl, carboxy, acyl, cyano, halo, nitro, or sulfo;

where Q—(L) is attached at a, and $R_3$ is attached at b;

the linking group —(L)— is a bond or a substituted or unsubstituted chain selected from the group consisting of CO, CO($C_1$–$C_6$ alkyl), O($C_1$–$C_6$ alkyl), NHCO, and $C_1$–$C_6$ alkyl;

Q is a basic group selected from the group consisting of amino, imino, amidino, hydroxyamidino, N-alkylamidine, N,N'-dialkylamidine, N-arylamidine, aminomethyleneamino, iminomethylamino, guanidino, aminoguanidino, alkylamino, dialkylamino, trialkylamino, alkylideneamino, pyrrolyl, imidazolyl, pyrazolyl, pyridyl, pyrazinyl, pyrimidinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, amide, thioamide, benzamidino, pteridinyl, 4aH-carbozolyl, carbozolyl, beta-carbolinyl, phenanthridinyl, acridinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl quinuclidinyl, morpholinyl, any of the foregoing radicals substituted on a benzene ring, optionally substituted with $R_{2c}$ wherein $R_{2c}$ is hydrogen or halogen and any of the foregoing radicals substituted by amino, imino, amidino, hydroxyamidino, aminomethyleneamino, iminomethylamino, guanidino, alkylamino, dialkylamino, trialkylamino, tetrahydroisoquinoline, dihydrosioindole, alkylideneamino or

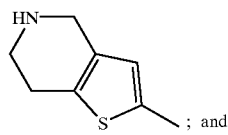
; and $R_3$ is an acidic group selected from the group consisting of $CO_2R_5$, $(C_1-C_6$ alkyl$)CO_2R_5$, $CO(C_1-C_6$ alkyl$)CO_2R_5$, $CONH(C_1-C_6$ alkyl$)CO_2R_5$, $(C_1-C_6$ alkyl$)CH(NHR_4)CO_2R_5$, $CO(C_1-C_6$ alkyl$)CH(NHR_4)CO_2R_5$, or $CONH(C_1-C_6$ alkyl$)CH(NHR_4)CO_2R_5$, wherein $R_4$ is $SO_2(C_1-C_6$ alkyl$)$, $SO_2$ aryl, or $SO_2$(substituted aryl); and $R_5$ is hydrogen, $C_1-C_6$ alkyl, aryl, or substituted aryl;

or a pharmaceutically-acceptable salt, solvate or prodrug thereof.

2. The compound of claim 1, wherein Q is pyridin-4-yl, piperidin-4-yl, amidino, hydroxyamidino, guanidinyl, or a group of the formula:

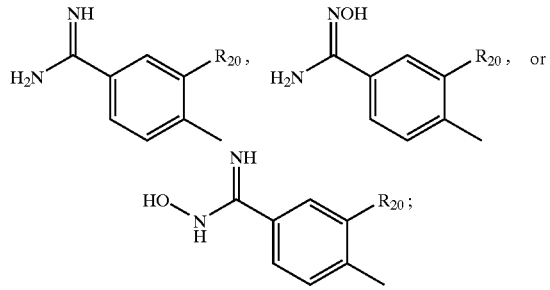

wherein $R_{20}$ is hydrogen or halogen.

3. The compound of claim 1, wherein Q is a group of the formula:

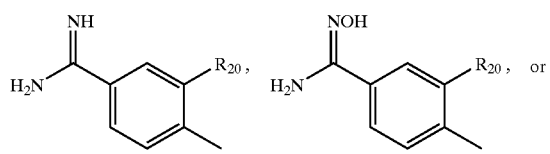

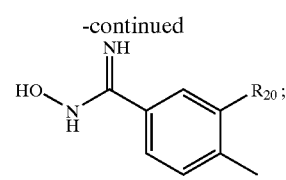

wherein $R_{20}$ is hydrogen or halogen.

4. The compound of claim 1, wherein $R_3$ is $CO_2R_5$, $(C_1-C_6$ alkyl$)CO_2R_5$, $CO(C_1-C_6$ alkyl$)CO_2R_5$, or $CONH(C_1-C_6$ alkyl$)CO_2R_5$.

5. The compound of claim 4, wherein $R_5$ is hydrogen.

6. The compound of claim 1, wherein $R_3$ is $(C_1-C_6$ alkyl$)CH(NHR_4)CO_2R_5$, $CO(C_1-C_6$ alkyl$)CH(NHR_4)CO_2R_5$, or $CONH(C_1-C_6$ alky]$)CH(NHR_4)CO_2R_5$.

7. The compound of claim 6, wherein $R_5$ is hydrogen.

8. The compound of claim 1, wherein L is $O(C_1-C_6$ alkyl$)$, CO or NHCO.

9. The compound of claim 1, wherein L is a bond.

10. The compound of claim 1, wherein Q is pyridin-4-yl, piperidin-4-yl, amidino, hydroxyamidino, guanidinyl, or a group of the formula:

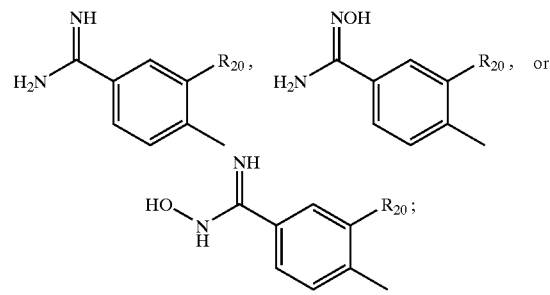

wherein $R_{20}$ is hydrogen or halogen; and wherein $R_3$ is $CO_2R_5$, $(C_1-C_6$ alkyl$)CO_2R_5$, $CO(C_1-C_6$ alkyl$)CO_2R_5$, or $CONH(C_1-C_6$ alkyl$)CO_2R_5$.

11. The compound of claim 1, wherein Q is a group of the formula:

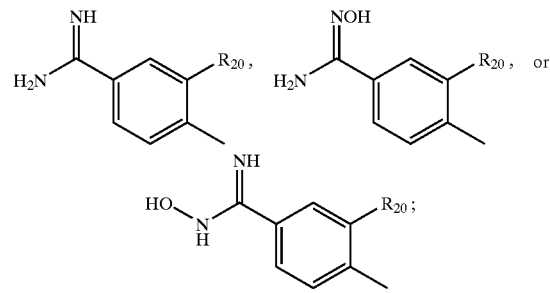

and $R_3$ is $(C_1-C_6$ alkyl$)CO_2R_5$.

12. The compound of claim 1, wherein Q is a group of the formula:

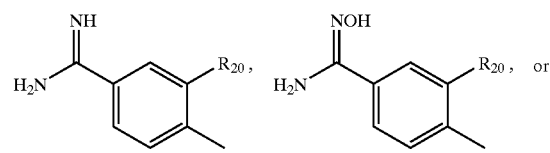

-continued

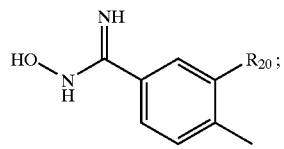

and L is O(C$_1$–C$_6$ alkyl), CO or NHCO.

13. The compound of claim 1, wherein R$_3$ is (C$_1$–C$_6$ alkyl)CO$_2$R$_5$ and L is O(C$_1$–C$_6$ alkyl), CO or NHCO.

14. The compound of claim 1 selected from the group consisting of:

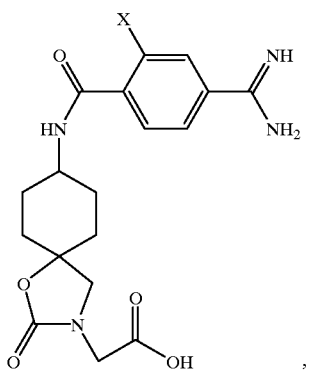

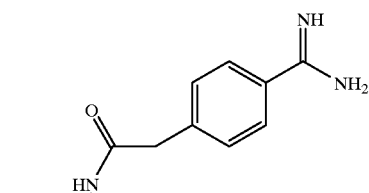

, and

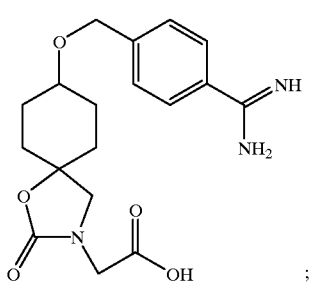

;

wherein X is F or H, or a pharmaceutically-acceptable salt, solvate, or prodrug thereof.

15. The compound of claim 1 having the formnula:

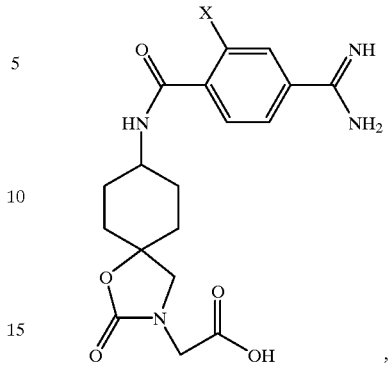

wherein X is F or H, or a pharmaceutically-acceptable salt, solvate, or prodrug thereof.

16. The compound of claim 1 having the formula:

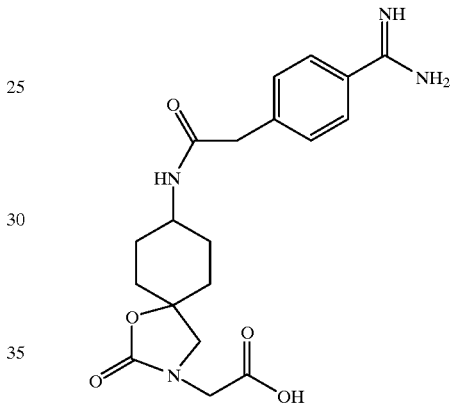

or a pharmaceutically-acceptable salt, solvate, or prodrug thereof.

17. The compound of claim 1 having the formula:

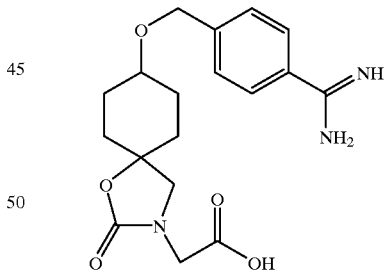

or a pharmaceutically-acceptable salt, solvate, or prodrug thereof.

18. A composition for inhibiting the binding of fibrinogen to blood platelets in a mammal, comprising a compound of claim 1 and a pharmaceutically-acceptable carrier.

19. A composition for inhibiting the aggregation of blood platelets in a mammal, comprising a compound of claim 1 and a pharmaceutically-acceptable carrier.

20. A composition for preventing or treating thrombosis in a mammal, comprising a compound of claim 1 and a pharmaceutically-acceptable carrier.

21. A method for inhibiting the binding of fibrinogen to blood platelets in a mammal, which comprises administering to the mammal a composition of claim 18.

22. A method for inhibiting the aggregation of blood platelets in a mammal, which comprises administering to the mammal a composition of claim 19.

23. A method for preventing or treating thrombosis in a mammal, which comprises administering to the mammal a composition of claim 20.

24. A composition for treating a mammal to alleviate the pathological effects of atheroschlerosis, arterioschlerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts, comprising a compound of claim 1 and a pharmaceutically-acceptable carrier.

25. A method of treating a mammal to alleviate the pathological effects of atheroschlerosis, arterioschlerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts; wherein the method comprises administering to said mammal at least one compound of claim 1; wherein, said compound is administered to said mammal in an amount sufficient to inhibit binding of fibrinogen on glycoprotein IIb–IIIa sites in said mammal to thereby alleviate said effects.

26. A pharmaceutical formulation containing as an active ingredient a compound of claim 1, associated with one or more pharmaceutically-acceptable carriers therefor.

* * * * *